(12) United States Patent
Lim et al.

(10) Patent No.: US 10,258,675 B2
(45) Date of Patent: *Apr. 16, 2019

(54) TREATMENT OF DISEASE USING INTER-ALPHA INHIBITOR PROTEINS

(71) Applicants: ProThera Biologics, Inc., Providence, RI (US); Women & Infants Hospital of Rhode Island, Providence, RI (US)

(72) Inventors: Yow-Pin Lim, Providence, RI (US); Barbara Stonestreet, Barrington, RI (US)

(73) Assignees: ProThera Biologics, Inc., Providence, RI (US); Women & Infants Hospital of Rhode Island, Providence, RI (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/407,805

(22) Filed: Jan. 17, 2017

(65) Prior Publication Data
US 2017/0252416 A1 Sep. 7, 2017

Related U.S. Application Data

(63) Continuation of application No. 14/426,832, filed as application No. PCT/US2013/058791 on Sep. 9, 2013, now Pat. No. 9,572,872.

(60) Provisional application No. 61/698,651, filed on Sep. 9, 2012.

(51) Int. Cl.
A61K 38/57 (2006.01)

(52) U.S. Cl.
CPC ............. *A61K 38/57* (2013.01); *Y02A 50/385* (2018.01); *Y02A 50/393* (2018.01)

(58) Field of Classification Search
None
See application file for complete search history.

(56) References Cited

U.S. PATENT DOCUMENTS

| | | | |
|---|---|---|---|
| 4,839,298 A | 6/1989 | Kay et al. | |
| 5,166,133 A | 11/1992 | Houston et al. | |
| 5,777,081 A | 7/1998 | Michalski et al. | |
| 5,948,894 A | 9/1999 | Berry et al. | |
| 6,069,236 A | 5/2000 | Burnouf-Radosevich et al. | |
| 6,313,091 B1 | 11/2001 | Wisniewski et al. | |
| 6,489,128 B1 | 12/2002 | Lim et al. | |
| 6,660,482 B1 | 12/2003 | Lim et al. | |
| 6,673,908 B1 | 1/2004 | Stanton, Jr. | |
| 7,932,365 B2 | 4/2011 | Lim et al. | |
| 7,939,282 B2 | 5/2011 | Fast et al. | |
| 9,139,641 B2 | 9/2015 | Lim et al. | |
| 9,572,872 B2* | 2/2017 | Lim ........................ | A61K 38/57 |
| 9,758,570 B2* | 9/2017 | Lim ....................... | C07K 14/811 |
| 2003/0027848 A1 | 2/2003 | Billotte et al. | |
| 2003/0149062 A1 | 8/2003 | Jung et al. | |
| 2003/0190732 A1 | 10/2003 | Josic | |
| 2004/0009212 A1 | 1/2004 | Tsai | |
| 2006/0079670 A1 | 4/2006 | Komatsoulis et al. | |
| 2007/0160594 A1 | 7/2007 | Filvaroff et al. | |
| 2007/0172479 A1 | 7/2007 | Warne et al. | |
| 2007/0297982 A1 | 12/2007 | Lim et al. | |
| 2011/0190194 A1 | 8/2011 | Lim et al. | |
| 2011/0190208 A1 | 8/2011 | kerstrom et al. | |
| 2011/0236381 A1 | 9/2011 | Garantziotis et al. | |
| 2011/0293594 A1 | 12/2011 | Teschner et al. | |
| 2012/0028269 A1 | 2/2012 | Lim et al. | |
| 2012/0053113 A1 | 3/2012 | Bairstow et al. | |
| 2014/0206844 A1 | 7/2014 | Lim | |
| 2015/0361127 A1 | 12/2015 | Lim | |

FOREIGN PATENT DOCUMENTS

| | | |
|---|---|---|
| CN | 101160133 A | 4/2008 |
| EP | 0367090 A1 | 5/1990 |
| EP | 2664337 A1 | 11/2013 |
| JP | H09-503775 A | 4/1997 |
| JP | 2003-40775 A | 2/2003 |
| JP | 2003-292459 A | 10/2003 |
| JP | 2005-531521 A | 10/2005 |
| JP | 2006-520390 A | 9/2006 |
| JP | 2007-515397 A | 6/2007 |
| WO | WO-01/63280 A2 | 8/2001 |
| WO | WO-02/30983 A2 | 4/2002 |
| WO | WO-02/32406 A2 | 4/2002 |
| WO | WO-03/082247 A2 | 10/2003 |
| WO | WO-2004/082615 A2 | 9/2004 |
| WO | WO-2005/030252 A1 | 4/2005 |
| WO | WO-2005/046587 A2 | 5/2005 |
| WO | WO-2005/121163 A2 | 12/2005 |
| WO | WO-2007/038686 A2 | 4/2007 |

(Continued)

OTHER PUBLICATIONS

ProThera Biologics. Inter-alpha Inhibitor Proteins (IAIP). Oct. 2010. Accessed online Apr. 11, 2018 at http://www.ri-bizplan.com/Portals/0/Uploads/Documents/Resources/ProThera.pdf (Year: 2010).*
Ahmed et al., "Inhibition of allergic late airway responses by inhaled heparin-derived oligosaccharides," J Appl Physiol. 88(5):1721-9 (2000).
Ahmed et al., "Prevention of exercise-induced bronchoconstriction by inhaled low-molecular-weight heparin," Am J Respir Crit Care Med. 160(2):576-81 (1999).
Atmani et al., "Role of inter-alpha-inhibitor and its related proteins in urolithiasis. Purification of an inter-alpha-inhibitor related protein from the bovine kidney," Urol Res. 27(1):57-61 (1999).
Bogdan et al., "Tumor necrosis factor-alpha contributes to apoptosis in hippocampal neurons during experimental group B streptococcal meningitis," J Infect Dis. 176(3):693-7 (1997).

(Continued)

*Primary Examiner* — Marcela M Cordero Garcia
(74) *Attorney, Agent, or Firm* — Clark & Elbing LLP

(57) ABSTRACT

The invention relates to methods of treatment of medical conditions (e.g., diseases and injuries) in a mammal (e.g., a human), such as hypoxia/ischemia, burns, and viral infections (e.g., influenza, West Nile virus, and Dengue fever), in adults and in children (e.g., neonates) by administering a composition that includes an IAIP.

19 Claims, 12 Drawing Sheets

(56) References Cited

FOREIGN PATENT DOCUMENTS

| WO | WO-2008/067655 A1 | 6/2008 |
| --- | --- | --- |
| WO | WO-2009/154695 A1 | 12/2009 |
| WO | WO-2010/068308 A1 | 6/2010 |
| WO | WO-2014/039987 A2 | 3/2014 |
| WO | WO-2014/113659 A1 | 7/2014 |

OTHER PUBLICATIONS

Bradding et al., "TNF alpha is localized to nasal mucosal mast cells and is released in acute allergic rhinitis," Clin Exp Allergy. 25(5):406-15 (1995) (Abstract only provided) (1 page).
Brass et al., "Chronic LPS inhalation causes emphysema-like changes in mouse lung that are associated with apoptosis," Am J Respir Cell Mol Biol. 39(5):584-90 (2008).
Burnouf, "Chromatography in plasma fractionation: benefits and future trends," J Chromatogr B Biomed Appl. 664(1):3-15 (1995).
Campo et al., "Molecular-weight-dependent effects of nonanticoagulant heparins on allergic airway responses," J Appl Physiol. 86(2):549-57 (1999).
Carrette et al., "Purification and characterization of pig inter-alpha-inhibitor and its constitutive heavy chains," Biochim Biophys Acta. 1338(1):21-30 (1997).
Cazzola et al., "Emerging anti-inflammatory strategies for COPD," Eur Respir J. 40(3):724-41 (2012).
Communication Pursuant to Article 94(3) EPC in European Patent Application No. 04810367.5, dated Jul. 1, 2013 (5 pages).
Communication Pursuant to Article 94(3) EPC in European Patent Application No. 04810367.5, dated May 23, 2014 (5 pages).
Communication Pursuant to Article 94(3) EPC in European Patent Application No. 09767008.7 dated Oct. 22, 2013 (7 pages).
Communication Pursuant to Article 94(3)EPC for European Patent Application No. 09767008.7, dated Sep. 23, 2014 (6 pages).
Communication Pursuant to Rules 70(2) and 70a(2) EPC for European Patent Application No. 09767008.7, dated Aug. 12, 2011 (1 page).
Daveau et al., "Human inter-alpha-inhibitor family in inflammation: simultaneous synthesis of positive and negative acute-phase proteins," Biochem J. 292(Pt 2):485-92 (1993).
De la Motte et al., "Mononuclear leukocytes bind to specific hyaluronan structures on colon mucosal smooth muscle cells treated with polyinosinic acid:polycytidylic acid: inter-alpha-trypsin inhibitor is crucial to structure and function," Am J Pathol. 163(1):121-33 (2003).
Decision of Refusal for Japanese Patent Application No. 2011-511643, dated Dec. 9, 2014 (4 pages).
Doukas et al., "Aerosolized phosphoinositide 3-kinase gamma/delta inhibitor TG100-115 [3-[2,4-diamino-6-(3-hydroxyphenyl)pteridin-7-yl]phenol] as a therapeutic candidate for asthma and chronic obstructive pulmonary disease," J Pharmacol Exp Ther. 328(3):758-65 (2009).
Enghild et al., "Analysis of inter-alpha-trypsin inhibitor and a novel trypsin inhibitor, pre-alpha-trypsin inhibitor, from human plasma. Polypeptide chain stoichiometry and assembly by glycan," J Biol Chem. 264(27):15975-81 (1989).
English Translation of Notification of Reason for Refusal in Japanese Patent Application No. 2011-511643, dated Nov. 12, 2013 (7 pages).
English Translation of the Notification of Reason for Refusal for Japanese Patent Application No. 2015-080358, dated Mar. 30, 2016 (5 pages).
EPO Communication pursuant to Rule 112(1) EPC for European Patent Application No. 09767008.7, dated Aug. 11, 2015 (3 pages).
Examination Report for Australian Patent Application No. 2009260822, dated Dec. 19, 2014 (4 pages).
Extended European Search Report and Written Opinion for European Patent Application No. 09767008.7, dated Jul. 26, 2011 (7 pages).
Extended European Search Report for European Application No. EP 09767008.7, dated Jul. 26, 2011 (7 pages).
Feldmann et al., "Lasker Clinical Medical Research Award. TNF defined as a therapeutic target for rheumatoid arthritis and other autoimmune diseases," Nat Med. 9(10):1245-50, 1433 (2003).
First Office Action for Chinese Patent Application No. 200980129119.6, dated Apr. 7, 2013 (31 pages).
Fourth Office Action for Chinese Patent Application No. 200980129119.6, dated Jul. 30, 2015 (19 pages).
Garantziotis et al., "Inter-alpha-trypsin inhibitor attenuates complement activation and complement-induced lung injury," J Immunol. 179(6):4187-92 (2007) (7 pages).
Hamm et al., "Frequent expression loss of Inter-alpha-trypsin inhibitor heavy chain (ITIH) genes in multiple human solid tumors: a systematic expression analysis," BMC Cancer. 8:25 (2008) (15 pages).
Hoffer et al., "Improved virus safety and purity of a chromatographically produced Factor IX concentrate by nanofiltration," J Chromatogr B Biomed Appl. 669(2):187-96 (1995).
International Preliminary Report on Patentability and Written Opinion of the International Searching Authority for International Application No. PCT/US2009/003291, dated Nov. 30, 2010 (6 pages).
International Preliminary Report on Patentability and Written Opinion of the International Searching Authority for International Application No. PCT/US2013/058791, dated Jun. 11, 2015 (7 pages).
International Preliminary Report on Patentability and Written Opinion of the International Searching Authority for International Application No. PCT/US2014/012033, dated Jul. 21, 2015 (10 pages).
International Search Report and Written Opinion for International Application No. PCT/US2014/012033, dated May 27, 2014 (14 pages).
International Search Report and Written Opinion for International Patent Application No. PCT/US2013/058791, dated Jan. 10, 2014 (11 pages).
International Search Report for International Application No. PCT/US2004/036848, dated Nov. 4, 2005 (5 pages).
International Search Report for International Application No. PCT/US2009/003291, dated Aug. 24, 2009 (2 pages).
Ito et al., "A pilot randomized trial of a human anti-interleukin-6 receptor monoclonal antibody in active Crohn's disease," Gastroenterology. 126(4):989-96 (2004).
Iwasaki et al., "TNF-alpha contributes to the development of allergic rhinitis in mice," J Allergy Clin Immunol. 112(1):134-40 (2003).
Josic et al., "Proteomic characterization of inter-alpha inhibitor proteins from human plasma," Proteomics. 6(9):2874-85 (2006).
Katoh et al., "Galectin-9 inhibits CD44-hyaluronan interaction and suppresses a murine model of allergic asthma," Am J Respir Crit Care Med. 176(1):27-35 (2007).
Katz, "Advances in the medical therapy of inflammatory bowel disease," Curr Opin Gastroenterol. 18(4):435-40 (2002).
Koraka et al., "Plasma levels of inter-alpha inhibitor proteins in children with acute Dengue virus infection," PLoS One. 5(4):e9967 (2010) (4 pages).
Kricka, "Human anti-animal antibody interferences in immunological assays," Clin Chem. 45(7):942-956 (1999).
Lim et al., "Affinity purification and enzymatic cleavage of inter-alpha inhibitor proteins using antibody and elastase immobilized on CIM monolithic disks," J Chromatogr A. 1065(1):39-43 (2005).
Lim et al., "Correlation between mortality and the levels of inter-alpha inhibitors in the plasma of patients with severe sepsis," J Infect Dis. 188(6):919-26 (2003).
Lim, "Inter-alpha inhibitors: From laboratory to market," <http://www.brownenterpriseforum.org/matriarch/documents/Lim.pdf>, retrieved Jul. 13, 2011 (6 pages).
Ljung et al., "Infliximab in inflammatory bowel disease: clinical outcome in a population based cohort from Stockholm County," Gut. 53(6):849-53 (2004).
Martinez-Salas et al., "Inhibition of allergic airway responses by inhaled low-molecular-weight heparins: molecular-weight dependence," J Appl Physiol. 84(1):222-8 (1998).

(56) References Cited

OTHER PUBLICATIONS

McCann et al., "Evaluation of expanded bed adsorption chromatography for extraction of prothrombin complex from Cohn Supernatant I," Biologicals. 36(4):227-233 (2008).
MEGA- and GIGA preps of cosmid-, BAC-, PAC, YAC-, and P1-DNA with JETSTAR 2.0, Sep. 2005 (6 pages).
Michalski et al., "Preparation and properties of a therapeutic inter-alpha-trypsin inhibitor concentrate from human plasma," Vox Sang. 67(4):329-36 (1994).
Mihara et al., "IL-6/IL-6 receptor system and its role in physiological and pathological conditions," Clin Sci (Lond). 122(4):143-59 (2012).
Mizon et al., "Human pre-alpha-inhibitor: isolation from a by-product of industrial scale plasma fractionation and structural analysis of its H3 heavy chain," J Chromatogr B Biomed Sci Appl. 692(2):281-91 (1997).
Mo et al., "Anti-tumor necrosis factor-alpha treatment reduces allergic responses in an allergic rhinitis mouse model," Allergy. 66(2):279-86 (2011).
Molinari et al., "Inhibition of antigen-induced airway hyperresponsiveness by ultralow molecular-weight heparin," Am J Respir Crit Care Med. 157(3 Pt 1):887-93 (1998).
Notice of Preliminary Rejection for Korean Patent Application No. 10-2010-7029406, dated Oct. 30, 2015 (14 pages).
Odum, "Inter-alpha-trypsin inhibitor and pre-alpha-trypsin inhibitor in health and disease. Determination by immunoelectrophoresis and immunoblotting," Biol Chem Hoppe Seyler. 371(12):1153-8 (1990).
Office Action for Canadian Patent Application No. 2544816, dated Dec. 30, 2013 (4 pages).
Office Action for Canadian Patent Application No. 2544816, dated Mar. 1, 2012 (7 pages).
Office Action for Canadian Patent Application No. 2544816, dated Oct. 20, 2014 (6 pages).
Office Action for Canadian Patent Application No. 2726281, dated Jun. 30, 2015 (9 pages).
Opal et al., "Inter-alpha-inhibitor proteins are endogenous furin inhibitors and provide protection against experimental anthrax intoxication," Infect Immun. 73(8):5101-5 (2005).
Opal et al., "Longitudinal studies of inter-alpha inhibitor proteins in severely septic patients: a potential clinical marker and mediator of severe sepsis," Crit Care Med. 35(2):387-92 (2007).
Partial Supplementary European Search Report for European Application No. 14740523.7, dated Jun. 8, 2016 (7 pages).
Raoust et al., "Pseudomonas aeruginosa LPS or flagellin are sufficient to activate TLR-dependent signaling in murine alveolar macrophages and airway epithelial cells," PLoS One. 4(10):e7259 (2009) (9 pages).
Rutgeerts et al., "Optimizing anti-TNF treatment in inflammatory bowel disease," Gastroenterology. 126(6):1593-610 (2004).
Salier et al., "Inter-alpha-trypsin-inhibitor (ITI): use of immunoadsorbents for preparation of anti-ITI antiserum, ITI-free human serum and purified ITI," J Immunol Methods. 47(2):239-48 (1981).
Salier et al., "Purification of the human serum inter-alpha-trypsin inhibitor by zinc chelate and hydrophobic interaction chromatographies," Anal Biochem. 109(2):273-83 (1980).
Salier et al., "The inter-alpha-inhibitor family: from structure to regulation," Biochem J. 315(Pt 1):1-9 (1996).
Sanon et al., "Peripheral arterial ischemic events in cancer patients," Vasc Med. 16(2):119-30 (2011).
Saukkonen et al., "The role of cytokines in the generation of inflammation and tissue damage in experimental gram-positive meningitis," J Exp Med. 171(2):439-48 (1990).
Second Office Action for Chinese Patent Application No. 200980129119.6, dated Feb. 20, 2014 (19 pages).
Second Office Action for Chinese Patent Application No. 201210460374.2, dated Aug. 22, 2014 (11 pages).
Sin et al., "Chronic obstructive pulmonary disease as a risk factor for cardiovascular morbidity and mortality," Proc Am Thorac Soc. 2(1):8-11 (2005).
Singh et al., "Inter-alpha inhibitor protein administration improves survival from neonatal sepsis in mice," Pediatr Res. 68(3):242-7 (2010).
Su et al., "Role of CFTR expressed by neutrophils in modulating acute lung inflammation and injury in mice," Inflamm Res. 60(7):619-32 (2011).
Supplementary European Search Report for European Patent Application No. 04810367, dated Jan. 18, 2010 (7 pages).
Sykes et al., "Treatment of severe autoimmune disease by stem-cell transplantation," Nature. 435(7042):620-7 (2005).
Takeuchi et al., "Baseline tumour necrosis factor alpha levels predict the necessity for dose escalation of infliximab therapy in patients with rheumatoid arthritis," Ann Rheum Dis. 70(7):1208-15 (2011) (8 pages).
Tanaka et al., "Targeting interleukin-6: all the way to treat autoimmune and inflammatory diseases," Int J Biol Sci. 8(9):1227-36 (2012).
Tarner et al., "Treatment of autoimmune disease by adoptive cellular gene therapy," Ann NY Acad Sci. 998:512-9 (2003).
Third Office Action for Chinese Patent Application No. 200980129119.6, dated Nov. 15, 2014 (21 pages).
Triantaphyllopoulos et al., "A model of chronic inflammation and pulmonary emphysema after multiple ozone exposures in mice," Am J Physiol Lung Cell Mol Physiol. 300(5):L691-700 (2011).
Van Heel et al., "Inflammatory bowel disease is associated with a TNF polymorphism that affects an interaction between the OCT1 and NF(-kappa)B transcription factors," Hum Mol Genet. 11(11):1281-9 (2002).
Verhein et al., "IL-1 receptors mediate persistent, but not acute, airway hyperreactivity to ozone in guinea pigs," Am J Respir Cell Mol Biol. 39(6):730-8 (2008).
Wu et al., "Delayed administration of human inter-alpha inhibitor proteins reduces mortality in sepsis," Crit Care Med. 32(8):1747-52 (2004).
Yang et al., "Administration of human inter-alpha-inhibitors maintains hemodynamic stability and improves survival during sepsis," Crit Care Med. 30(3):617-22 (2002).
Zhuo et al., "Defect in SHAP-hyaluronan complex causes severe female infertility. A study by inactivation of the bikunin gene in mice," J Biol Chem. 276(11):7693-6 (2001) (5 pages).
Zosky et al., "Animal models of asthma," Clin Exp Allergy. 37(7):973-88 (2007).
Examination Report for Australian Patent Application No. 2009260822, dated Aug. 23, 2016 (3 pages).
Office Action for Canadian Patent Application No. 2726281, dated Aug. 10, 2016 (4 pages).
Communication Pursuant to Article 94(3) EPC in European Patent Application No. 09767008.7, dated Apr. 28, 2016 (7 pages).
Communication Pursuant to Article 94(3) and Rule 71(1) EPC in European Patent Application No. 04810367.5, dated Jun. 4, 2012 (2 pages).
Bove, "Anaphylactic reaction to purified anti-hemophilic factor concentrate," Transfusion 28(6):603 (1988).

* cited by examiner

TREATMENT OF DISEASE USING INTER-ALPHA INHIBITOR PROTEINS

BACKGROUND OF THE INVENTION

Inter alpha inhibitor proteins (IAIPs) are a family of structurally related proteins found in mammalian plasma in relatively high concentrations. IAIPs play important roles in inflammation as part of innate immunity, wound healing, and cancer metastasis (A1-A3). The major forms found in human plasma are inter-alpha inhibitor (IaI), which consists of two heavy chains (H1 and H2) and a single light chain, and pre-alpha inhibitor (PaI), which consists of one heavy (H3) and one light chain. The light chain (bikunin) is known to inhibit several serine proteases, such as trypsin, human leukocyte elastase, plasmin, and cathepsin G (A1, A4). The liver is the major site of synthesis of the heavy and light chains of IAIP (A3, A5). The high levels of circulating IAIPs normally found in plasma of adults and newborns, and even in prematurely born infants, suggest that these proteins are important. Moreover, complete absence of IAIPs has not been reported in humans (A1), suggesting that these proteins have significant functions in human biology. In premature infants, IAIPs have recently been shown to decrease in association with sepsis and necrotizing enterocolitis (NEC) (A6-A8). In addition, both disorders are associated with increased incidences of brain damage in premature infants (A9, A10).

The decreased plasma levels found in septic patients and concomitant increases of IAIP-related fragments in the urine suggest that these proteins are "consumed" and rapidly cleared from the systemic circulation during sepsis (A2, A11, A12). Although the physiological functions of IAIPs remain to be established, current findings suggest that these molecules are part of innate immunity and play a critical role during inflammation. IAIPs have unique immunomodulatory effects by reducing TNF-α during systemic inflammation and augmenting anti-inflammatory IL-10 during sepsis in neonatal rats (A2, A13, A14). The urinary trypsin inhibitor or bikunin has also been suggested to be effective in inhibiting premature delivery most likely by suppressing cytokines and other inflammatory mediators (A15-A19). In addition, recent observations demonstrate that IAIPs attenuate complement activation through the classical and alternative pathways, inhibit complement-dependent phagocytosis in vitro, and reduce complement-dependent lung injury in vivo (A20). These functions potentially provide mechanistic explanations for its beneficial effects in systemic inflammation and sepsis and suggest that IAIPs could play an important role in inflammation-related disorders during the perinatal period.

The function of the choroid plexus (CP) and its product cerebral spinal fluid (CSF) has been thought of as providing physical protection to the brain and facilitating the removal of brain metabolites through the drainage of CSF. However, more recent studies suggest that the choroid plexus-cerebral spinal fluid system plays a much more active role in the development, homeostasis, and repair of the central nervous system (CNS) (A39-A41). CP is a highly specialized tissue, strategically positioned within the ventricles to provide the CNS with a variety of biologically active growth factors that are essential for normal brain development (A40-A42). These factors include a number of neurotrophic and angiogenic factors, such as transforming growth factor-α and -β superfamily, insulin-like growth factor, and vascular endothelial growth factor (VEGF), (43-52) and chemo repellents, such as semaphoring 3f and slit protein (A53, A54) that appear to be involved in neurogenesis and axonal guidance during development of CNS, in response to brain injury, and possibly in the subsequent repair processes. Previous studies reported that during development in many species including human premature infants, cerebral spinal fluid has very high protein concentrations, which are most likely important for brain development (A55-A58). Therefore, proteins found in cerebral spinal fluid most likely influence brain development and responses to injury. Although IAIPs are most likely immunomodulatory compounds, their levels have not been previously reported in CSF in any species during development.

Information is also very limited regarding the distribution of these IAIP molecules among different organs, including brain. In humans, IAIPs were detected in cerebrum, cerebellum, lungs, kidney, liver, colon, skin, and testes (A22). Information is not available regarding the expression of IAIPs in the brain or somatic organs during normal development.

Tissue ischemia, e.g., persistent restriction of blood supply to a tissue, can impair tissue function and result in tissue and organ damage. Tissue ischemia in critical organ systems or body parts, for example, heart, brain, kidneys, skin, limbs, or gastrointestinal tract, contributes significantly to human morbidity and mortality, and thus there is a continuing need for therapeutic strategies for treating or protecting the affected tissues.

SUMMARY OF THE INVENTION

The present invention is based, in part, on our discovery that IAIPs can be administered (e.g., with a pharmaceutically acceptable carrier) to provide neuroprotection and to treat tissue ischemia (e.g., in the brain), including tissue ischemia associated with a disorder, trauma or a congenital defect. The tissue ischemia encompassed by the methods of the invention can stem from any of a wide range of medical conditions that result in the acute, persistent, or recurring restriction of blood supply to the tissue, for example, disorders such as peripheral artery disease, type 1 or type 2 diabetes, atherosclerotic cardiovascular disease, intermittent claudication (which can manifest as cramping pain in the extremities due to inadequate blood supply), critical limb ischemic disease, stroke, myocardial infarction, inflammatory bowel disease, and peripheral neuropathy; traumatic injuries such as wounds, burns, lacerations, contusions, bone fractures, infections, or surgical procedures; congenital malformations such as hernias, cardiac defects and gastrointestinal defects. Thus, tissue ischemia can occur in a variety of tissue types including, for example, skeletal muscle, smooth muscle, cardiac muscle, neuronal tissue (e.g., the brain), skin, mesenchymal tissue, connective tissue, gastrointestinal tissue and bone.

The present invention provides, in a first aspect, methods of treating, reducing, or inhibiting ischemia or a condition resulting from ischemia in a patient in need thereof. These methods include administering to the patient a composition including inter-alpha inhibitor (IaI) and/or pre-alpha inhibitor (PaI). In some embodiments, the method treats, reduces, or inhibits ischemia. In some embodiments, the method treats, reduces, or inhibits a condition resulting from ischemia. In some embodiments, the ischemia may be ischemia/reperfusion injury, hypoxic ischemia, or hypoxic ischemia encephalopathy. In some embodiments, the condition resulting from ischemia may be selected from cerebral palsy (CP2), mental impairment, brain damage, paralysis, and neurological morbidity. In some embodiments, the condition resulting from ischemia may be damage or loss of white matter, white matter demyelination, polymorphonuclear neutrophil infiltration, cerebral cortical injury, inflammation, endothelial activation, cell death, neuronal apoptosis, inhibition of growth, inhibition of development, decreased MBP, altered cellularity of GFAP positive astrocytes, neuronal apoptosis, decreased infarct volume, decreased levels of IαIp, increased plasmin activity, increased activity of metalloproteinases, increased levels of caspase-3, increased levels of Parp1, or increased levels of one or more of the cytokines IL-13, TNF-α, INF-α, IL-6, IL-10, INF-γ, and IL-8. In some embodiments, a method of the present invention may reduce the likelihood or risk of mortality.

In any of the present methods of treating, reducing, or inhibiting ischemia or a condition resulting from ischemia, the ischemia may be acute ischemia. The acute ischemia may be recurring. The ischemia may be persistent. In any of the above embodiments, the methods of the present invention may reduce the severity of ischemia or a condition resulting from ischemia or delay the onset or progression of ischemia or a condition resulting from ischemia. In certain embodiments, the ischemia may result from a medical condition, a traumatic injury, or a congenital malformation. Preferably, the medical condition may be selected from peripheral artery disease, type 1 or type 2 diabetes, atherosclerotic cardiovascular disease, intermittent claudication, critical limb ischemic disease, stroke, cancer, myocardial infarction, inflammatory bowel disease, carotid occlusion, umbilical cord occlusion, low birth-weight, premature birth, pulmonary insufficiency, peripheral neuropathy, and bleeding (hemorrhagic), the traumatic injury may be selected from wound, burn, laceration, contusion, bone fracture, infection, and surgical procedure, and the congenital malformation may be selected from hernia, cardiac defect, and gastrointestinal defect. In particular embodiments, the ischemia may result from ischemic hemorrhagic stroke.

In any of the above embodiments, the ischemia may occur in a tissue or cell type selected from skeletal muscle, smooth muscle, cardiac muscle, connective tissue, mesenchymal tissue, gastrointestinal tissue, placenta, liver, heart, kidney, intestine, lung, colon, kidney, bladder, testes, skin, bone, brain, cerebral cortex, choroid plexus, cerebrum, cerebellum, neurons, astrocytes, and meningeal cells. The ischemia may be brain ischemia. The brain ischemia may be ischemia of neurons, astrocytes, or meningeal cells of the brain. The brain ischemia may be ischemia of the cerebral cortex. The brain ischemia may be the result of a stroke.

In any of the above embodiments, the patient may be at risk of experiencing the ischemia or condition resulting from ischemia. The methods of the present invention may reduce the severity of the ischemia or condition resulting from ischemia in the patient. The methods of the present invention may reduce the likelihood of manifesting, delay the onset of, or delay the progression of, the ischemia or condition resulting from ischemia in the patient. The patient may be a fetus, an infant, or an adult. The fetus may be at risk of premature birth, very low birth-weight, and/or pulmonary insufficiency. The infant may be born prematurely, born with a very low birth-weight, have or be at risk of pulmonary insufficiency, and/or have or be at risk of having an immature vasculature. The patient may have experienced, or be at risk of, ischemia resulting from umbilical cord occlusion. The patient may have experienced, or be at risk of, ischemia resulting from carotid occlusion.

In any of the above embodiments, the patient may be human. In any of the above embodiments, the patient may have experienced ischemia or a condition resulting from ischemia prior to the administration of the composition including inter-alpha inhibitor (IaI) and/or pre-alpha inhibitor (PaI). In certain embodiments, the patient may have low levels of brain IαIp. In any of the above embodiments, the composition may be administered at a dosage of 1 mg/kg body weight to 50 mg/kg body weight. In any of the above embodiments, the composition may be administered at a dosage ranging from 50 mg/dose to 1000 mg/dose. The composition may be administered every 4 to 120 hours. The composition may include a pharmaceutically acceptable excipient, diluent, or carrier. The composition may be a solid. The solid may be a tablet, capsule, or suppository. The composition may be a liquid. The composition may be formulated for inhalation, insufflation, nebulization, injection, oral, rectal, topical, or intraperitoneal administration, intracerebral injection, intravenous delivery, intraarterial delivery, or fetal infusion. In some embodiments, administration of the composition results in a decrease in or downregulation of one or more cytokines. The cytokines may be pro-inflammatory cytokines. Any of the above cytokines may be intravascular cytokines. Any of the above cytokines may be endothelial-derived cytokines. Any of the above cytokines may be generated during the ischemia or as a result of a condition resulting from ischemia.

In any of the above embodiments, administration of the composition may result in a decrease in free radicals. In any of the above embodiments, administration of the composition may result in a decrease in TNF-α. In any of the above embodiments, the half-life of the composition may be 12 to 18 hours.

A further aspect of the invention provides methods of providing neuroprotection to a patient in need thereof, the method including administering to the patient a composition including inter-alpha inhibitor (IaI) and/or pre-alpha inhibitor (PaI).

In another aspect, the invention provides methods of treating a wound in a patient in need thereof, the method including administering to the patient a composition including inter-alpha inhibitor (IaI) and/or pre-alpha inhibitor (PaI). The wound may be a burn.

In yet another aspect, the invention provides methods of treating or preventing a viral infection in a patient in need thereof, the method including administering to the patient a composition including inter-alpha inhibitor (IaI) and/or pre-alpha inhibitor (PaI). The viral infection may be influenza, Dengue fever, or West Nile fever. The viral infection may be H1N1 flu or bird flu.

A further aspect of the present invention provides methods of treating or preventing cancer metastasis in a patient in need thereof, the method including administering to the patient a composition including inter-alpha inhibitor (IaI) and/or pre-alpha inhibitor (PaI).

The term "pharmaceutically acceptable carrier or adjuvant" refers to a carrier or adjuvant that may be administered to a subject, together with a composition of this invention, and which does not destroy the pharmacological activity thereof and is nontoxic when administered in doses sufficient to deliver a therapeutic amount of the composition.

BRIEF DESCRIPTION OF THE DRAWINGS

FIG. 4A shows sham operated normal fetus. The cortex shows normal cerebral cortical tissue and the white matter shows normal white matter with blue staining. FIG. 4B shows a fetus exposed to hypoxia ischemia with a thin ribbon like cerebral cortex and a dramatic loss of white matter. FIG. 4C shows an animal that was treated with IAIPs IV 4 mg/kg 15 min and 24 and 48 hours after carotid occlusion. There is remarkable neuroprotection of both white matter and cerebral cortex. This animal was treated the same as B but looks similar to the normal animal in A.

FIG. 9A shows expression of the 125 kDa IAIP and FIG. 9B shows expression of the 250 kDa IAIP.

DETAILED DESCRIPTION OF THE INVENTION

Figure 1:
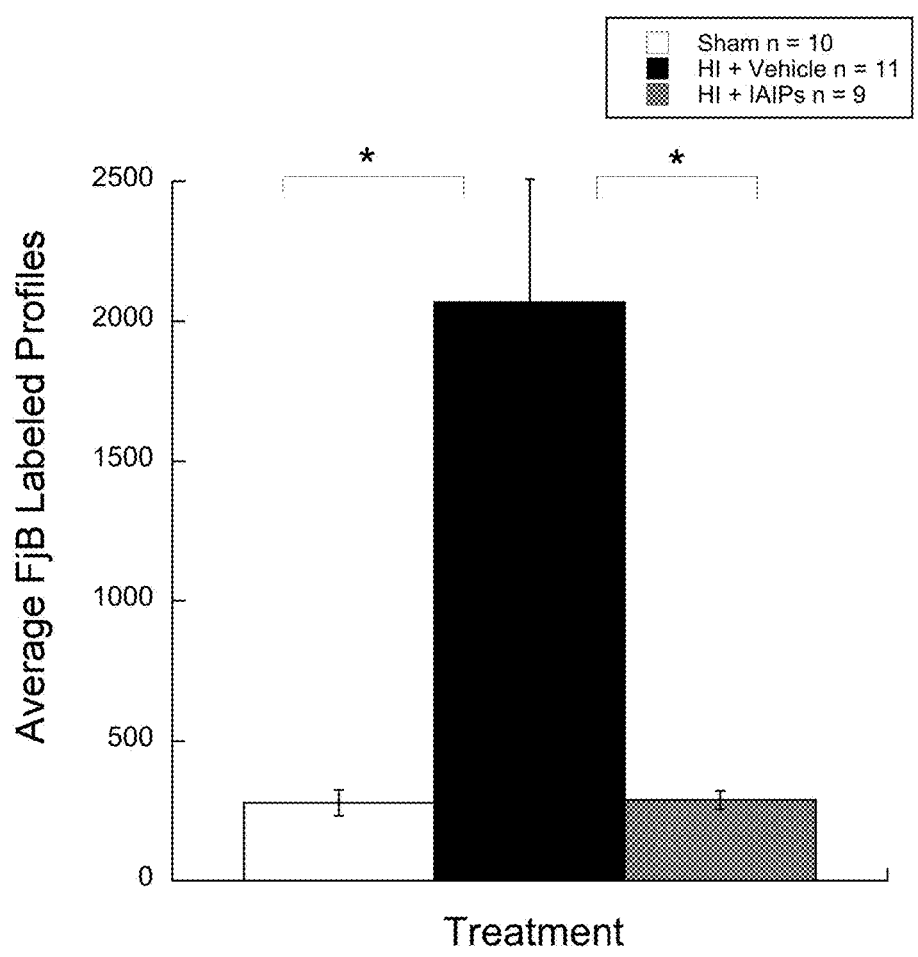
FIG. 1 is a graph showing average Fluoro-Jade B (FjB) staining in rats following sham treatment, placebo treatment, and treatment with IAIP. Significant increase in total FjB labeled cells in vehicle HI animals compared to sham and IAIP-treated animals is shown. *$p<0.05$.

We have discovered methods for the treatment of tissue ischemia, in particular ischemia of the brain, using IAIPs. These methods can be applied to, and are expected to benefit subjects having any of a variety of medical conditions that can give rise to tissue ischemia. The methods are based, inter alia, on the inventor's discovery that administration of IAIPs or a pharmaceutical composition comprising IAIPs to a subject having or likely to develop tissue ischemia.

Compositions

The pharmaceutically acceptable compositions of the invention include IAIPs in dosages known in the art (see, e.g., U.S. Pat. No. 7,932,365 and US 2009/0190194, each of which is incorporated herein by reference in its entirety).

For example, compositions of the invention can be administered in a dosage ranging from about 1 to 50 mg/kg of body weight, preferably dosages between 500 mg and 1000 mg/dose, every 4 to 120 hours, or as needed.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, for example, 0.1 to about 1000 mg of the active ingredient of the present invention.

The tablets or pills of the present invention can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compounds and compositions of the present invention can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described herein and/ or known in the art. In some embodiments, the compositions are administered by the oral or nasal respiratory route for local or systemic effect. Compositions in can be nebulized by use of inert gases. Nebulized solutions may be breathed directly from the nebulizing device or the nebulizing device can be attached to a face masks tent, or intermittent positive pressure breathing machine. Solution, suspension, or powder compositions can be administered orally or nasally from devices which deliver the formulation in an appropriate manner.

The compositions administered to a patient can be in the form of one or more of the pharmaceutical compositions described above. These compositions can be sterilized by conventional sterilization techniques or may be sterile filtered. Aqueous solutions can be packaged for use as is, or lyophilized, the lyophilized preparation being combined with a sterile aqueous carrier prior to administration. The pH of the compound preparations typically will be between about 3 and 11, for example, between about 5 to 9, between 6 and 7, or between 7 and 8. It will be understood that use of certain of the foregoing excipients, carriers, or stabilizers will result in the formation of pharmaceutical salts.

The proportion or concentration of a compound of the invention in a pharmaceutical composition can vary depending upon a number of factors including dosage, chemical characteristics (e.g., hydrophobicity), and the route of administration. For example, the compounds of the invention can be provided in an aqueous physiological buffer solution containing about 0.1 to about 10% w/v of the compound for parenteral adminstration.

Pharmaceutically acceptable carriers, adjuvants and vehicles that may be used in the pharmaceutical compositions of this invention include, but are not limited to, ion exchangers, alumina, aluminum stearate, lecithin, self-emulsifying drug delivery systems (SEDDS) such as dα-tocopherol polyethyleneglycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as α-, β-, and γ-cyclodextrin, or chemically modified derivatives such as hydroxyalkylcyclodextrins, including 2- and 3-hydroxypropyl-β-cyclodextrins, or other solubilized derivatives may also be advantageously used to enhance delivery of compositions described herein.

The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated composition or its delivery form. The term parenteral as used herein includes subcutaneous, intracutaneous, intravenous, intramuscular, intraarticular, intraarterial, intrasynovial, intrasternal, intrathecal, intralesional and intracranial injection or infusion techniques. Suitable methods of administration may be as a tablet, capsule, or by intravenous injection. Injectable forms of administration are particularly preferred.

The pharmaceutical compositions may be in the form of a sterile injectable preparation, for example, as a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, or carboxymethyl cellulose or similar dispersing agents which are commonly used in the formulation of pharmaceutically acceptable dosage forms such as emulsions and or suspensions. Other commonly used surfactants such as Tweens or Spans and/or other similar emulsifying agents or bioavailability enhancers which are commonly used in the manufacture of pharmaceutically acceptable solid, liquid, or other dosage forms may also be used for the purposes of formulation.

The pharmaceutical compositions of this invention may be orally administered in any orally acceptable dosage form including, but not limited to, capsules, tablets, emulsions and aqueous suspensions, dispersions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions and/or emulsions are administered orally, the active ingredient may be suspended or dissolved in an oily phase is combined with emulsifying and/or suspending agents. If desired, certain sweetening and/or flavoring and/or coloring agents may be added.

The pharmaceutical compositions of this invention may also be administered in the form of suppositories for rectal administration. These compositions can be prepared by mixing a composition of this invention with a suitable non-irritating excipient which is solid at room temperature but liquid at the rectal temperature and therefore will melt in the rectum to release the active components. Such materials include, but are not limited to, cocoa butter, beeswax and polyethylene glycols.

Topical administration of the pharmaceutical compositions of this invention is useful when the desired treatment involves areas or organs readily accessible by topical application. For application topically to the skin, the pharmaceutical composition should be formulated with a suitable ointment containing the active components suspended or dissolved in a carrier. Carriers for topical administration of the compositions of this invention include, but are not limited to, mineral oil, liquid petroleum, white petroleum, propylene glycol, polyoxyethylene polyoxypropylene composition, emulsifying wax and water. Alternatively, the pharmaceutical composition can be formulated with a suitable lotion or cream containing the active composition suspended or dissolved in a carrier with suitable emulsifying agents. Suitable carriers include, but are not limited to, mineral oil, sorbitan monostearate, polysorbate 60, cetyl esters wax, cetearyl alcohol, 2-octyldodecanol, benzyl alcohol and water. The pharmaceutical compositions of this invention may also be topically applied to the lower intestinal tract by rectal suppository formulation or in a suitable enema formulation. Topically-transdermal patches are also included in this invention.

The pharmaceutical compositions of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

Treatment of Disease Using IAIPs

Tissue Ischemia

Tissue ischemia is associated with a wide range of medical conditions that result in partial, substantially complete or complete reduction of blood flow to a body part or tissue comprising a body part and may be the result of disease, injury, or of an unknown cause, and may be influenced by one's genetic constitution. Regardless of the medical condition leading to tissue ischemia, a patient who has or is likely to develop tissue ischemia is a candidate for treatment with the pharmaceutically acceptable IAIP compositions described herein. Treatment can completely or partially abolish some or all of the signs and symptoms of tissue ischemia, decrease the severity of the symptoms, delay their onset, or lessen the progression or severity of subsequently developed symptoms.

IAIPs are important in inflammatory responses during the perinatal period as evidenced by our previous findings that they are dramatically decreased in response to sepsis and NEC in premature infants (A13, A15-A19), (A7, A8), and are important in ischemic and inflammatory related brain and somatic organ damage in adult rats (A31, A32). Therefore, given the potential importance of these molecules in perinatal period during inflammatory states, and the fact that we have recently shown that they are present in high levels in the normal brain and in somatic organs during development and that damage is associated with decreases in IAIPs in ischemia related disorder in adult subjects, we believe these molecules represent endogenous immuno-protective molecules in most organs during development. Furthermore, we hypothesize that administration of these molecules most likely will prove to have great therapeutic potential during the perinatal period and in adults with stroke.

In addition, data suggests that IAIP plays a role in down-regulation of systemic inflammatory cytokines, including a systemic effect measured in the brain. IAIPs are believed to function in a unique manner at the blood-brain barrier ("BBB"), and have a positive effect on the suppression of free radicals. IAIP also delivers an additional advantage over bikunin, due to significantly increased half-life. IAIP half-life is in the range of 12-18 hours, while bikunin half-life is in the range of 3-8 minutes. Therefore, systemically delivered, e.g., IV delivered, IAIP has the benefit of system-wide distribution, and steady time-release of Light Chain proteins over a significantly increased time. In other words, IAIP acts as a transport agent and release mechanism modulator to more effectively deliver a therapeutic benefit over a longer period of time, and over a broader systemic area. As IAIP separates into the heavy and light chain components that make up IAIP, a complementary series of therapeutic benefits ensues, over a longer period of time than any previous therapy.

Summary of Benefits of Treatment According to the Invention

IAIP as a biomarker for brain injury: IAIP levels in the brain, or "Brain IAIP" decreases markedly after exposure of the brain to hypoxic ischemia. Data show that Brain IAIP is directly correlated to brain injury due to hypoxic ischemia. Replacing IAIP through IV delivery post hypoxic ischemia has the benefit of replacing the IAIP and increasing systemic, IAIP levels and brain IAIP levels. Furthermore, data show that IAIP is an accurate biomarker for brain injury.

Figure 4A:
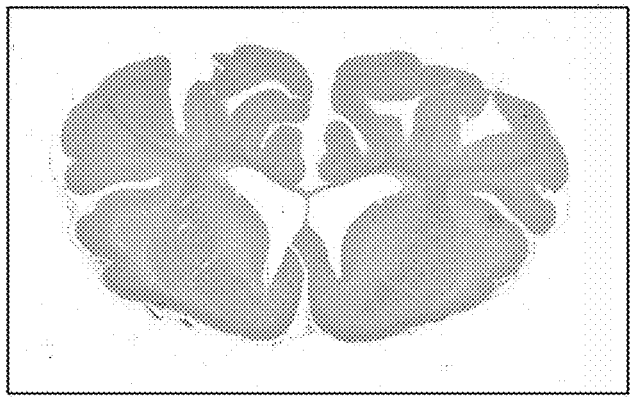
FIGS. 4A-4C are photographs of hematoxylin and eosin and Luxol fast blue stained sections of fetal sheep brain. The hematoxylin and eosin stains the cerebral cortical tissue and the Luxol fast blue stains the white matter. Infants with CP2 have white matter damage.
Figure 4B:
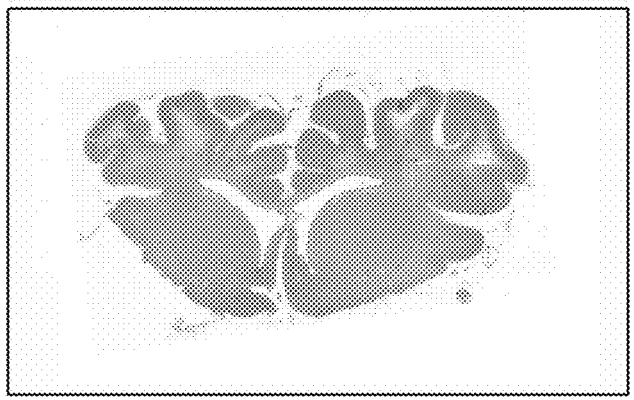
Figure 4C:
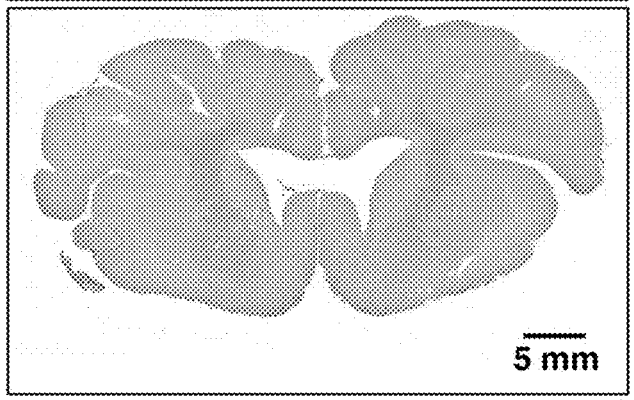
Figure 6:
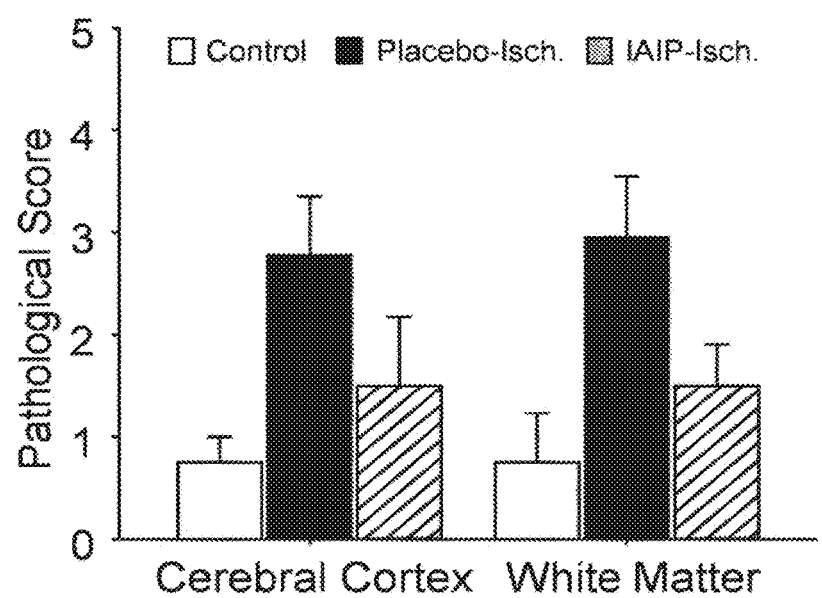
FIG. 6 is a graph showing the pathological score of brain tissue that has been treated with a control under normal conditions, a placebo under ischemic conditions, and with IAIP under ischemic conditions. The pathological scoring was performed by a pathologist who did not know the treatment categories of the fetal sheep. The sham operated control sheep is shown by the control bars for the cerebral cortex and white matter. The hypoxic ischemic sheep are shown by the black bars and the hatched bars are the hypoxic ischemic sheep that were treated with IAIPs after ischemia as described above. Note that there is about a 50% reduction in injury to the cerebral cortex and white matter. This is important because damage to the cerebral cortex results in mental retardation and to white matter in CP2.

IAIP is effective as a neuroprotectant following hypoxic ischemia or stroke. We hypothesize that replacing IAIP through IV delivery after hypoxic ischemia or stroke will most likely increase systemic IAIP levels. We have shown that IV administration of IV IAIP to fetal sheep markedly decrease brain injury in the perinatal brain (FIG. 4A-4C), and reduces Pathological Scoring of uninjured tissue as measured in Cerebral Cortex and White Matter by a pathologist who was not aware of the treatment of the animals (FIG. 6).

IAIP levels are very high in the Cerebral Spinal Fluid ("CSF") in the fetus, and IAIP levels drop precipitously upon birth. This endogenous high level of IAIP present in fetal CSF suggests that IAIPs are critical in the development of the prenatal brain. Adults do not have any IAIP present in their CSF, as measured by Western Blot testing. This early data is significant as it underscores the unique and significant correlation between IAIP and fetal brain development.

IAIP acts a positive mediator for Ischemic Reperfusion Injury ("IR"). It has been shown that hypoxic ischemia and/or stroke lead to cerebral palsy (CP2), and mental retardation. One understood physiological contributor to this clinical issue is IR. IAIP has been shown to reduce and mitigate the deleterious effects of ischemic IR.

Neuroprotection and Treatment of Hypoxic Ischemia in Neonates

The only approved treatment for neonatal hypoxia-ischemia is hypothermia, which is only partially protective. Additional treatments that provide greater neuroprotection are vitally needed for treating this disorder in neonates. Hypoxia-ischemia at birth results in a great burden lifelong burden to the individual and society. There is only one treatment for stroke in adult patients and it has a very limited scope as it must be used within 4.5 hours of the development of stroke. There is not treatment for stroke in newborns. This is important as the incidence of stroke in the newborn is the same as in adult patients.

While much of the data has been heretofore focused on animal studies, to include sheep studies, it must be noted that the only study measuring efficacious treatment for human infants was performed using the same sheep model that the inventors used.[1]

Sepsis and NEC-related decreases in IAIPs could account for the reported increased incidence of brain damage in exposed premature infants[47,48] and IAIPs could represent neuroprotectants in this population. In addition, prior to the data described herein and incorporated in its entirety, IAIPs have not been studied in the immature brain, making the conclusions disclosed herein highly novel. IAIPs are novel anti-inflammatory molecules that robustly block increases in pro-inflammatory cytokines in response to sepsis, and augment the rise in anti-inflammatory cytokine production.[11]

Our data in fetal sheep show that IAIPs have remarkable neuroprotective properties. Based upon our data during the perinatal period in fetal sheep, we believe administration of IAIPs can prevent some elements of brain damage in human infants and would be feasible as human blood products are currently used to treat infants. In addition, IAIPs could also be an adjunctive treatment to the partial protection afforded by hypothermia in full-term infants.[87] The IAIPs could also have a significant translational potential to prevent or attenuate brain damage in infants at risk for mental retardation and CP2. Many of the infants who are at risk for CP2 are premature infants and there is absolutely no preventive or therapeutic strategy for these infants except for the administration of magnesium sulfate to the mother, which has very limited protective properties only in some infants.

The issues with the current gold standard of treatment with hypothermia are as follows: For neo-natal patients, the issue is Hypoxic Ischemic Encephalopathy ("HIE") that is currently poorly treated with hypothermia treatment. The neonatal patient, when diagnosed with hypoxic ischemia, is placed on a cold (32 degrees F.) circulating mattress to cool their system. Treatment does not result in treatment of the symptoms and underlying issues, but only partially mitigates the impact of HIE. Patients are not returned to a normal healthy state after HIE treated by hypothermia. The current gold standard is only partially effective. Consequently, there is an urgent need to find additional adjunctive treatments.

The methods of the present invention include the administration of an IAIP to a neonate in need thereof for the treatment of tissue ischemia, such as HIE. The method includes administering an IAIP to a neonate at risk of ischemia or other brain injury (e.g., as a neuroprotective), as well as to neonates diagnosed with ischemia or other brain injury.

The present invention is significant in that the frequency and severity of negative outcomes following Neonatal Encephalopathy are excessively high. Between 40 and 58% of the neonatal patients who experienced hypoxic ischemia died or had severe mental disability, as measured by IQ score less than 70. No current treatment effectively or satisfactorily addresses the primary concerns leading to death or significant mental impairment following hypoxic ischemia in neonatal patients.

The following is excerpted from the *New England Journal of Medicine*, incorporated in its entirety by reference: *New England Journal of Medicine*, "Childhood Outcomes after Hypothermia for Neonatal Encephalopathy", Shankaran et al, 2012; 366:2085-92:

BACKGROUND We previously reported early results of a randomized trial of whole-body hypothermia for neonatal hypoxic-ischemic encephalopathy showing a significant reduction in the rate of death or moderate or severe disability at 18 to 22 months of age. Long-term outcomes are now available.

METHODS In the original trial, we assigned infants with moderate or severe encephalopathy to usual care (the control group) or whole-body cooling to an esophageal temperature of 33.5° C. for 72 hours, followed by slow rewarming (the hypothermia group). We evaluated cognitive, attention and executive, and visuospatial function; neurologic outcomes; and physical and psychosocial health among participants at 6 to 7 years of age. The primary outcome of the present analyses was death or an IQ score below 70.

RESULTS Of the 208 trial participants, primary outcome data were available for 190. Of the 97 children in the hypothermia group and the 93 children in the control group, death or an IQ score below 70 occurred in 46 (47%) and 58 (62%), respectively (P=0.06); death occurred in 27 (28%) and 41 (44%) (P=0.04); and death or severe disability occurred in 38 (41%) and 53 (60%) (P=0.03). Other outcome data were available for the 122 surviving children, 70 in the hypothermia group and 52 in the control group. Moderate or severe disability occurred in 24 of 69 children (35%) and 19 of 50 children (38%), respectively (P=0.87). Attention-executive dysfunction occurred in 4% and 13%, respectively, of children receiving hypothermia and those receiving usual care (P=0.19), and visuospatial dysfunction occurred in 4% and 3% (P=0.80).

CONCLUSIONS The rate of the combined end point of death or an IQ score of less than 70 at 6 to 7 years of age was lower among children undergoing whole-body hypothermia than among those undergoing usual care, but the differences were not significant. However, hypothermia resulted in lower death rates and did not increase rates of severe disability among survivors. (Funded by the National Institutes of Health and the Eunice Kennedy Shriver NICHD Neonatal Research Network; ClinicalTrials.gov number, NCT00005772.)

Limitations of Treatment by Hypothermia

The following is excerpted from the *New England Journal of Medicine*, "Whole-Body Hypothermia for Neonates with Hypoxic-Ischemic Encephalopathy", Shankaran et al, 2005; 353:1574-84:

Background: Hypothermia is protective against brain injury after asphyxiation in animal models. However, the safety and effectiveness of hypothermia in term infants with encephalopathy is uncertain.

Methods: We conducted a randomized trial of hypothermia in infants with a gestational age of at least 36 weeks who were admitted to the hospital at or before six hours of age with either severe acidosis or perinatal complications and resuscitation at birth and who had moderate or severe encephalopathy. Infants were randomly assigned to usual care (control group) or whole-body cooling to an esophageal temperature of 33.5° C. for 72 hours, followed by slow rewarming (hypothermia group). Neurodevelopmental out-come was assessed at 18 to 22 months of age. The primary outcome was a combined end point of death or moderate or severe disability.

Results: Of 239 eligible infants, 102 were assigned to the hypothermia group and 106 to the control group. Adverse events were similar in the two groups during the 72 hours of cooling. Primary outcome data were available for 205 infants. Death or moderate or severe disability occurred in 45 of 102 infants (44 percent) in the hypothermia group and 64 of 103 infants (62 percent) in the control group (risk ratio, 0.72; 95 percent confidence interval, 0.54 to 0.95; P=0.01). Twenty-four infants (24 percent) in the hypothermia group and 38 (37 percent) in the control group died (risk ratio, 0.68; 95 percent confidence interval, 0.44 to 1.05; P=0.08). There was no increase in major disability among survivors; the rate of cerebral palsy was 15 of 77 (19 percent) in the hypothermia group as compared with 19 of 64 (30 percent) in the control group (risk ratio, 0.68; 95 percent confidence interval, 0.38 to 1.22; P=0.20).

Conclusions: Whole-body hypothermia reduces the risk of death or disability in infants with moderate or severe hypoxic-ischemic encephalopathy.

Neuroprotection and Treatment of Hypoxic Ischemia in Adults

The same thought process applies to the neuroprotective properties of IAIP for adult patients who have experienced stroke. For adult patients, stroke is the largest issue, and may lead towards mental impairment and paralysis. stroke is currently treated with a limited clinical armamentarium, with Tissue Plasminogen Activator ("TPA") as the lead treatment method. tPA must be administered within 4.5 hours of the stroke event, and is not fully effective. tPA is a blood thinning agent, which makes it contraindicated for patients with bleeding issues and for patients with potential hemorrhagic transformation of stroke.

Adults suffering a stroke are not treated with hypothermia. Instead, stroke patients are treated with Tissue Plasminogen Activator ("tPA"). tPA is a thrombolytic agent used in diseases that feature blood clots due to events such as pulmonary embolism, myocardial infarction, and stroke. tPA must be administered as quickly as possible after the medical event in order to be as effective as possible, and is intended to be administered within 4.5 hours of the event. The efficacy of tPA as a treatment for stroke has not been proven, and remains a source of controversy. See, e.g., Western Journal of Medicine, "Truths about the NINDS Study: Setting the Record Straight", *West J Med.* 2002 May; 176(3): 192-194, Jeffrey Mann:

Thrombolysis for acute ischemic stroke has been studied for more than a decade, but its efficacy remains controversial. The first study to claim that tissue plasminogen activator (tPA) is effective in the treatment of acute ischemic stroke was a multicenter clinical trial coordinated by the National Institute of Neurological Disorders and Stroke (NINDS) Study Group. The NINDS study's conclusions, published in 1995,1 were that "treatment with intravenous tPA within 3 hours of the onset of ischemic stroke improved clinical outcome at 3 months . . . . [A]s compared with patients given placebo, patients treated with tPA were at least 30% more likely to have minimal or no disability at 3 months." 1(p 1586) The NINDS study was widely perceived to be a well-executed and analyzed randomized controlled trial, and its results were well received by many medical professionals and the public."

In summary, the recommendations for the use of tPA in patients with acute ischemic stroke were based on an initial misinterpretation of the results of the NINDS trial and are, therefore, unwarranted. The NINDS investigators may think that tPA works and that no further trials are needed. In fact, Lyden in an editorial in "Controversies in Stroke" wrote, "Perhaps we will find a way to treat patients later than 3 hours, and further studies are needed to push the outer limits of the time window, but within the 3-hourwindow, no further trials are needed; the drug works. The dictum primum nonocere still applies: we must do no harm, either by actively committing an act or by withholding a proven therapy through inaction."7(p 2709). The readers of this article should think carefully about these issues and independently decide whether further trials of the use of tPA for acute ischemic stroke are needed.

In addition, administering tPA is difficult, impractical, and does not produce a positive clinical benefit in any more than 10% of the studied patient population when compared to placebo. See, e.g., Cleveland Clinic Journal of Medicine, volume 69, number 9, September 2002, "Acute Stroke Therapy: beyond IV tPA", Furlan is incorporated in its entirety by reference.

tPA FOR STROKE:EFFECTIVE BUT OFTEN IMPRACTICAL In a landmark study from the National Institute of Neurological Disorders and Stroke (NINDS),1 624 patients were randomized to receive either placebo or IV tPA (0.9 mg/kg, maximum 90 mg, 10% as a bolus and the remainder within 60 minutes) within 3 hours of stroke onset. At 90 days, there was an 11% to 13% absolute increase in essentially full neurologic recovery among treated patients. But at a price. The rate of symptomatic intracerebral hemorrhage at 36 hours was significantly higher in the tPA group (6.4% vs 0.6%). Although overall mortality was not increased, tPA-related intracerebral hemorrhage is often fatal. The net benefit of tPA was reduced for older patients (age>77 years) and for more severely affected patients (ie, with a National Institutes of Health Stroke Scale [NIHSS] score>22).

The Food and Drug Administration (FDA) approved tPA for treating acute ischemic stroke in June 1996, but only for patients meeting the inclusion criteria of the NINDS study. Most important of these: treatment must begin with—in 3 hours of the onset of stroke, and before this can happen, patients must undergo a computed tomographic (CT) scan to rule out intracerebral hemorrhage.

Using IV tPA in clinical practice has proved very difficult. For example, in Cleveland hospitals in 1997-1998, only 1.8% of patients admitted with ischemic stroke received IV tPA.2

Further underscoring the impracticalities of administering tPA to combat the degenerative effects of stroke are described by Kevin Pho, MD, ER Stories, *MD in Conditions*, Sep. 1, 2010: "The TPA Time Limit for Stroke Causes Mass Chaos in the ER":

I hate acute strokes. There are several reasons for it. Most of them are logistical. First, everyone gets into a tizzy because of the 3 (or 4.5) hour time limit after the onset of symptoms that which TPA can be given and hopefully improve the patient's outcome. Unfortunately, this time limit (and the data for TPA's efficacy is only OK at best) causes mass chaos and annoyance.

First, one has to establish 100% what the exact time of onset was. This is not easy most of the time. I would say about 80% of "acute" strokes brought in by EMS turn out to not be within that window. It takes more than just saying "when did the symptoms start?"

Often the patient is elderly and demented. Often they live alone. Often there were milder symptoms before that were ignored or unrealized. Occasionally the person has hemi-neglect and can't really say when things started. Sometimes there is alcohol on board. Sometimes the symptoms are on top of pre-existing stroke damage and it is hard to tell if it is really new or worse.

Sometimes patients probably had a seizure at onset and that prevents them from getting TPA.

All these things make history taking a royal pain in the ass. And remember, it must be done quick! The exam can be hard too. Sometimes the patient can't reliably follow commands or there is a language barrier. Sometimes the patient's preexisting abnormal findings make it hard to tell if something is old or not. Sometimes the person is so out of it the whole thing is a waste of time.

Second, once you are sure it is a stroke, you have to hustle. If the person came in within one hour, no prob. But if 2 have passed (or 3.5 in a younger patient eligible for the 4.5 hour window), it is tough. The bloods have to be sent off. Blood pressure may have to be corrected. You have to zoom the patient over to CT and get it read. You have to get consent (often from a family member who is on the telephone), as well as the worst part of all. That would be calling the neurologist.

Many hospitals (like mine) require that the giving of TPA is a two-doctor job—and one is the neurologist. I think mostly because neurologists are the best at making sure it really is a stoke. In many cases it is pretty obvious, but in the borderline, more challenging cases, they are much more astute than me at teasing out the minutiae from the history and subtle exam findings. This is important because TPA has a big risk; bleeding like stink. Turn a ischemic stoke into a hemorrhagic one and you've screwed the patient royally. Cause a bleed in someone who really was not having a stoke? You are so screwed it is not even funny.

Anyway, calling the neurologist sucks. Why? The same reason it sucks for everyone else. They have to drop whatever it is they are doing and come flying in. As you can guess, strokes that happen at 2 am are truly unwelcome. They hate to get awoken, and I hate to wake them. Even if it is during the day, they have to abandon their rounds or their patients in the office to come in. Of course I know it sucks (it wrecks my rhythm too) but part of me is just like, "You guys did the research for this stuff and published the papers and made it standard of care."

Regardless, one cannot explain how grumpy and unpleasant to deal with the neurologist is at 4 am. If anything is out of place, if the flow of things is not perfectly smooth, or if the nurses don't have everything ready for them, it's freak-out time. God forbid if the diagnosis is wrong. Or if they feel the symptoms started earlier and the patient is out of the window. Or if it turns out the patient has some contraindication to getting the drug. Lets just say the discussion between the doctors is not pleasant.

All this is bad enough but what really takes the cake is that the treatment is not very good. The data in the big studies is sub-par (certainly compared to many other treatments for things we do). Even under the best of circumstances (which seem to almost never occur) the improvement the patient gets is only moderate (and even worse during the 3-4.5 hour window). Of course, that may be significant in the long run for the patient's functioning but a good part of the time, they don't improve at all.

Add that in with the people who bleed and you have a treatment that few people are enthusiastic about. Of course this leads to another part, the giving or not giving of TPA in acute stroke is a huge lawsuit waiting to happen. If you give it and the person does poorly, you get sued. If you don't give it and the person does worse, you get sued. So, I say please invent something better for strokes.

Finally, of course, I hate it for what it does to patients. It can be truly devastating and the costs to the patient, family, and society is staggering.

New device innovation is focused on endovascular cooling devices vs. external heat-exchange cooling surfaces. Hypothermia is widely believed to offer the following benefits (Cleveland Clinic, Furlan):

Hypothermia may exert its effect by reducing glutamate release, free-radical mechanisms. ischemic depolarization, and kinase reactions; by preserving the blood-brain barrier and cytoskeleton; and by suppressing inflammatory mechanisms. Hypothermia may be effective because of this so-called "dirty" neuroprotection as compared with drugs that block only one aspect of the ischemic cascade Treatment of Other Disease Conditions Using IAIPs In addition to providing neuroprotection (in adults and neonates) and treating tissue ischemia (e.g., in the brain), IAIPs can also be administered to a subject (e.g., a human) for the treatment of burns. IAIPs can also be administered for the treatment of influenza (e.g., H1N1 flu, bird flu, or other influenza strains known to cause disease in humans). Other viral infections that can be treated by administering an IAIP include, e.g., Dengue fever and West Nile fever.

Animal Model of Disease in Humans

The ovine fetus has been widely used to investigate brain development (A59-A61). The neurodevelopment of the immature ovine brain is similar to that of the premature infant with respect to completion of neurogenesis, onset of cerebral sulcation, and detection of the cortical component of the auditory evoked potentials (A59, A62, A63). Full term in sheep pregnancy is 148 days of gestation. The preterm fetal sheep brain between 94 and 96 days of gestation is comparable to that of the preterm infant between 24 and 28 weeks of gestation, whereas fetal sheep at 135 days of gestation is similar to that of the near term human infant (A64). We examined sheep over a wide range of ages to have a broad developmental range, over which to examine changes in IAIPs expression in brain and somatic organs. We examined fetal sheep at 87-90, 105-108, and 135-137 days of gestation, which represents 60% or 70%, 90% of the ovine gestation, newborn lambs, and adult sheep. Although rodents are frequently used to study brain development, the rodent brain is immature at birth (A64) and almost completely agyric. In contrast, similar to the non-human primate and human brain, the sheep brain develops prenatally and is gyrencephalic.

In view of the similarities in the development of sheep and neonate brains, sheep represent a useful model for examining the effectiveness of IAIP therapies in neonates and human subjects generally.

In the present invention, IAIP levels are measured and correlated to healthy or injured brain post hypoxic ischemia. Previous work by Yow-Pin Lim, M.D., Ph.D. has clearly shown strong correlation between IAIP levels and systemic inflammation, where systemic inflammation is elevated when IAIP levels are depressed. Or it could be said that systemic inflammation occurs because IAIP levels are depressed. The present inventors recognized that ischemia/stroke represents a non-infectious cause of brain inflammation, and thus discovered that because IAIP levels correlate to brain ischemia/stroke, patients at risk of, or experiencing, ischemia/stroke can be treated by administration of an IAIP.

The following examples are provided by way of illustration only and not by way of limitation. Those of skill in the art will readily recognize a variety of non-critical parameters that could be changed or modified to yield essentially the same or similar results.

EXAMPLES

Example 1: IAIPs Attenuate Ischemic Brain Injury in the Ovine Fetus

We exposed fetal sheep to ischemia/reperfusion injury.[4, 5, 88] Sections stained with Luxol fast blue-hematoxylin/eosin (LFB-H&E) to delineate white matter lesions showed homogeneous blue stained myelin and healthy appearing cerebral cortex in control (FIG. 4A,1×) in contrast to ischemic (FIG. 4B,1×) brains that exhibited decreased blue staining and cerebral cortical thinning indicating severe white matter and neuronal loss, respectively. Fetal sheep treated with IAIPs (4 mg/kg 15 min, 24 & 48 h after carotid occlusion, FIG. 4C,1×) showed remarkable preservation of white matter and cerebral cortex. A pathologist, unaware of treatments, scored the sections according to the percentage of neuronal and white matter destruction using a grading system that we previously reported (FIG. 6).[4, 5, 88] The pathological scores indicated severe cerebral cortical and white matter injury in fetuses exposed to ischemia/reperfusion (closed bars) compared with control (open bars; P=0.07) and IAIP-treated ischemia/reperfusion (hatched bars, treatment as above). We also identified dramatic ischemia-related decreases in MBP and altered cellularity of GFAP positive astrocytes in this model.[5] Our findings suggest that treatment with IAIPs have great potential as a neuroprotective agent in the perinatal period and probably also for other age groups.

Example 2: Ontogeny of Inter Alpha Inhibitor Proteins in Ovine Brain and Somatic Tissues IAIPs Detection by ELISA and Western Immunoblot in Plasma IAIPs detected by the sheep specific ELISA in ovine plasma were lower (P<0.05) in the fetuses at 70% and 90% gestation than in the newborn lambs, and lower in the fetuses at 90% of gestation than in adult sheep.

The IAIPs were detected as 125 kDa and 250 kDa bands in ovine plasma by Western immunoblot. The expression of 125 kDa band did not differ among the age groups. In contrast, the expression of 250 kDa band was lower in the fetuses at 70% and 90% gestation, and in the newborn lambs than in the adult sheep.

IAIPs detection by Western immunoblot in cerebral cortex, CP and CSF. IAIPs were detected in cerebral cortex, CP and CSF as 125 kDa and 250 kDa protein bands by Western immunoblot using the specific antibody against IAIPs. The expression of 125 kDa band was higher in the cerebral cortex in fetuses at 70% and 90% of gestation than in the newborn lambs, and higher in the adult sheep than in the newborn lambs. In contrast, the 250 kDa protein band expression in was lower in the cerebral cortex in the fetuses at 70% and 90% gestation and in the newborn lambs than in the adult sheep. The expression of the 125 kDa band in CP was lower in newborn lambs than in the fetuses at 60% and 90% of gestation and in the adult sheep and the 250 kDa protein expression was higher in the fetus at 60% and 90% gestation and in the adult sheep than in the newborn lambs, but lower in the fetuses at 60% and 90% gestation than in the adult sheep. The expression of the 125 kDa and 250 kDa protein bands in CSF were higher in fetuses at 70% and 90% of gestation than in the newborn lambs. The IAIPs levels in the CSF were below the limit of detection by the sheep specific ELISA. In summary, the cerebral cortex, CP and CSF each exhibit distinct patterns of expression for the 125 kDa and 250 kDa proteins. However, both molecules appear lower in the newborn lambs than in the fetuses at 70% and 90% of gestation in both CP and CSF. We do not know the pattern of expression in adult sheep as we did not have samples from the adult sheep.

IAIPs Detection by Western Immunoblot in Somatic Tissues.

The 125 kDa and 250 kDa IAIPs are expressed in different somatic organs. IAIPs were also detected as 125 kDa and 250 kDa proteins in placenta, liver, heart and kidney in fetal, newborn and adult sheep. In placenta, the 125 kDa band expression was lower at 70% than at 90% of gestation, but the 250 kDa expression did not differ between the fetuses at 70% and 90% of gestation. In the liver, 125 kDa and 250 kDa band expressions were lower in the fetuses at 70% and 90% gestation and in the newborn lambs compared with the adult sheep. In the heart, the expression of 125 kDa band was higher in the fetuses at 70% gestation than in the fetuses at 90% of gestation, in the newborn lambs and in the adult sheep. In contrast, the 250 kDa band did not differ among the groups. In the kidney, the 125 kDa band expression was higher in fetuses at 70% gestation and in the adult sheep compared with the fetuses at 90% of gestation and the newborn lambs, but the expression of 250 kDa band was lower in fetuses at 70% and 90% of gestation and in the newborn lambs than in the adult sheep.

DISCUSSION

The purpose of our study was to examine the expression of IAIPs in the brain and in somatic organs of sheep during development as an initial approach to understand these critical molecules during development. The presence of IAIPs was identified for the first time in plasma, cerebral cortex, CP, liver, heart, and kidney from early in fetal and through the neonatal period up to maturity in adult sheep, and in the placenta and CSF during fetal life as both the 125 kDa and 250 kDa proteins. The findings of our study are novel because to the best of our knowledge previous work has not reported distributions of IAIPs in the brain and somatic organs during a wide span of development in any species. The major findings of this study were as follows. 1. The concentration of IAIPs increase in plasma after birth. 2. The 125 kDa expression of IAIPs was higher in the adult and fetal than in newborn lamb cerebral cortices, but the 250 kDa protein expression was higher in adult than fetal and newborn cerebral cortices. 3. The expression of IAIPs in CP was highest in the adult sheep. 4. IAIPs were high in CSF of fetal sheep and very low in newborn lambs after birth. 5. IAIPs exhibit ontogenic patterns of expression specific to each molecular species and organ. The presence of both molecules of IAIPs with organ specific patterns of expression during ovine development may be interpreted to suggest that these proteins have important immunomolatory (1, 2) functions during organ development.

Recent studies have shown high levels of circulating IAIPs are normally present in adult human plasma (2, 54) and even in plasma of premature infants (6-8). Our finding during ovine development extend these observations in human plasma and suggests the concentrations of IAIPs, measured by ELISA, increase markely after birth. In addition, the expression of the IAIP-related molecules, which contribute to the total amount of IAIPs measured by ELISA, differ with respect to their expression during development such that the expression of the 125 kDa moiety is similar at all ages, but that of the 250 kda protein increases markedly after birth suggesting that it is the 250 kDa moiety that contributes to the high levels of total IAIPs observed in adult sheep plasma. However, although the level of the total IAIPs (ELISA) are high in the newborn lambs, the expression of the 250 kda protein appears low in lambs, suggesting that the 250 kDa moiety cannot account for the high levels of the total IAIP protein after birth.

IAIPs related proteins have previously been localized in various tissues in adult rodents and humans, including cerebrum and cerebellum, lung, liver, intestines, colon, kidney, bladder, testes, and skin (22, 74-76). IAIPs also have been shown to have a specific distribution within the brains of mice and rats with localization primarily in the cerebral cortex, hippocampus and hypothalamus (77). Unfortunately, we only had residual cerebral cortical and CP samples from our previous studies (61, 65-68) so that we cannot comment on the amounts of IAIPs expressed in other brain regions. However, in the cerebral cortex, we observed a distinct ontogenic pattern for the 125 kDa and 250 kDa moieties, such that the former was higher in the fetuses and the later higher in the adult sheep. Although we cannot comment upon the distribution of IAIPs in other brain regions, identify the localization of IAIPs to specific cell types or identify the biological functions of IAIPs from our study, others have reported that IAIPs are most likely produced within the neurons (77) and/or astrocytes (29) in the murine brain, because intense immunoreactivities were localized to neuronal processes.

Inflammation plays a key role in many CNS disorders (78). There is now evidence to suggest that bidirectional communications between the CNS and periphery could contribute to acute and chronic CNS disorders (78). Increased levels of IAIPs in ovine plasma and CNS tissue during development could be related to the importance of these molecules in systemic and CNS inflammatory and immunological responses (1, 2). Recent evidence suggests that bikunin, the light chain of IAIPs, reduces oxidative stress, early inflammation, and endothelial activation in the forebrain of rats (79), reduces ischemia-reperfusion-related delayed neuronal apoptosis in gerbils (80), protects against white matter demyelination and oligodendrocytes from apoptosis, and promotes remyelination in a model of experimental autoimmune encephalomyelitis (32). In addition, bikunin attenuates polymorphonuclear neutrophil infiltration and decreases infarct volume in ischemic-reperfusion injury in the brain of adult rats (31). Moreover, endogenous IAIPs appear to be directly involved in repair process of injured neurons (31) and protease inhibitors derived from neuronal cells function as regulators of neurite regeneration and outgrowth (81). Hence, IAIPs appear to have a variety of important neuroprotective effects in several animal models. Therefore, based upon our findings identifying the presence of IAIPs in relatively large amounts throughout ovine development, we speculate that these molecules could potentially represent endogenous anti-inflammatory molecules with neuroprotective properties.

The patterns of IAIP expression in the choroid plexus were somewhat similar to those of the cerebral cortex during development. CSF is produced as an ultrafiltrate of plasma by the choroid plexus and also from drainage of interstitial fluid from CNS tissues. Approximately 80% of the total amount of protein in CSF originates from blood with the remaining 20% originating directly from the CNS (82). CSF in adults has much lower protein concentrations than plasma due to restricted entry of blood derived components through the blood-CSF barrier (40). Most of the highly abundant proteins in plasma are also elevated in CSF with exception of those proteins forming large complexes resulting in very low diffusion rates into CSF(40). High concentrations of protein have been previously reported in the immature CSF of fetal sheep (57) and in newborn and preterm infants with levels several times higher than those of adults (83). The higher protein concentrations in fetal CSF are most likely a result local production by CP rather than immaturity of the blood-brain or blood-CSF barriers because the blood-brain and blood-CSF barriers form very early during development in the fetus (40, 56, 83-85).

The high levels of both the 125 kDa and 250 kDa IAIP protein moieties expressed in CSF in the fetal sheep, which decrease after birth, are consistent with findings of elevated levels of other proteins during gestation in several other species including rodents, pigs, rabbits, chickens and in premature infants (56, 83, 86-89). Although initially it was thought that elevated protein concentrations in CSF simply reflected an immature leaky blood-brain barrier to proteins during development, more recent information suggests that elevated CSF proteins in the fetus and newborn most likely have important roles for brain growth and development (40). The protein composition of CSF in the early stages of fetal development is very complex. The majority of proteins are low molecular weight proteins such as albumin, alpha-fetoprotein, transferrin, lipoproteins etc., the concentrations of which show significant variations during different stages of development (56, 90). These protein fractions most likely represent molecules that have important biological functions including growth factors and cytokines, which could influence the development of neuroepithelial cells (40, 86, 91). The ontogenic patterns of protein concentrations in fetal CSF have been studied in several species. In the chick and sheep, protein concentrations increase consistently during the late fetal period and decrease just before delivery (56, 92, 93). In contrast, this decrease does not occur until after birth in rats (55), suggesting that phylogenic differences play a role in the pattern protein expression in CSF during maturation. Differences between patterns of protein concentrations in sheep and rodent CSF most likely result from maturational differences in brain development among species (94). A large proportion of brain development in the sheep occurs before birth and, similar to the human, the sheep exhibits two distinct phases of brain growth (94, 95). The first phase occurs between 40 and 80 days of gestation and is thought to represent neuronal multiplication and the second phase occurs between 95 and 130 days of gestation and represents neuralgia multiplication and myelination (62, 94, 95). In contrast, the majority of the rodent brain growth occurs after birth (Dobbing et al 1979). These differences could also influence the expression of CSF proteins during development.

IAIPs have been previously detected in human CSF in patients with brain tumors and inflammatory diseases, but their levels were not affected by levels of systemic bikunin (96). CSF proteins may originate from several sources including plasma, brain parenchyma and choroid plexus secretion. Both the in immature and adult subjects, CP synthesizes a large number of neuropeptides, growth factors, and cytokines (91). Numerous studies suggest that the high concentration of protein in fetal CSF is not due to simple diffusion from plasma, rather there are specific developmentally regulated transfer mechanisms in the CP (42, 97-103). Inspection suggests that this phenomenon is true in sheep as the CSF IAIP levels are higher in the fetuses than in newborn lambs, but the plasma IAIPs levels are higher in the newborn lambs than in fetuses. Therefore, we speculate that the presence relatively high levels of IAIPs in fetal CSF is probably due to local synthesis by the CP and brain tissue during critical periods of brain development, and that these molecules in CSF could be important in brain development in the fetus. Although we cannot discern from our study the reason the levels of IAPs decreased dramatically after birth, we speculate that the stress of delivery along with endogenous hormonal changes could have affected the CSF levels of IAIPs after birth.

Endogenous IAIPs were detected for the first time during the development in the sheep CNS. They were detected in relatively high amounts in the cerebral cortex and CP at all stages of development and in the CSF during fetal life. However, expression in cerebral cortex, CP and CSF decreased in newborn lambs after delivery. We speculate that the relative reductions in IAIPs in the newborn lambs after birth could relate to the stress of delivery. The levels in cerebral cortex and CP increased again in adult sheep, most likely related to the importance of these proteins in innate immunity. Although we cannot be certain of the physiological significance our findings of high IAIPs levels in ovine brain, CP, and CSF during the development, our findings raise the interesting possibility that they are important molecules for brain development.

Similar to our findings in the brain, we have shown for the first time that these immunomodulatory proteins are present in somatic organs and in the placenta, and that they exhibit molecular weight and organ specific patterns of developmental regulation in liver, heart, kidney and placenta. Although the exact functions of IAIPs are not known, their presence in large amounts with organ specific variations during development raises the possibility that they represent endogenous anti-inflammatory molecules with organ specific differential production or modulation during development.

There are several limitations to our study. We did not have CSF samples from adult sheep available and, consequently can not compare adult values with those of the fetuses and newborn lambs. However, IAMPs are not detectable in CSF from healthy adult humans (Y. P. Lim, personal communication, non-published data, 2012), but are increased in the presence of inflammation and tumors (96). We also did not have samples properly saved from our previous studies to determine the specific immunohistochemical location of IAIPs the brain and we did not have tissue available from other brain regions. Consequently, we cannot comment upon the cellular localization of IAIPs or on their expression in other brain regions.

CONCLUSIONS

We conclude that IAIPs exhibit specific patterns of expression in the CNS and somatic organs of sheep during development. Although exact functions of IAIP are not known in CNS and somatic tissues, their presence in high amounts during development suggests their importance to brain and organ development.

Materials and Methods

The present study was conducted after approval by the Institutional Animal Care and Use Committees of Brown University and Women & Infants Hospital of Rhode Island and according to the national Institutes of health Guidelines for use of experimental animals.

Animal Preparation and Experimental Design

Plasma, cerebral cortical, CP, CSF, placenta, liver, heart and kidney tissues samples for the present study were frozen samples obtained from placebo treated sham operated control animals from previous studies (61, 65-67). Samples from all age groups were obtained over similar time intervals. Surgical procedures and physiological measures were performed for the former studies (61, 65-68). As described previously in detail (61, 65-67) surgery was performed under ketamine (10 mg/kg) and 1%-2% halothane anesthesia in pregnant ewes at 60% (87-90 days), 70% (106-107 days), 90% (135-138 days) of gestation, newborn lambs (4-6 days of age) and adult non pregnant sheep (3 years of age). Plasma samples were obtained from all animals just before the euthanasia. All animals were sham-operated control animals from our previous studies and sacrificed without further intervention. At the end of the studies, a CSF sample was obtained from the fetal and newborn sheep with a direct puncture of the allantoic membrane. The sample was inspected for blood contamination and discarded if there was evidence of contamination. CSF samples were not available from the adult sheep. Tissues, plasma, and CSF were snap frozen in liquid nitrogen and remained at −80° C. until analysis. Although choroid plexus samples were not available from fetuses at 70% gestation, samples were available from fetal sheep at 60% gestation.

Competitive ELISA to measure IAIPs level in ovine plasma and CSF IAIPs concentrations were measured by specially developed competitive ELISA in sheep plasma using a polyclonal antibody against human IAIPs (R-16 pAb). The polyclonal antibody was generated by immunizing rabbits with highly purified human plasma derived IAIPs. The R-16 pAb cross-reacts with non-human IAIPs including sheep. 96-well high binding microplate plates Microlon 600 (Greiner Bio-One, Monroe, N.C., USA) were coated with purified sheep IAIPs. Sheep IAIPs were purified from sheep serum (Quad Five, Ryegate, Mo., USA) by anion-exchange chromatography on a Toyopearl Q-600C-AR column (Tosoh Bioscience, King of Prussia, Pa., USA). Bound IAIPs were eluted with a buffer containing 750 mM NaCl. The purified sheep IAIPs were diluted in 100 mM NaP04 buffer pH 6.5 and immobilized on the microplates (50 ng/per well) for 1 h at room temperature or overnight at 4° C. Subsequently, the microplate was blocked with 200 µL of 5% non-fat dried milk in PBS and 0.05% Tween. Sheep plasma was diluted in PBS and a known amount of purified sheep IAIPs was serially diluted in PBS containing 1% BSA to establish a standard curve for quantitative analysis of IAIP concentrations in the samples. After 50 µL of samples and serially diluted IAIPs standards were added to the wells, 50 µL of R-16 pAb diluted in 1:1200 in PBS was added to each well. Plates were incubated for 1 h at room temperature and subsequently washed with PBS and 0.05% Tween using automated plate washer (Biotek EL-404, Winooski, Vt., USA). The bound R-16 pAb was detected by adding HRP-conjugated goat anti-rabbit IgG (Invitrogen, Carlsbad, Calif., USA) for 1 h at room temperature. After washing, 100-µL Enhanced K-Blue TMB substrate (Neogen Corp, Lexington, Ky., USA) was added to the wells and the reaction was stopped by adding 100 µL 1N HCl solution. The absorbance at 450 nm was measured on SpectraMAX Plus microplate reader (Molecular Devices, Sunnyvale, Calif., USA). Each sample was tested in triplicate and assays were repeated at least twice on all samples.

Preparation of Cytosolic Tissue Fractions

Cell cytosolic fractions of cerebral cortex, CP, placenta, liver, heart, kidney for IAIPs were extracted in buffer A (TRIS 10 mM pH 6.8, Sucrose, MgCl) with one percent complete protease inhibitor cocktail (Sigma, St. Louis, Mo., USA). Total protein concentrations of the homogenates were determined with a bicinchoninic acid protein assay (BCA, Pierce, Rockford, Ill., USA). Aliquots of the extracted samples were stored at −80° C.

Western Immunoblot Detection and Quantification of Proteins

Fifteen to fifty µg protein of total protein per well (cerebral cortex: 50 g, choroid plexus: 15 µg, cerebral spinal fluid: 22.5 µl, plasma: 1 µl from 1:100 dilution; placenta: 30 µg, liver: 50 µg, heart: 50 µg and kidney: 50 µg) were fractionated by SDS-PAGE electrophoresis and transferred onto PVDF membranes (0.2 micron, Bio-Rad Laboratories, Hercules, Calif.) using a semi-dry technique. Membranes were incubated with IAIP primary rabbit polyclonal antibody (ProThera Biologics, East Providence R.I., USA) at a dilution of 1:5,000. The immunoblots were incubated in primary antibody overnight at 4° C. Peroxidase-labeled secondary antibody goat anti-rabbit (Alpha Diagnostic, San Antonio, Tex., USA) was incubated for 1 h at room temperature in a dilution of 1:10,000. Binding of the secondary antibody was detected with enhanced chemiluminescence (ECL plus, Western Blotting Detection reagents, Amersham Pharmacia Biotech, Inc., Piscataway, N.J., USA) before exposure to autoradiography film (Daigger, Vernon Hills, Ill., USA).

Experimental samples were normalized to a reference protein standard that was obtained from a homogenate protein pool from the tissues of a single adult sheep. For the purpose of this report, we refer to these samples as internal control samples. As we have previously described (69-72), these samples served as an internal control for quality of loading, transfer of the samples, normalization of the densitometric values, and to permit accurate comparisons among the different immunoblots (69, 70, 73). The use of internal control is unique to our laboratory and allows us to compare large groups of animals over a large number of different immunoblots. We developed this methodology because investigation of a large number of housekeeping proteins showed that they all exhibited significant variations during ovine development mitigating their use as house keeping proteins. The experimental protein autoradiographic densitometrical values were expressed as a ratio to the internal control, thus facilitating normalized comparisons among different groups and immunoblots. When this methodology was used within a single age group (newborn), the method correlates well with values that were normalized as ratios to β-actin (69).

Each immunoblot included samples from the four groups and three internal control samples. The internal control samples were included in three lanes, as the first, middle, and last samples on each immunoblot. We calculated a coefficient of variation for the internal control samples on each immunoblot. The values for the experimental samples were accepted as valid only if the percent coefficient of variation for the internal control samples was less than 20% on the immunoblot. Human inter-alpha-inhibitor protein served as a positive control for all immunoblots to ascertain that the antibody correctly identified the ovine proteins. Molecular weight standards (Bio-Rad Laboratories, Hercules, Calif. USA) were included in each immunoblot. The primary rabbit polyclonal anti-IAIP detected IAIPs bands at 125 and 250 kDa in all organs. Uniformity in inter-lane loading was also established by Coomassie blue (Sigma, St. Louis, Mo., USA) staining of the polyacrylamide gels and uniformity of transfer to the polyvinylidene difluoride membranes was confirmed by Ponceau S staining (Sigma, St. Louis, Mo., USA). For the purpose of illustration in the figures, we selected the immunoblot that most closely represented the mean values for each age group and tissue from the different immunoblots.

Densitometric Analysis

Band intensities were analyzed with a Gel-Pro Analyzer (Media Cybernetics, Silver Spring, Md., USA). All experimental samples were normalized to the respective average of the three internal control samples. However, the band intensities were expressed as arbitrary optical density units for CP and CSF as we did not have adult CP or CSF. The final values represented averages of the densitometry values obtained from the different immunoblots (plasma n=2; cerebral cortex n=8; choroid plexus n=5; cerebral spinal fluid n=2; placenta n=5, liver n=5; heart n=5; kidney n=5) and were presented as a ratio to the internal control sample except for CP and CSF.

Statistical Analysis

All results were expressed as means±SEM. Two-way analysis of variance (ANOVA) was used to compare the differences among the groups. The factors were age group (fetuses at 60%/70%, 90% of gestation, newborn, and adult) and protein expression (125 kDa and 250 kda band). When significant difference was detected by ANOVA, the Fischer least significant difference test was used to further describe the statistically significant differences among the groups. $P<0.05$ was considered statistically significant.

Example 3: IAIPs Provide Neuroprotection Prior to Stroke and Following Hypoxia/Ischemia in Neonates Neurological impairment secondary to oxygen deprivation, including hypoxia/ischemia (HI) associated with immaturity of vasculature and pulmonary insufficiency in premature and very low birth-weight infants, as well as HI events relating to birth, is the leading cause of neurologic morbidity and mortality in infants. Affected children are prone to long-term cognitive and behavioral deficits. Moreover, severity of injury and pathological outcome are dependent upon sex, with more substantial long-term deficits identified in male than female infants, even when matched for severity of injury. The cause(s) of these differences are largely unknown; however, data indicate sex differences in apoptotic mechanisms, suggesting sex-specific mechanism of HI-induced injury. We propose novel studies to examine this sex-based phenomenon, specifically with regard to underlying molecular/cellular features of an HI event. We will examine the role of pro-inflammatory cytokines (known to cause/accentuate brain injury) and inter-alpha inhibitor protein (IAIP, known to effectively down-regulate cytokines) in histological and long-term behavioral studies of male and female rats with HI. Exciting preliminary data suggest substantial decreases in IAIP acutely following brain ischemia in fetal sheep, as well as significant neuroprotection by IAIP in male HI rats. These findings, combined with previous data suggesting neuroprotection from pre-stroke IAIP treatment in adult rats, raise the possibility that exogenous IAIP following neonatal HI may represent an effective therapeutic strategy. However, given evidence of sex differences in long-term outcome following neonatal HI, it remains to be seen if male and female brain varies in cytokine activation and IAIP expression following injury, whether IAIP will prove neuroprotective to both sexes, and the mechanisms of such neuroprotection. Through histological and long-term behavioral study of both male and female rats, the proposed studies determine sex differences in cytokine and IAIP expression after HI and the modulation of key sex differences in cell death mechanisms by IAIP. Additionally, IAIP is poised to enter clinical trials for sepsis and related molecules are known to suppress preterm labor, thus, this therapeutic agent could rapidly enter clinical use to attenuate HI injury in infants, though we predict a sexually dimorphic response due to key modulators involved in sex-specific mechanisms of HI-related cell death.

Example 4: IAIP Administration

Systemic administration of IAIPs, or their cleavage products, reduces the production of pro-inflammatory cytokines and prevents/attenuates the development of ischemic-reperfusion injury in the immature brain. Using a highly reproducible model of brain ischemia-reperfusion in the ovine fetus, we have determined that treatment of the sheep fetus with IAIPs prevents/attenuates ischemia-related damage to the immature brain. Findings from our studies translates into an important novel treatment strategy for human infants with brain ischemia, as IAIPs can be prepared from human plasma, are in the development to treat adults with shock syndrome/sepsis, and similar agents are efficacious in inhibiting preterm delivery through suppression of cytokines and inflammatory mediators.[8-10, 12-16] Consequently, it will be feasible to use IAIPs as anti-inflammatory immunomodulators similar to the manner in which immunoglobulins and fresh frozen plasma are currently used in infants.

Figure 7:
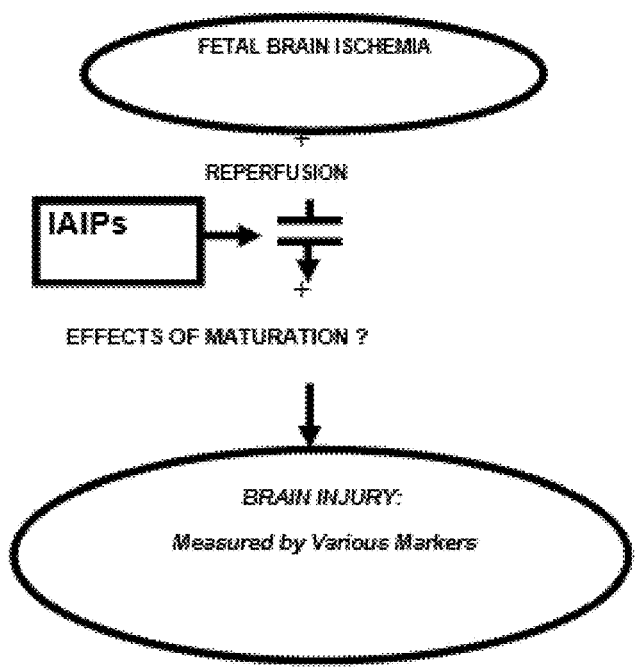
FIG. 7 is a schematic showing the effect of IAIPs on the brain.

We have examined the neuroprotective effects of systemic IAIP administration on brain ischemia in the ovine fetus. Our data suggest that IAIPs have important neuroprotective effects on ischemia-related cerebral cortical and white matter damage in the fetus (FIG. 7).

Example 5: Use of IAIPs in Treatment of Brain Damage in Premature Infant

There is an increasing incidence of premature birth, which contributes to 50% of cases of mental retardation and CP2. The incidence of CP2 is 40-148/1,000 in premature and 1-2/1,000 in full-term infants.[17-20] Although many infants who develop CP2 may be asymptomatic at birth,[21, 22] substantial evidence suggests antecedents of CP2 begin during fetal life.[23-26] Findings suggest that elevated cytokines are important in the pathogenesis of CP2.[22, 27-30] Periventricular leukomalacia (PVL) is a white matter lesion in premature neonates that is predictive of CP2.[31, 32] Although the etiology of this disorder is multifactorial, hypoxia-ischemia (HI) and overproduction of pro-inflammatory cytokines represent underlying factors.[33] Moreover, inflammatory processes that begin in utero are likely antecedents of brain damage in premature infants because early elevations in inflammation-related proteins, including cytokines, predict the risk of sonographic white matter damage.[4] However, this area remains controversial, as some have suggested neonatal infection and hypotension are more significant risk factors for white matter damage than chorioamnionitis.[2] Nonetheless, cytokines likely represent a final common pathway, activated by a variety of insults, which contribute to and/or exacerbate brain damage.[35] Systemic treatment with IAIPs represents a novel neuroprotective strategy that can down-regulate both systemic and central nervous system (CNS) cytokines to attenuate/prevent white matter damage and CP2.

Cytokines Effects on the Brain

Although the brain was previously considered an "immune privileged site" not under the influence of the immune system, important links between the brain and immune system are now recognized[36, 37] Cytokines are expressed at low levels in normal brain, but CNS injury increases vascular and parenchymal expression.[36] IL-1, TNF-α, INF-α, IL-6, INF-γ and IL-8 are important in CNS inflammation,[38] which results in liquefaction and/or glial scars, as neurons do not proliferate.[38] Pro-inflammatory cytokines, including IL-1, IL-6, and TNF-α, in brain parenchyma promote changes that accentuate brain injury.[39-44]

Pathogenesis of CP2 & PVL: Role of Cytokines in Ischemia-Reperfusion (I/R) Injury There are two main theories of pathogenesis of PVL/CP2. In the classic theory, HI results in damage to white matter,[45] but an alternative hypothesis places cytokines central to mechanisms of brain damage.[46] Intravascular cytokines are elevated in full-term infants who develop CP2,[22] amniotic fluid cytokines and cord blood IL-6 are increased in premature infants who develop white matter lesions,[28, 30] and pro-inflammatory cytokines are detected in white matter lesions of infants who died with PVL.[29] Evidence also suggests systemic inflammation, sepsis, and necrotizing enterocolitis (NEC) are associated with increased incidences of CP2, lower mental and psychomotor development, and visual impairment.[47, 48] Both NEC and sepsis increase the risk for inflammatory-mediated white matter damage.[47-49] IAIPs attenuate ischemia-related white matter damage, as suggested by our data;[5] IAIPs act by reducing ischemia-related increases in cytokines in the brain.[50]

Inter-Alpha Inhibitor Proteins, Systemic Inflammation & Tissue I/R Injury

IAIPs are a family of structurally related proteins found in plasma in high concentrations. IAIPs are important in inflammation, wound healing and cancer metastasis.[51, 52] The major forms in human plasma are Inter-alpha inhibitor (IaI), which consists of two heavy chains (H1 & H2) and a single light chain, and Pre-alpha Inhibitor (PaI), consisting of one heavy (H3) and one light chain. The light chain (bikunin) inhibits several serine proteases.[53] Liver is the major site of synthesis of heavy and light chains of IAIP.[54] High levels of IAIPs normally in plasma of adults and newborns, even when born prematurely, indicate these proteins are essential.[55] No person with complete absence of IAIP has ever been detected.[52] Markedly decreased plasma levels in septic patients and concomitant increases in IAIP-related fragments in the urine suggest these proteins are 'consumed' and rapidly cleared from systemic circulation during sepsis. Hepatic IAIP synthesis is also down-regulated during severe inflammation. Although the physiological function of IAIPs remain to be established, current data suggests these molecules are part of the innate immunity and play a critical role during inflammation.[56]

In addition to its broad anti-protease activity, IAIPs have unique immunomodulatory effects in reducing TNF-α during systemic inflammation[57] and augmenting anti-inflammatory IL-10 in a neonatal sepsis model.[11] The light chain of IAIPs (urinary trypsin inhibitor (UTI), or bikunin), also effectively inhibits premature delivery though cytokine suppression and inflammatory mediators.[8-10, 12-16] Although the mechanism(s) by which IAIPs mediate biological functions remains to be determined, recent discovery of pro-inflammatory stimulated glycoproteins and TNF-stimulated gene 6 (TSG-6) suggests upon forming a stable complex with TSG-6, one of the possible ligands of IAIP, inhibitory activity of IAIP toward plasmin is enhanced.[58]

Plasmin is a serine protease that activates metalloproteinases (MMPs), which are a part of the inflammation-related proteolytic cascade. MMPs are important in neuronal cell death resulting from intracerebral hemorrhage, neuroinflammation-related neurotoxicity, and neurodegenerative disorders.[59, 60] MMPs increase permeability of the blood-brain barrier resulting in edema, hemorrhage, and cell death.[59] Therefore, the ability of IAIPs to inhibit plasmin activity and in turn reduce the activation of injury-related MMPs may represent one of the mechanisms by which IAIPs could be neuroprotective.[61]

Figure 3:
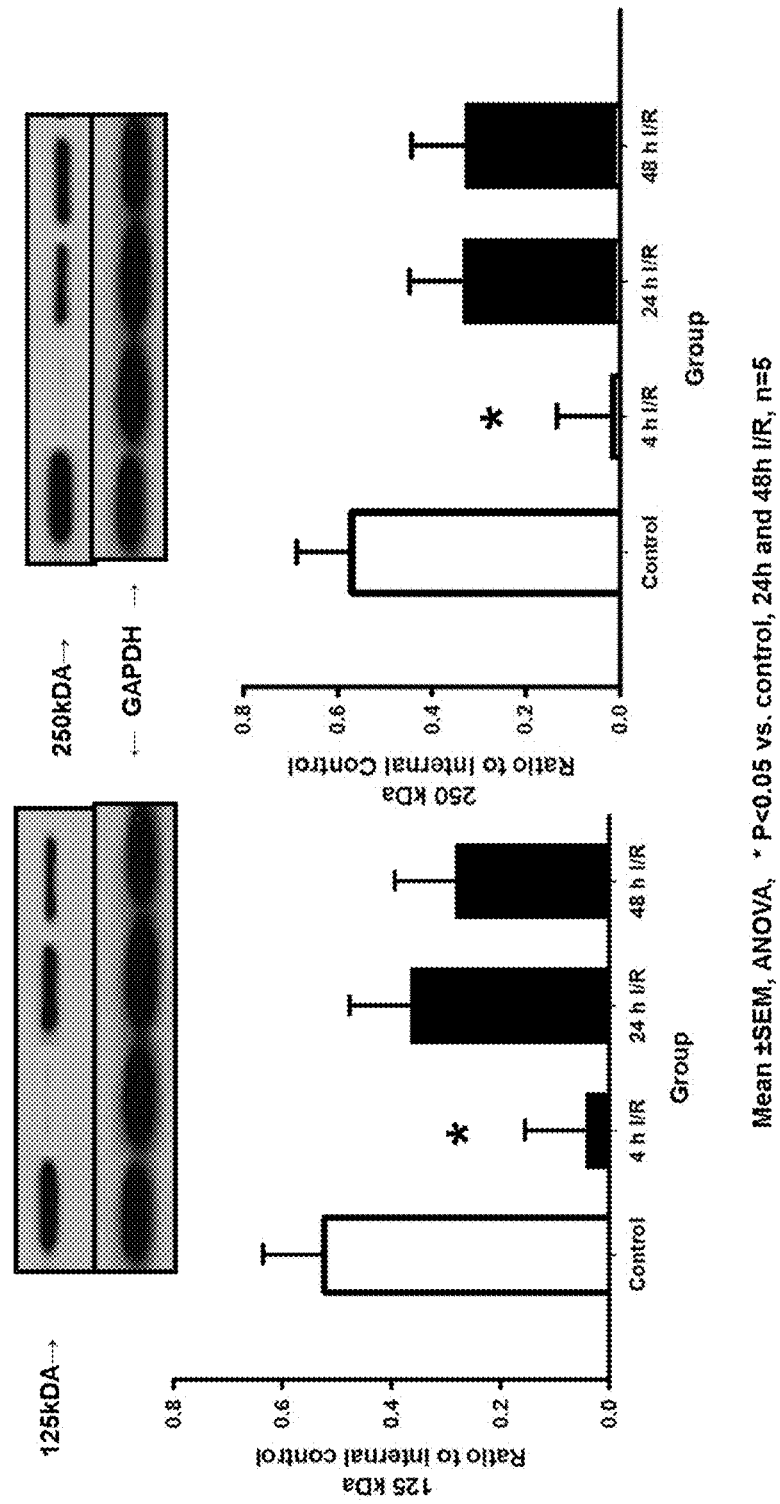
FIG. 3 is a set of graphs and insets showing IAIP levels in the brain of fetal sheep are dramatically reduced 4 hours after ischemic damage. Fetal sheep were exposed to brain ischemia and reperfusion for 4 h, 24 h and 48 h. There was a dramatic decrease in IAIP levels 4 h after brain ischemia, suggesting that IAIPs are consumed during ischemia. Repletion of IAIPs in the brain by intravenous treatment could be the mechanism by which treatment with IAIPs could reduce brain damage after hypoxia-ischemia or stroke. Graphs show pre-alpha inhibitor (125 kDa; left graph) and IAI (250 kDa right graph) Inset shows that pre-alpha inhibitor (125 kDa; left inset) and IAI (250 kDa right inset) bands show decreased expression after 30 min. of ischemia and 4 h of reperfusion (1/R); n=5/group, mean±SEM; *p<0.05 vs control. Expression returned toward control values at 24 and 48 h after ischemia.

IAIPs and related molecules have been detected in neurons, astrocytes, and meningeal cells of the brain and, based upon their role in other organs, may function as endogenous neuroprotective molecules. Moreover, we detected IAIPs in the cerebral cortex (FIG. 4) of sheep during development and in cerebral spinal fluid of ovine fetuses (CSF). Bikunin has been shown to block TNF-α's production during the reperfusion phase of ischemic injury in several organs (liver, kidney, heart, intestine and lung),[62-64] however, there is very little information on these molecules in brain. We have recently shown decreases in IAIPs associated with ischemia-reperfusion in the ovine fetal brain (FIG. 3) and others report UTI attenuates stroke-related brain injury and experimental autoimmune encephalomyelitis (EAE)-related white matter loss in adult rats.[61, 65]

Figure 5:
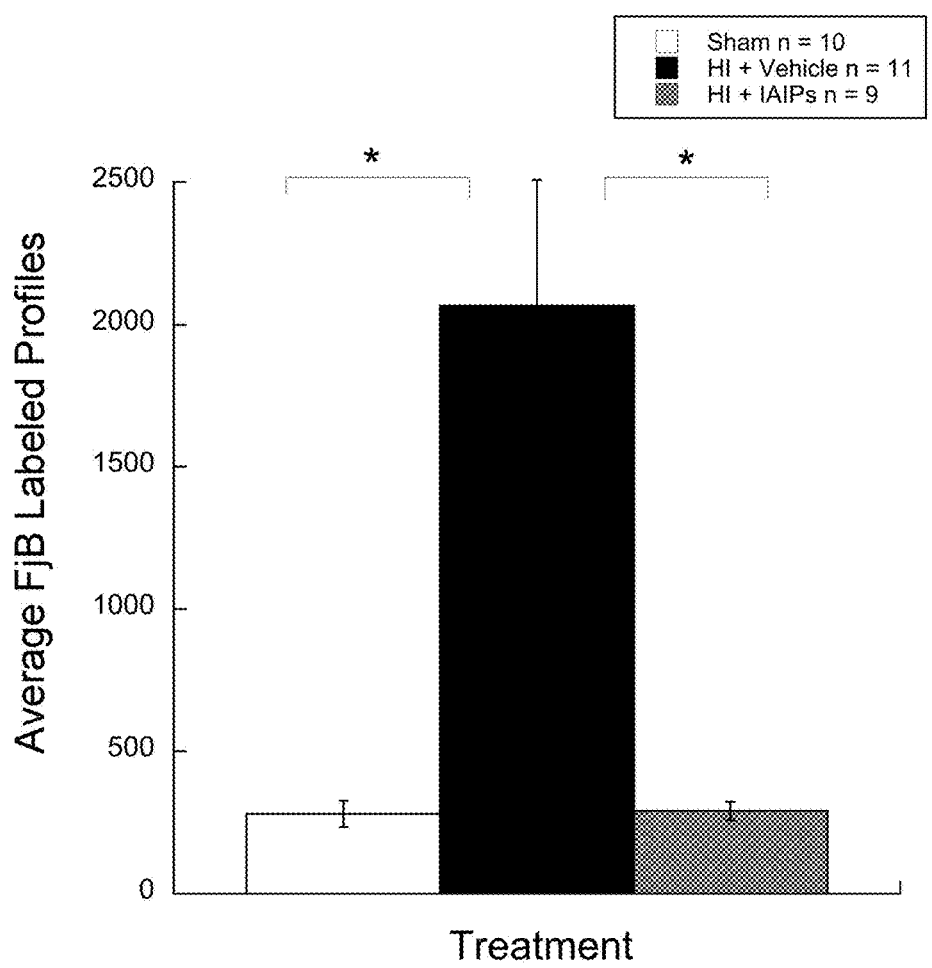
FIG. 5 is a graph showing average FjB labeled profiles.

In premature infants, IAIPs decrease during sepsis[66] and NEC.[67] In addition, both disorders are associated with an increased incidence of brain damage, suggesting the interesting possibility that decreases in IAIPs levels contribute to the development of associated brain damage.[47, 48] IAIPs attenuate ischemia-related white matter injury, as suggested by our data (FIGS. 4-6). IAIPs prevent inflammation-related white matter damage in the premature brain.

The subunit bikunin, purified from urine, has a very short half-life (3 to 10 min) in the circulation. In contrast, IAIPs isolated from blood represent native complexed forms of the protein, have a longer half-life (8-12 h), and thus, are more feasible as therapeutic agents. The neuroprotective properties of this natural form have only been examined in our studies and are likely to have considerably greater therapeutic efficacy than that of the bikunin subunit.[61, 65]

Sheep Model of Human Disease

The large amount of data on the fetal sheep brain is highly relevant to conditions in premature infants.[1, 68-76] A review[6] on the use of instrumented fetal sheep to define pathogenesis of human white matter injury supports our original contention that the immature sheep fetus is an excellent model for study of brain maturation.[74-80] The immature ovine brain (0.65 gestation or 95 days)[6] is similar to that of the premature human between ~24 and 28 weeks with respect to neurogenesis, cerebral sulcation, and detection of the cortical component of auditory and somatosensory evoked potentials.[81-84] Similar to findings in premature infants, the immature ovine brain has limited capacity for cerebral autoregulation, immature white matter, and very high water content.[6, 7, 85, 86] We, and others, have reported that white matter lesions similar to those in premature infants are more reproducible in sheep fetuses than in rodents.[5-7, 68] Importantly, the only major progress in prevention/attenuation of HI injury in human newborns was a direct result of studies done in the sheep fetus.[1, 72]

Example 6: Neuroprotective Effects of Systemic IAIP Administration on Brain Ischemia in the Ovine Fetus Our data demonstrate several important new results that suggest the feasibility and probable successful outcome of our aims.

1. Purification of IAIP from Sheep Serum.

Figure 8:
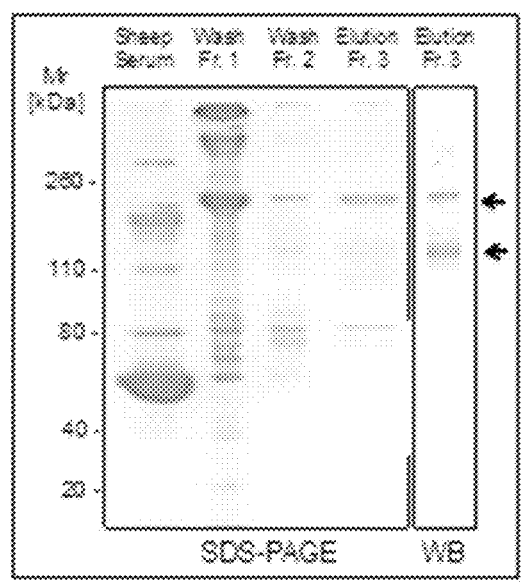
FIG. 8 is a photograph of a gel produced by SDS-PAGE, which shows 125 and 250 kDa bands in purified IAIPs from sheep serum.
Figure 9A:
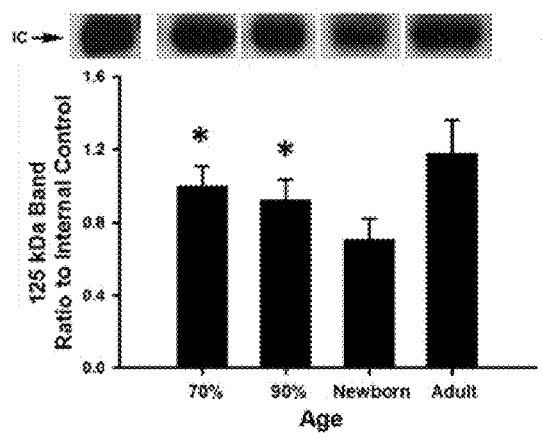
FIGS. 9A and 9B are graphs and insets showing detection of IAIP during gestation (70% and 90%) and in newborn and adult sheep.
Figure 9B:
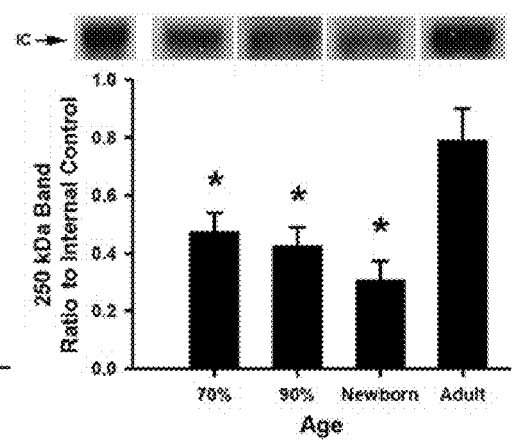

IAIPs will be extracted from ovine serum (Quad-Five, Ryegate, Mo.) using anion-exchange chromatographic separations on Tosoh Q and monolithic DEAE-CIM columns (Tosoh Q-600C-AR, Tosoh Bioscience, King of Prussia, Pa. and DEAE Convective Interactive Media, BIASeparation, Austria). We developed efficient separation methods for a high yield and purity of ovine IAIPs. Approximately 25-liter ovine serum will be extracted yielding ~4-5 g highly purified biologically active IAIPs for in-vivo fetal sheep studies. The SDS-PAGE shows 125 & 250 kDa bands in purified IAIPs from sheep serum (FIGS. 8 and 9A/9B). Serum was passed to anion-exchanger columns and washed with salt and low pH buffers (Fr. 1 and Fr. 2 of FIG. 8) before eluted in high salt (Fr. 3 of FIG. 8). Sheep IAIPs in this eluted fraction are ~85-90% pure. Western blot (WB) analysis with rabbit polyclonal antibody against IAIPs (R16) confirmed the reactivity of IAIPs (125 kDa Pre-alpha Inhibitor & 250 kDa Inter-alpha Inhibitor, arrows, FIGS. 8 and 9A/9B).

2. Detection of IAIP in Sheep.

To measure endogenous IAIPs quantitatively in biological fluids, we established a competitive ELISA using rabbit polyclonal antibodies against human IAIPs that cross-react with ovine species. Purified ovine IAIPs are used to coat micro plates for ELISAs. Using known standard IAIP amounts, we established a linear standard curve. This ovine IAIP ELISA will be useful in measuring IAIP levels in the studies below. We have shown that near term fetal sheep (90% gestation, 135 d, 55±27 µg/ml, mean±SD) have lower ($P<0.05$) plasma IAIP concentrations than newborn (111±38) and adult (102±46) sheep. IAIPs were also detected for the first time in brain, CSF, and CP from early in fetal and throughout ovine development as both 250 kDa and 125 kDa proteins. Expression of both proteins were higher in adult than fetal brain (FIGS. 9A/9B,*$P<0.05$ vs. adult, full-term gestation=148 d). In addition, high levels of IAIPs in fetal CSF and significant reductions ($P<0.05$) after birth suggest their importance to brain development. Although the functions of IAIPs in brain, choroid plexus, and CSF are not known, their presence in high amounts during development raises the interesting possibility that they are endogenous anti-inflammatory-neuroprotective molecules and suggests their importance in brain development.

3. IAIPs Attenuate Ischemic Brain Injury in the Ovine Fetus and HI Brain Damage in Neonatal Rats.

We exposed fetal sheep to ischemia/reperfusion.[4, 5, 88] Sections stained with Luxol fast blue-hematoxylin/eosin (LFB-H&E) to delineate white matter lesions showed homogeneous blue stained myelin and healthy appearing cerebral cortex in control (FIG. 4A,1×) in contrast to ischemic (FIG. 4B,1×) brains that exhibited decreased blue staining and cerebral cortical thinning indicating severe white matter and neuronal loss, respectively. Fetal sheep treated with IAIPs (4 mg/kg 15 min, 24 & 48 h after carotid occlusion; see, e.g., FIG. 4C, 1×) showed remarkable preservation of white matter and cerebral cortex. A pathologist, unaware of treatments, scored the sections according to the percentage of neuronal and white matter destruction using a grading system that we previously reported (FIG. 6).[4, 5, 88] The pathological scores indicated severe cerebral cortical and white matter injury in fetuses exposed to ischemia/reperfusion (closed bars) compared with control (open bars; $P=0.07$) and IAIP-treated ischemia/reperfusion (hatched bars, treatment as above). We also identified dramatic ischemia-related decreases in MBP and altered cellularity of GFAP positive astrocytes in this model.[5]

Example 7: Confirm the Neuroprotective Effects of IAIPs on Ischemic-Reperfusion Brain Injury in Fetal Sheep HI increases systemic and local pro-inflammatory cytokines, which in turn potentiate HI brain damage in the perinatal period.[91, 92] In stroke patients, elevated CSF cytokines[93] are associated with white matter damage.[93] IL-1β, IL-6, and TNF-α mRNA have been detected after cerebral ischemia in adult rats[94] and elevated cytokines were reported after HI in young rats.[95, 96] Intracerebral IL-1β or TNF-α injections result in brain injury in young rats, and IL-1β injures white matter.[97] Intracerebroventricular injections of an IL-1 receptor antagonist reduce cell death and caspase-3 activity in young rats after HI.[98] Thus, pro-inflammatory cytokines are upregulated by HI and damage the immature brain, and therefore reducing their activity attenuates injury-related damage. Further, IAIP treatment of newborn mice attenuates sepsis/inflammatory-related increases in systemic cytokines.[11] IAIP light chain subunit or UTI is cytoprotective against liver, intestine, kidney, heart, and lung ischemic-reperfusion injury through its anti-inflammatory activity, attenuates cerebral ischemia in an adult stroke model and white matter loss in an EAE model.[61, 65] Although these findings are encouraging, UTI has very short half-life (3 to 10 min) in contrast to the native complexed IAIPs (8-12 h), thus making IAIPs more useful as effective therapeutic agents. In the experiments below, we show that IAIPs systemically administered after exposure to in-utero brain ischemia attenuate development of ischemia-related injury in fetal brain. One of the mechanism(s) of potential neuroprotective effects could be down regulation of pro-inflammatory cytokines in brain parenchyma.

arterial blood pressure, amniotic fluid pressures, continuous ECoG, and separate sets of blood collection. At the end of the study, the ewe and fetus will be given intravenous pentobarbital (15-20 mg/kg) to achieve a surgical plane of anesthesia and 200 mg/Kg of pentobarbital for euthanasia. Blood samples (FIG. 13, solid circles) are obtained for hematocrit, blood gases, oxygen saturation, arterial glucose and lactate, IAIP concentration, and cytokines (IL1-β and IL-6).[99]

CSF samples are obtained for Western blot (IL1-β, IL-6, GFAP, MBP, and IAIPs). Coronal brain sections obtained at the level of the hypothalamus (mamillary bodies) for routine pathology (LFB-H&E) will be scored by a pathologist unaware of treatment (E.G.S.) as we previously described.[4, 5, 88] The remainder of the brain tissue will be used to determine some of the mechanism(s) of action of IAIPs according to the methods described below. After this section is obtained, half of the remaining brain will be taken for frozen tissue and the contralateral half for immunohistochemistry (NeuN, IL1-β, IL-6, TNF-α, activated caspase-3 (see FIG. 10), MBP, and GFAP). Separate frozen sections of cortex, caudate nucleus, cerebellum, hippocampus, thalamus, midbrain, and periventricular white matter will be obtained for Western blot (MBP, IL-1β, IL-6, TNF-α, and IAIP, MMPs) and ELISA (IL-6, IL-1β, caspase-3 and IAIP).

Data Analysis.

Using group means from our preliminary data, assuming equal sample sizes, 8/group (n=24) would give 95% power at an alpha of p=0.05 to detect significant differences. Hence, we require 6/group for the late (to supplement our data) and 8/group for the early gestation sheep. Serial measurements will be compared by ANOVA for repeated measures with time, treatment, and group as factors, brain samples for cytokines and MBP etc. by one-way ANOVA. If a significant difference is detected by ANOVA, the Fischer

TABLE 1

| Subjects | Gest. Age (days) | Placebo + Sham (# Animals) | Placebo + Isch (# Animals) | IAIP + Isch (# Animals) | Reper. (h) | Brain Tissue Exp. End Point |
|---|---|---|---|---|---|---|
| Early Gest. | 100-107 | 8 | 8 | 8 | 72 | Pathology/Immunohist |
| Late Gest. | 125-127 | 6 | 6 | 6 | 72 | Biochem/Molecular Bio |

Experimental Protocol:

Table 1 shows study subjects, gestational age at study, study conditions, # of animals, duration of reperfusion, and tissue end-points for the studies. Groups of early or late gestation fetal sheep will be studied because both premature and near term human infants develop CP. Control fetal sheep will be exposed to placebo-sham ischemia, experimental to in utero brain ischemia (carotid occlusion: 30 min) with and without IAIP treatment during 72 h-reperfusion). Surgical preparation and carotid occlusion will be performed as we previously described.[4, 5, 88] Brain tissue will be obtained for pathological assessment and scoring.

Figure 13:
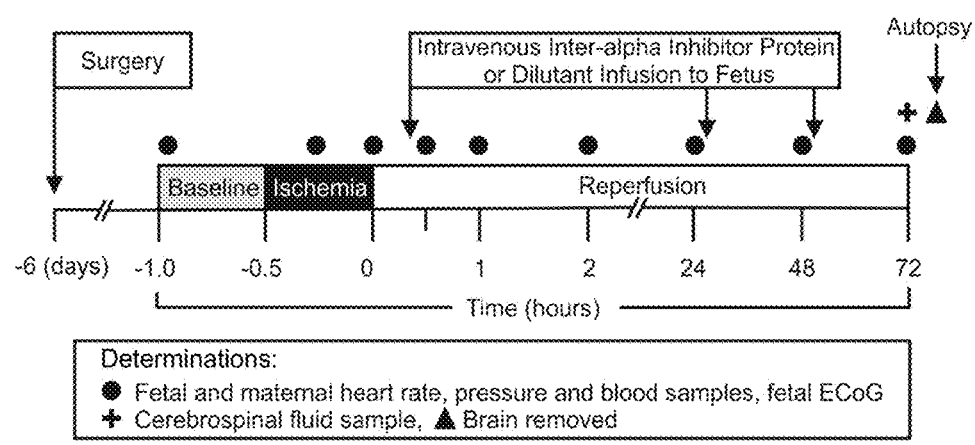
FIG. 13 As shown in the schema below, after baseline measurements & 30 min ischemia, fetal sheep will receive placebo or IAIP (4 mg/kg fetal weight) 15 min, 24 h and 48 h after the onset of reperfusion. This treatment regimen was selected because the 8-12 h half-life of IAIPs should provide fetal exposure to IAIPs for the majority of the 72 h reperfusion, and this dose appears efficacious in our preliminary data. Measurements obtained at baseline, during ischemia, after 30 min of ischemia, and sequentially during reperfusion (study design, solid circles) include fetal heart rate, mean arterial blood pressure, amniotic fluid pressures, continuous ECoG, and separate sets of blood collection. At the end of the study, the ewe and fetus will be given intravenous pentobarbital (15-20 mg/kg) to achieve a surgical plane of anesthesia and 200 mg/Kg of pentobarbital for euthanasia. Blood samples (study design, solid circles) are obtained for hematocrit, blood gases, oxygen saturation, arterial glucose and lactate, IAIP concentration, and cytokines (IL1-β and IL-6).[99]

As shown in the schema of FIG. 13, after baseline measurements & 30 min ischemia, fetal sheep will receive placebo or IAIP (4 mg/kg fetal weight) 15 min, 24 h and 48 h after the onset of reperfusion. This treatment regimen was selected because the 8-12 h half-life of IAIPs should provide fetal exposure to IAIPs for the majority of the 72 h reperfusion, and this dose appears efficacious in our preliminary data. Measurements obtained at baseline, during ischemia, after 30 min of ischemia, and sequentially during reperfusion (FIG. 13, solid circles) include fetal heart rate, mean LSD test will be used as a post hoc test. Apoptotic cells/mm$^2$ will be detected as described.[100] The # of apoptotic cells/mm$^2$ or NeuN positive cells will be analyzed by ANOVA and pathological/immunohistochemical samples by non-parametric methods.

Results-Interpretation.

We anticipate that IAIPs will reduce ischemic brain damage in the early and late gestation fetal sheep by at least 50% given our data. We anticipate that there will be less seizure activity in the fetuses exposed to IAIP-brain ischemia compared with those exposed to placebo-ischemia. We anticipate that ischemia-related white matter and neuronal injury will be attenuated in IAIP treated fetuses as suggested in FIGS. 4-6.

Alternative Procedures.

Methodologies described above are routine in our labs. Although we elected to use the carotid occlusion model, an alternative model of umbilical cord occlusion may be used in future studies to examine IAIPs beneficial effects on brain and injury to other organs.[3] The dosing protocol that we selected appears beneficial. Other treatment doses, regimen, and durations may also be used.

IAIPs are large molecules that might not easily cross the blood-brain barrier (BBB). However, IAIP-related molecules have been shown to be neuroprotective against focal cerebral ischemia-reperfusion injury[61] and it remains possible that under pathological conditions, similar to the situation with antibodies,[101-106] these molecules could enter the brain and have therapeutic effects. However, the two most likely mechanisms by which IAIPs could protect the brain are by reducing the concentrations of intravascular cytokines generated during brain ischemia/reperfusion,[107, 108] and/or reducing ischemia-related increases in endothelial derived cytokines that could leak into brain via a damaged BBB to accentuate brain injury.[107] Nonetheless, we recognize that it would be of great interest to measure BBB permeability with IAIPs under normal and pathological conditions.

Example 8: Examination of Some of the Mechanism(s) of Action and Biological Effects by which IAIPs Attenuate Ischemic-Reperfusion Injury in the Immature Brain Our data show that IAIPs exhibit mechanism(s) of action as a neuroprotectant in fetal brain. The approaches described herein can be used to further identify potential mechanisms by which IAIPs attenuate brain damage in the fetus.

1. IAIPs & Ischemia.

We have shown that ischemia-reperfusion results in acute decreases in IAIPs 4 h after ischemia (I/R, *P<0.05 vs. control, FIG. 3), which return toward control values (open bars) 24 & 48 h after ischemia. We do not know the mechanism for the reductions in IAIPs, but IAIP levels can be measured in fetuses exposed to ischemia with and without IAIP-treatment to determine if IAIP brain expression is higher after IAIP-treatment.

2. Ischemia Increases Pro-Inflammatory Cytokines in Ovine Fetus.

We recently reported using the same fetal model that cerebral cortical IL-1β was higher 48 & 72 h after ischemia compared with non-ischemic fetuses, and IL-1β & IL-6 levels were higher in white matter than in cerebral cortex 72 h after ischemia.[50] Here we will examine the expression of IL-1β, IL-6 & TNF-α in fetuses exposed to ischemia with and without IAIP treatment.[50]

3. Ischemia Increases Caspase-3 in Ovine Cerebral Cortex.

Figure 10:
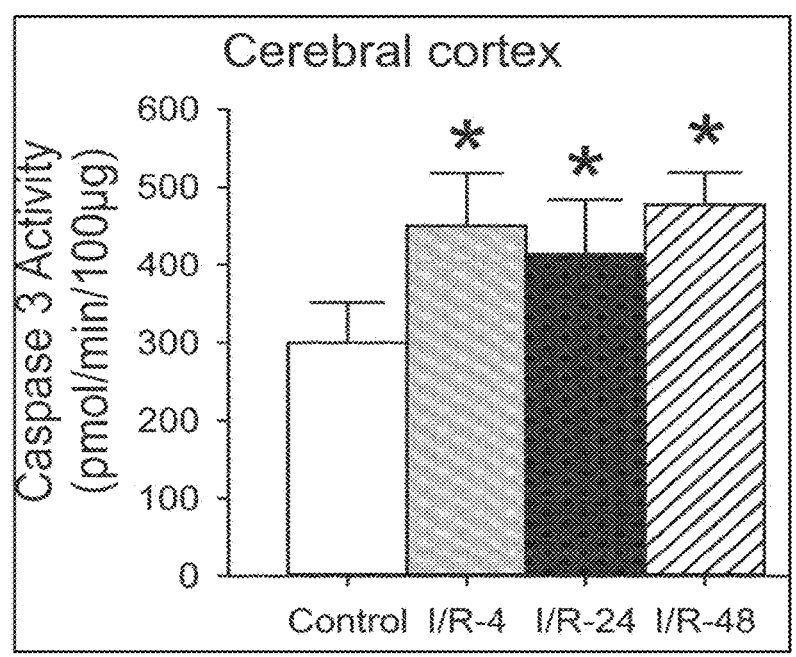
FIG. 10 is a graph showing an increase in the activity of a pro-inflammatory cytokine (caspase 3) in the cerebral cortex of sheep brain in control and I/R-treated animals (after 4, 24, and 48 hours).

Increases (*P<0.05 vs. Control) in caspase-3 were detected[109, 110] 4, 24 & 48 h after ischemia (FIG. 10). We do not know if caspase-3 is elevated 72 h after ischemia, but will measure it in the current studies.

Figure 11:
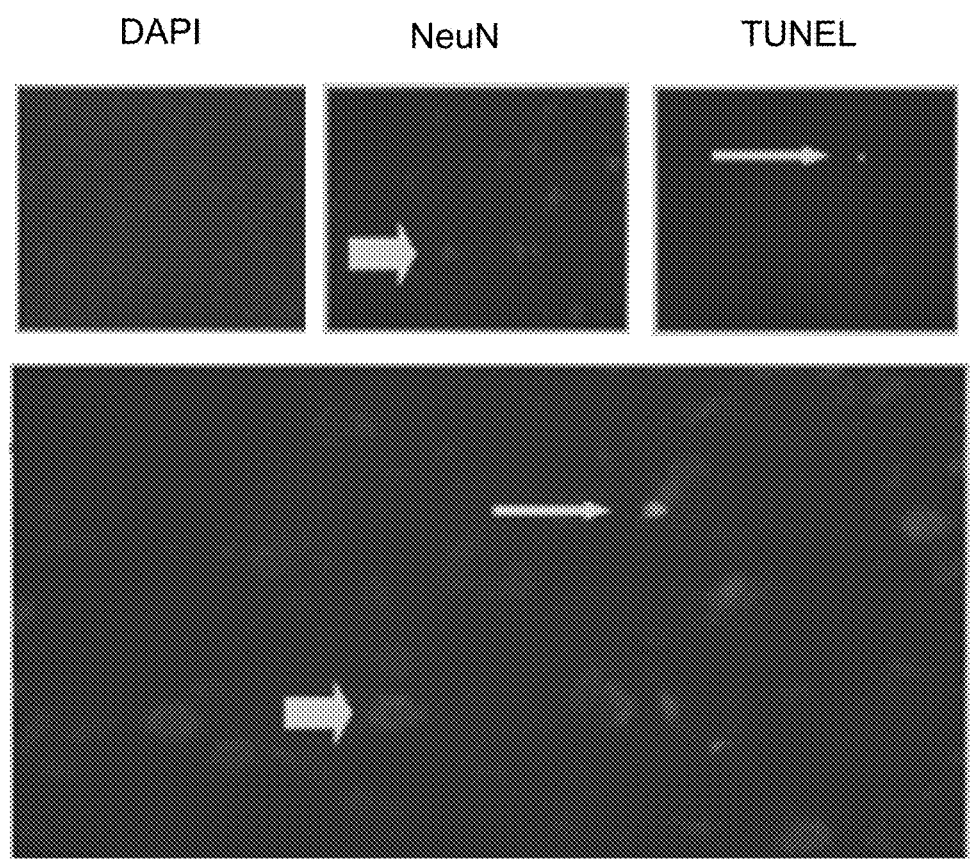
FIG. 11 is a set of photographs showing that neuronal and non-neuronal apoptosis in the ovine fetus can be quantified using NeuN is a neuronal marker, TUNEL staining to show DNA fragmentation (apoptosis), and DAPI staining to show nuclei.

4. Double-Label Immunofluorescence: Neuronal & Apoptotic Cellular Counts. Caspase-3 is a key executioner of apoptosis.[111] We used NeuN is a neuronal marker,[112] measured DNA fragmentation (apoptosis) with terminal deoxynucleotidyl transferase-mediated dUTP nick end labeling (TUNEL), and all nuclei with DAPI in fetal brain to quantify neuronal and non-neuronal apoptosis in the ovine fetus.[100] FIG. 11 shows DAPI labeled nuclei, NeuN positive nuclei (thick arrow), and a TUNEL positive apoptotic nucleus (thin arrow). Merged lower portion shows a NeuN positive nucleus, which is not apoptotic (thick arrow), and a nucleus exhibiting co-localization of green fluorescein apoptotic, red NeuN antigen, and blue DAPI nuclear DNA markers indicating this is an apoptotic neuronal nucleus (thin arrow).[100] Using these techniques, we will quantify total number of surviving neurons and amount of apoptosis in neuronal and non-neuronal nuclei of ischemic brain tissue from fetuses with and without IAIP treatment.[100]

Our experimental approach will analyze some of the mechanism(s) by which IAIPs exert their beneficial effects on ischemic-reperfusion brain injury in fetal sheep. Analyses below will be performed on the brain tissue from fetuses. The purpose is to begin to elucidate some of the biological effects of IAIPs and potential mechanism(s) underlying the neuroprotection suggested by our data. To this end, we will use methodologies we published or are available in our laboratories.[5, 100] This approach addresses three key questions based upon our data: 1) Does exogenous IAIP administration affect brain tissue IAIP & CSF levels? 2) Do IAIPs quantitatively attenuate ischemia-reperfusion-related neuronal and white matter loss? and 3) Do IAIPs attenuate ischemia-reperfusion related increases in cytokines and MMPs?

TABLE 2

| Brain Regions Hippocampus, Caudate-Putamen, Frontal & Parietal Cortex | | White Matter Regions (WM) | |
|---|---|---|---|
| Morphological- | | Subcortical & Deep WM, Corpus Callosum | |
| Immunohistochemical | Biochemical/Molecular | Morphological | Biochemical/molecular |
| Neuronal cell counts (NeuN), In situ DNA fragmentation (ApopTag), Caspase-3 | DNA fragmentation, Caspase-3 activity, MMPs 2, 3 & 9 Western blot: IAIPs, Casp. 3, MBP, GFAP, IL-6, IL1β, TNF α, IL-6 | MBP, GFAP, PLP | DNA fragmentation, Caspase-3 activity, Western blot: IAIPs Caspases, MBP, PLP, GFAP, IL-6, IL1β, TNF α |

We will also determine some of biological effects/mechanisms of IAIPs protection in brain ischemia. We will examine specific brain and white matter regions as listed for neuronal and white matter (WM) markers of injury in tissue from fetal sheep exposed to sham control or ischemia with and without IAIP treatment. We will examine brain (hippocampus, caudate-putamen, frontal, and parietal cortex, Table 2) and white matter regions (subcortical and deep WM, corpus callosum) that could be influenced by IAIP treatment.[4, 5, 88] Western blot will be used to measure IAIPs in brain (FIGS. 3, 8, and 9A/9B) and CSF, cytokines as we described,[50] proteolipid protein (PLP) as described,[115] MBP and GFAP, after myelin isolation, with standard techniques.[114]

Data Analysis:

Multivariate ANOVA will be used to assess differences between total number of dying cells, total # of neurons, apoptotic neurons, and other markers in the Table 2 across brain regions among experimental conditions (control, placebo-ischemia and IAIP-ischemia), and one-way ANOVAs for individual brain regions for Western blots, MMPs, caspase activity etc. Post hoc testing will be similar to Aim1. These analyses will reveal any subtle differences in brain markers in the Table 2 across treatment conditions.

Results-Interpretation.

Based upon our data, we expect that neuronal loss will be less, total neuronal number (NeuN) higher, apoptosis/caspase-3 lower, MMPs lower, MBP & PLP higher, GFAP and cytokines lower, and IAIPs higher in the brain of IAIP—than placebo-treated ischemic fetuses. Results of these studies will give us some indication of mechanisms by which IAIPs exert their neuroprotective effects allowing for a larger proposal focused upon IAIPs' mechanisms of action.

Alternative Procedures.

We would like to determine oligodendrocyte lineage in the placebo- and IAIP-treated ischemic brain. If the above results suggest IAIPs attenuate WM damage, we will consider this approach. In addition, if we find higher IAIP levels in the brains of IAIP-treated fetuses, we may seek to determine the mechanism by which IAIPs gain access to the brain.

Specific Methods:

ELISA IL-6 & IL-1β and IAIP. IL-6, IL-1β and IAIP protein concentrations will be measured in blood by ELISA.[99] IAIP concentrations will be measured by a competitive ELISA (ProThera Biologics). Purified ovine IAIP will be immobilized on 96-well microplates. Rabbit anti-IAIP (R-16) will be added to samples and incubated on the well for 1 h at RT. After washing, secondary HRP-conjugated anti-rabbit Ig (Invitrogen) will be incubated for 1 h. One-step TMB will be used as a substrate and color changes measured on spectrometer. The IAIP concentrations in samples are calculated against a known IAIP standard.

Example 9

Perinatal hypoxic-ischemic injury (HI) is the leading cause of mortality and long-term neurologic morbidity in premature and term infants with pregnancy and/or birth complications.[1-3] Although HI may be acute or chronic, affected children often develop long-term cognitive and behavioral deficits.[4-11] Moreover, severity of injury and pathological outcome are dependent upon sex, with increased incidence and more severe long-term deficits in male than in female infants.[12-18] The mechanism(s) of these sex differences are largely unknown; however, recent data indicate sex differences in cell death and extent of tissue damage after HI.[19-24] These differences suggest that neuroprotective strategies should be tailored differentially by sex for maximal benefit. We seek to increase knowledge of the mechanism(s) of sex differences in HI, and to determine the comparative effects of IAIPs in sex-related differences of HI.

To determine mechanism(s) of sex differences in HI injury and neuroprotection, we will examine pro-inflammatory cytokine expression (known to cause and/or accentuate brain injury)[25-27] and the differential neuroprotective effects of IAIP, which is known to down-regulate cytokines in a sepsis model.[28] Mechanistic determinations include molecular, immunological, immunohistological, and long-term behavioral outcomes in male and female rats after HI. Our data show IAIP depletion after ischemia in fetal sheep brain[29] and IAIP treatment to be the most neuroprotective strategy examined to date in neonatal male rodents. However, given evidence of sex differences in mechanisms of and long-term outcomes after H1, the expression of endogenous IAIP may differ between the sexes after HI. Through histological and long-term behavioral study of both male and female rats, our studies examine sex differences in cytokine and IAIP expression after HI, and determine the modulation of key differences in cell death by this exciting neuroprotective agent. IAIP is poised to enter clinical trials for sepsis and related molecules suppress preterm labor,[30-32] and thus this therapeutic agent could rapidly enter clinical use to attenuate HI injury in infants. We predict a sexually dimorphic response due to key modulators involved in sex-specific mechanisms of H-related cell death.

We propose experiments to determine IAIP and cytokine concentrations in serum and brain of male and female rats at 2, 4, 6, 8, 24 h and 7 d after HI injury. Given increased damage and deficits for males, we hypothesize that serum and brain tissue cytokine levels are higher, and IAIP depletion greater, in male rats than female rats after HI.

We also propose to examine the neuroprotective effects of exogenous IAIP treatment given immediately and 24 h after HI using histological and long-term behavioral measures to determine the mechanism(s) by which IAIP is neuroprotective. We hypothesize that IAIP treatment (30 mg/kg×2)[25] decreases neuronal death and microglia activation in rats exposed to HI, and that treatment is more efficacious in male than female rats. The acute effects of HI and IAIP treatment can be measured with Fluoro Jade B (FJB; dying neurons) and EDI (activated microglia), along with IAIP modulation of sex related mechanism(s) of cell death, including caspase 3 and poly (ADP-ribose) polymerase 1 (Parp1) activity, Long-term behavioral outcome can be evaluated by Morris Water Maze performance (Aim 2b).

Background:

HI is a major cause of infant brain injury with an occurrence of 2-4/1000 full term and 5-6/1000 premature infants,[33-34] though incidence and outcome appear dependent upon sex. The clinical origin of this difference derives from increased rates of vascular/neurologic complications (i.e., intra-cranial bleeds, HI complications of delivery) in male versus female neonates, as well as superior cognitive recovery by females following HI injuries of comparable severity.[35] Although the cause(s) of these sex dependent differences are largely unknown, recent evidence suggests cell death mechanisms differ between the sexes, indicating the cascade of detrimental events induced by HI may differ for males and females.[19-24] Moreover, these findings suggest male and female neonates would likely respond differently to neuroprotective strategies. Although research on sex differences in incidence and outcome of adult stroke is rapidly expanding, there is a paucity of information related to this important aspect of brain injury in neonates. Therefore, addressing the importance of sex in response to early HI injury is important.

Though the majority of neonatal HI research has almost exclusively studied male subjects, recent data demonstrate sex differences in intrinsic cell death pathways[19-24] as well as influences of the hormonal milieu on the response to HI injury.[36-38] Specifically, data indicate differences in the proportional activation of two apoptotic pathways (caspase-independent and -dependent) following HI.[19,39] Male HI mice display increased Parp1 (an enzyme essential to the caspase-independent pathway) relative to females, while caspase-3 (active in the caspase-dependent pathway) is present in higher concentration in HI female mice than male.[20] Likewise, Parp-1 knockout benefits HI males, but not females,[21] while caspase inhibition is neuroprotective to HI female (but not male) animals.[22,23] These studies emphasize the importance of expanding our understanding of the cause of increased deficits and poorer outcomes in males-both in infants[12-18, 35] and in animal models.[24, 38] Given these apparent differences, it is likely sex-related differences will also be observed in underlying molecular and cellular features of cell death and tissue damage after HI. Notably, pro-inflammatory cytokines are an important component of the cascade that causes and/or accentuates brain injury,[25-27] while IAIP has been shown to effectively down-regulate cytokines in neonatal and adult sepsis models.[28] However, the potential sex-related differences in timing of cytokine activation (a certain contributor to injury), particularly with reference to utilization of endogenous IAIP levels in the brain is not known, nor has it been studied between the sexes. Thus, we seek to compare potential differences in brain cytokine and IAIP concentrations both in control and HI exposed male and female animals.

Cytokines are elevated intravascularly and in cord blood of infants who later developed cerebral palsy,[40] in amniotic fluid of premature infants who later developed white matter lesions,[41] and in white matter from infants who died of periventricular leukomalacia,[42] the foremost predictor of cerebral palsy in human infants.[43-44] Furthermore, IAIP was shown to increase survival in a neonatal rodent model of sepsis, in part by down regulating pro- and up regulating anti-inflammatory cytokines.[28] Additionally, pretreatment with IAIP subunit, bikunin (purified from urine and having a short 3-10 min half-life), is neuroprotective against stroke injury in adult rats[26] and attenuates white matter damage in an adult model of autoimmune encephalomyelitis (EAE).[45] In contrast, the IAIP used here (isolated from blood and with a significantly longer half-life, 8-12 h) represents the native complex form of the protein and is therefore feasibly a more effective neuroprotective agent.

IAIP treatment may attenuate or prevent brain damage in infants with HI by reducing pro- and enhancing anti-inflammatory cytokines. In fact, decreased IAIP has been shown to accurately predict the development of sepsis in premature infants, whereas excreted IAIP-related fragments suggest these proteins are rapidly consumed during sepsis.[46] Importantly, sepsis is a significant predictor of brain damage in premature infants.[47-48] Moreover, increased IAIP levels in healthy adult male plasma (in relation to female) suggest males may require increased IAIP due to increased sensitivity to inflammation.[49] Additionally, Parp1 plays a crucial role in systemic inflammatory shock[50] and has been shown to enhance expression of pro-inflammatory mediators in models of sepsis,[51] thus indicating IAIP treatment may preferentially protect males given their predominant use of Parp1-mediated cell death pathway. However, this response remains to be determined in neonates of both sexes. Examination of the comparative benefits of IAIP administration and mechanism in male and female rats after HI injury is also important.

We seek to increase understanding of sex-related differences in the mechanisms of neonatal HI; and, for the first time, examine the effect of a neuroprotective agent, IAIP, in neonatal rodents of both sexes using histological, immunological, and long-term behavioral measures. Pro-inflammatory cytokines have not been quantified, nor have the putative neuroprotective effects of exogenous IAIP treatment been compared in the brains of male and female rats after HI. We seek to determine why the sexes respond differently to neonatal HI, and will determine some of the underlying mechanisms for these differences. Finally, our data may suggest sex differences in cellular functioning after early brain injury, indicating the importance of attention to sex in the development of optimal neuroprotective therapies for neonates.

Sex differences in long-term behavioral outcome after HI: Our data on the long-term behavioral outcome of male and female rats with P7 HI show significant deficits in a modified prepulse inhibition paradigm for male HI animals only.[24,38] Deficits were elicited in female HI animals only when treated with early testosterone[38] or embelin,[24] an inhibitor of X-linked inhibitor of apoptosis (XIAP). IAIPs are known to block apoptosis by binding to caspases in the caspase-dependent, predominately female activated pathway. Treatment preventing this endogenous inhibition results in HI-related damage and deficits in females only. It is likely sex differences also exist in pro-inflammatory cytokines in response to HI and because Parp1 has been shown to mediate inflammatory responses, we predict therapeutic IAIP intervention to vary by sex.

IAIP Expression in the Ovine Fetal Brain: Effects of Ischemia.

Our data suggests age-dependent expression of IAIP, as plasma concentrations are higher in adult and newborn sheep than fetuses at 70% and 90% gestation.[53] Data also show substantial ischemia-induced decreases in IAIP 4 h after ischemia in the ovine fetus as measured by Western blot (FIG. 3, inset)[29] obtained using a specific polyclonal antibody against human IAIP that cross-reacts with non-human IAIP, including sheep and rat IAIP. The rapid decrease in IAIP during ischemia-reperfusion could be due to consumption of cortical IAIP, suggesting that IAIP is utilized/broken down during ischemia. This phenomenon raises the interesting possibility that IAIP acts as an endogenous anti-inflammatory molecule and that treatment with exogenous IAIP after ischemia could be an effective neuroprotective strategy. This concept is also supported by evidence of neuroprotection by the short acting subunit, bikunin, in EAE.[45]

Neuroprotective Effects of IAIP in Neonatal Male Rats.

Figure 2:
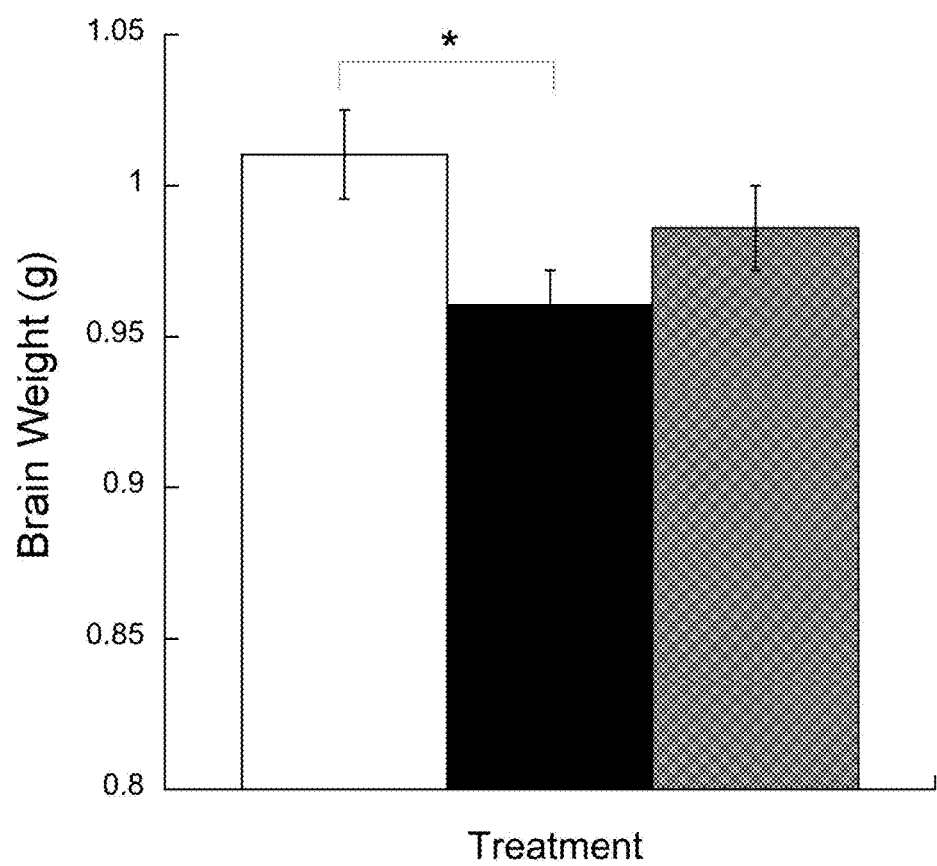
FIG. 2 is a graph showing brain weight in rats following sham treatment, placebo treatment, and treatment with IAIP. Significant reduction in brain weight in vehicle HI animals (n=11, black bar) compared to sham (n=10, white bar) is shown. No significant reduction in IAIP-treated HI animals is shown.

Our exciting preliminary data demonstrates substantial neuroprotective effects of IAIP treatment for male rats with neonatal HI.[52] Data indicate considerable neuroprotective properties of IAIP as exogenous treatment after ischemic surgery, but before hypoxia, inhibits loss of cortical tissue measured by total brain weight (FIG. 2) and dramatically reduces the number of dying cerebral cortical neurons measured by FJB staining (FIG. 1). IAIP treatment occurs after HI induction to show the translational relevance of our model to treatment in humans.

Figure 12:
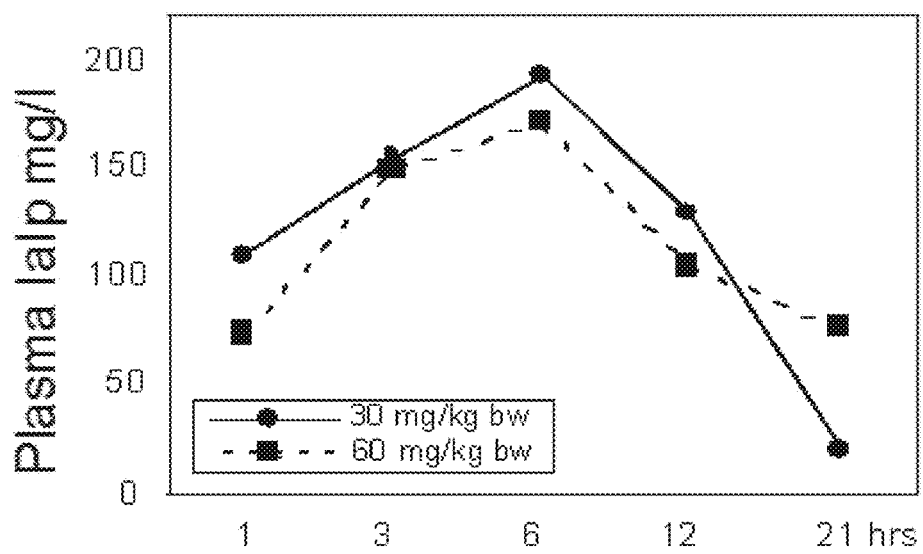
FIG. 12 is a graph showing that IAIP plasma levels in mice peaked 6 h after injection (at both 30 mg/kg and 60 mg/kg body weight (bw) and decreased by 24 h. IAIP concentration was detected using a competitive ELISA assay with monoclonal antibody 69.31 specific against the light chain of human IAIP.

Kinetics of Intraperitoneal Administration of IAIP in Healthy Newborn Mice:

We performed preliminary absorption and kinetic studies of i.p. (30 or 60 mg/kg) purified human IAIP in P6 mouse pups. Five animals were used per IAIP dose and each animal per group sacrificed at 1, 3, 6, 12, and 21 h after injection. Trunk blood collected individually was analyzed for IAIP concentration using a competitive in house ELISA developed by YPL. Monoclonal antibody 69.31, specific against the light chain of human IAIP, detects systemic human IAIP in the mouse. IAIP levels peaked 6 h after injection in both groups and decreased by 24 h (FIG. 12). There was no difference in the level of IAIP in the two groups, suggesting a limitation of IAIP absorption in mice. Nevertheless, results suggest that more than one IAIP injection may be needed to achieve optimal neuroprotective effects and that 30 mg/kg is an appropriate dose for our studies. Human IAIP is to be used and detection of IAIP with this ELISA assay will be similar in neonatal rats.

Hypoxic-Ischemic Insult:

Time-mated Wistar rats will be used. On P1 litters will be culled to 5 males and 5 females to reduced variability in nutrition and maternal care between litters. On P7, HI pups will be anesthetized with isoflurane (2% induction, 1% maintenance), an incision made along the midline of the neck (approximately 0.5 cm), and the right common carotid artery exposed and cauterized. The incision will be sutured and pups allowed to recover. Sham animals will receive incision only. All procedures will be done on a heating pad and temperature closely monitored. Pups will be individually marked for identification by footpad ink injections. After the litter has recovered, pups will return to the dam for feeding (~2 h). HI subjects will then be placed in an airtight chamber, through which humidified 8% oxygen will flow for 120 m. A heating pad under the chamber provides warmth and pup temperature will be monitored. Sham animals will be placed in an identical container, without a lid or reduced oxygen flow, for 120 m. Upon completion, the entire litter will be returned to the dam. CAH has routinely performed this procedure with excellent survivability.

Methods:

Both HI and sham procedures, as well as sacrificing times after HI/sham procedure, will be balanced within litter (Table 3). Because HI results in extensive tissue damage to the ipsilateral hemisphere, an increased number of HI animals are needed for sufficient tissue for analysis. The duration of survival after HI is based upon our data showing greatest decrease in IAIP 4 h after ischemia.[29] Because we seek to determine the detailed time course of the pattern of cytokine and IAIP expression after HI, brains will be harvested at the above specified time intervals by rapid decapitation and snap frozen. Trunk blood will be collected for plasma assays.

TABLE 3

|      | Male Sham | Female Sham | Male HI | Female HI |
|------|-----------|-------------|---------|-----------|
| 2 h  | n = 6     | n = 6       | n = 10  | n = 10    |
| 4 h  | n = 6     | n = 6       | n = 10  | n = 10    |
| 6 h  | n = 6     | n = 6       | n = 10  | n = 10    |
| 8 h  | n = 6     | n = 6       | n = 10  | n = 10    |
| 24 h | n = 6     | n = 6       | n = 10  | n = 10    |
| 7 d  | n = 6     | n = 6       | n = 10  | n = 10    |

Tissue Processing:

Frozen cortical samples extracted from each brain hemisphere will be pooled with brain tissue from like-treated, same sex animals for IAIP analyses by Western immunoblot. Trunk blood from like-treated, same sex animals will be collected and pooled for ELISA analyses for plasma IAIP and cytokine concentrations.

Western Immunoblot:

IAIP determination in tissue: Aliquots for equal protein loading (50 µg/well) will be fractionated using 4-12% BIS TRIS SDS-polyacrylamide gel (Invitrogen) electrophoresis and immunoblotted onto PVDF membrane (Polyvinylidene difluoride, 0.2 micron, Bio-Rad Laboratories) using a semi-dry technique. Immunoblots will be blocked with a solution of 10% milk and 90% Tris-buffered saline with 0.1% Tween-20 solution (TBST) for one h at room temperature (RT), washed three times in TBST for 10 m/wash, and probed overnight with primary 1:5000 rabbit polyclonal primary antibody (ProThera Biologics) at 4'C. Next, immunoblots will be washed three times with TBST for 10 m/wash, and incubated for one h with 1:10000 goat anti-rabbit horseradish peroxidase conjugated secondary antibody (Alpha Diagnostic) at RT. After four washes in TBST at 10 m/wash, immunoblots will be developed using enhanced chemiluminescence solution (ECL Prime, Western Blotting Detection Reagents, Amersham Pharmacia Biotech, Inc.) before exposure to autoradiography film (Phoenix Research Products). Molecular weight standards (Bio-Rad Laboratories) will be included in each immunoblot. A human IAIP standard will be used as a positive control for all immunoblots to establish with certainty that proteins identified in rat tissue are the same as the known proteins. IAIP bands (125 and 250 kDa) intensities will be analyzed with a Gel-Pro Analyzer (Media Cybernetics). The experimental densitometry values will be normalized to beta actin. Group samples will be analyzed on at least two Western immunoblots.

Caspase-3 Determination in Tissue:

Protein concentration will be determined using the methods published by Whitaker and Granum[54], adapted for microplates.[20] Pro-caspase 3 is measured at 32 kDa and cleaved caspase 3 measured at 29 kDa.

Parp-1 Determination in Tissue:

Formation of PAR polymers via nuclear protein modification is a marker of Parp1 activity and will be measured by Western blot using rabbit anti-PAR polyclonal antibody LP96-10 (Biomol, SA-276).[21]

ELISA Assay:

IAIP determination in plasma: Purified rat IAIP will be immobilized on a microplate at RT for 1 h. Wells will be blocked with 5% non-fat dried milk for 1 h then washed with PBS+0.05% Tween 20 (PBS-T). Samples will be diluted in PBS and rabbit polyclonal antibody against IAIP (R-16) added and incubated for 45 m. IAIP present in the sample will compete with the immobilized IAIP on the plate for antibody binding. After washes with PBS-T, HRP-conjugated goat-anti rabbit IgG will be added and incubated for 30 m. Bound antibodies will be visualized by adding One-Step TMB Substrate Solution and color change will be read using a 650 nm filter on a spectrometer. IAIP levels in samples will be calculated against the standard curve included in the assay using an IAIP solution with known concentration.

Cytokine Determination in Tissue:

Protein concentrations of IL-6, IL-10, TNF-α, and IL-1β will be measured in brain samples by ELISA. Samples will be transferred to 10 ml conical micro tubes and combined with homogenization buffer consisting of 20 mM Tris-HCL, pH 7.4; 2.0M NaCl; 1 mM EDTA; 1 mM EGTA; 0.5% Deoxycholate; 1% Igepal; proteinase inhibitor cocktail (1 mM PMSF and 1 mg/ml of each of the following, Aprotinin, Leupeptin, Pepstatin A). After sonication for 1 min and centrifugation at 14,000 rpm for 30 min at 4° C., the total protein content of the supernatants will be determined with an assay kit (Pierce, Rockford, Ill.). The IL-6, IL-10, TNF-α, and IL-1β content of supernatants will also be performed by ELISA. An ELISA scanner (Thermo Fisher Scientific) will be used to measure the optical density of the total protein at 562 nm, and IL-6, and IL-1β at 450 nm. Antibodies to rat IL-6, IL-10, IL-1β, and TNF-α against different epitopes are available and will be used in cytokine-specific ELISA's.

Cytokine Determination in Plasma:

Quantikine ELISA kits for IL-6, IL-10, TNF-α, and IL-1β are available (R&D Systems) and will be used for plasma cytokine analysis.

Analysis:

Results will be expressed as mean±SD. Multivariate analysis of variance (ANOVA) will be used to determine the effect of HI on IAIP expression and cytokine concentration in the ipsilateral (injured) versus the contralateral cerebral cortices, where the specific factors are Ipsilateral/Contralateral, Treatment (sham/HI), Sex (male/female) and Time after HI (2, 4, 6, 8, 24 h, 7 d). If a significant difference is detected by ANOVA, the Fischer least significant difference test will determine differences among the hemispheres, time after HI, and sex differences among the different groups. Further, the relationship between IAIP expression and cytokine concentration after HI will be examined by correlational analysis with dummy coding variables to adjust for the different time periods. $P<0.05$ will be considered statistically significant.

Investigation of the Putative Neuroprotective Effects of Exogenous IAIP Through Histological Measures.

Methods:

I.P. injection of 30 mg/kg IAIP in 100 µL NaCl solution or 100 µL NaCl vehicle will be given immediately after induced HI (i.e., upon release from the hypoxic chamber; see Table 4), and 24 h later. This dose and schedule was selected based on preliminary data indicating neuroprotection in male rats undergoing HI, ELISA determinations in mice, and previous studies showing improved survival rates after systemic infection.[25] The current design is proposed with translation to clinical practice in mind and IAIP is therefore being given after injury. At 72 h after HI, all subjects will be overdosed with pentobarbital and perfused with 5 ml cold (4° C.) PBS followed by 5 ml 4% paraformaldehyde. A 72 h endpoint was chosen to ensure assessment of the inflammatory response to injury (often delayed compared to the molecular events relating to necrosis (6 h) and apoptosis (24 h).

TABLE 4

|  | Male | Female |
| --- | --- | --- |
| Sham Vehicle | n = 10 | n = 10 |
| Sham IAIP | n = 10 | n = 10 |
| HI Vehicle | n = 10 | n = 10 |
| HI IAIP | n = 10 | n = 10 |

Histological Processing and Stereological Assessment:

Serial sections will be cut using a vibrating microtome. Every fifth slice will be mounted and labeled for generalized neuronal cell death using FJB, while every sixth slice will be labeled for activated microglia using EDI. Processed tissue will be digitized and visualized using a Zeiss AxioImager M2 microscope system with color camera, remote stage, and Windows-based PC using StereoInvestigator software (Burlington, Vt.). Whole numbers of degenerating neurons and activated microglia (from cerebral cortex, thalamus, hippocampus, and basal ganglia) will be estimated, blind to treatment, using the Optical Fractionator probe in StereoInvestigator.

Statistical Analysis:

A multivariate ANOVA will be used to assess the differences between total number of dying cells and total number of activated microglia across brain regions between experimental conditions and across sex. Simple effects analyses for each sex will involve one-way ANOVAs for individual brain regions for both counts. These analyses will reveal any subtle differences in cell death markers or microglia activation across groups.

Investigation of the Putative Neuroprotective Effects of Exogenous IAIP Through Long-Term Behavioral Measures We also seek to investigate the potential long-term neuroprotective effects of IAIP treatment on behavioral performance. The Morris Water Maze (MWM) task requires the identification of a submerged platform using spatial (extra-maze) cues and examines learning and spatial reference memory. Rats will undergo insult and IAIP treatment. Animals will be housed with dams until weaning at P21, pair housed until P50, and single housed in adulthood. Animal weight will be recorded daily as an initial measure of IAIP side effects.

Water Escape (P34):

Each rat will be released at the end of an oval tub and required to swim to the opposite end to a visible escape platform. Rats will be guided to the platform if they have not located it after 45 s, and will remain there for 10 s. This procedure is used to assess any group differences in baseline motor behavior.

Morris Water Maze (P35-39):

The maze consists of a round tub with a submerged platform in a fixed location and extra-maze cues (shapes painted on walls, the doorframe, etc.) Each rat will enter at one of four start positions and will swim until finding the hidden platform (45 s max). It will return to its cage under a warming lamp for 2-3 min before the next trial. On the remaining trials, the rat will enter the maze from one of the remaining start points. This procedure will be repeated over 5 days.

Probe Trial (P39):

After conclusion of Day 5 trials, the platform will be removed and rats will enter the tub at a random location. Time spent swimming in the quadrant that previously contained the submerged platform, as well as crossings made in the area that previously contained the platform will be measured.

Data Acquisition and Analysis:

Ethovision XT video tracking system (Naldus) will be used to record behavior of rats in the maze. Detailed recording of distance traveled and time to reach the platform for individual animals will be evaluated by repeated measure ANOVAs. Variables include Sex (male/female), Treatment (HI/Sham), Drug (IAIP/vehicle), Time to reach the platform, Distance traveled, and Day. For probe trials, time spent in the correct quadrant and the number of crossings in the area the platform was previously located will also be measured. One-way ANOVAs will be used for simple effects analyses for each day of testing and for comparison of probe trial data between groups.

Possible Outcomes and Alternative Procedures:

Our studies are the first to measure IAIP and cytokine concentrations, and the effect of IAIP treatment, in both sexes after Ill. Though the probability of IAIP levels remaining stable at the measured time points is unlikely, we recognize we may not find differences in levels between the sexes. Nonetheless, we still predict identifying neuroprotective effects of IAIP treatment based upon recent studies[26, 45] and our data in male rats only. Importantly, the development of neuroprotectants nonspecific to sex is possible if similar expression and/or depletion of IAIP is shown in males and females. Additionally, we recognize endogenous levels of IAIP may differ between the sexes in a time dependent manner and therefore optimal intervention with IAIP may differ in timing for males and females. However, IAIP will be given immediately after HI based on our data, but also so that these important proteins are 'on board' as soon as would be possible in the clinical setting (i.e., if the timing of the HI event was known). The opportunity for studies exploring treatment at the time point of lowest endogenous levels, or the efficacy of treatment at later time points are important considerations for future studies. Secondly, we expect a positive outcome in both histological and behavioral measures after IAIP administration. If attenuation of injury is not observed (i.e., reduced FJB and EBI staining) in either sex, the dose, number of doses, or timing of doses may be modified. Moreover, exogenous IAIP treatment may be more efficacious to one sex, requiring differential dosing/treatment strategies to achieve equivalent efficacy. Finally, hypothermia is currently the only approved therapy for the treatment of HI in human neonates. The use of IAIP as a neuroprotective agent may be enhanced if combined with hypothermia treatment.

Ethical Considerations:

Our use of a live animal model is essential to investigate the acute cellular and molecular mechanisms of HI with no alternatives in the proposed research. Careful evaluation or all protocols has ensured animals will be closely monitored for the duration of study. We perform aseptic surgery with utmost consideration for comfort and post-surgical trauma is minimal. Technical difficulties are unlikely as all techniques have been previously employed by the investigator and are used routinely in our laboratory and no animals are requested for technique development. A rat model is ideal due to prior successful studies performed by CAH and tissue availability for protein/assay analysis. Also, this is the most practical study design for this proposal due to shorter gestation and increased offspring per litter than sheep.

Impact of Study:

Considering the tremendous amount of research surrounding sex differences in adult stroke—and the tremendous advancements that have come from this research—it is difficult to understand the paucity of research surrounding similar issues in the neonate. Males and females differ in behavioral, physiological, and genetic levels (even in neonates), so it is not surprising that sex differences manifest in epidemiology and pathogenesis of HI. Our research shows considerable significance in the following areas: 1) understanding how and why males and females respond differently to HI injury during the neonatal period; 2) examining mechanisms underlying these differences, specifically with regard to the role of cytokines and IAIP; and 3) understanding how exogenous IAIP treatment may modulate both anatomical and behavioral indices of injury. The results of our studies move the field of sex differences in HI injury forward and contribute to the clinical implementation of sex-specific neuroprotectants for infants suffering from HI injury.

Other Embodiments

While the invention has been described in connection with specific embodiments thereof, it will be understood that it is capable of further modifications and this application is intended to cover any variations, uses, or adaptations of the invention following, in general, the principles of the invention and including such departures from the present disclosure that come within known or customary practice within the art to which the invention pertains and may be applied to the essential features hereinbefore set forth.

All patents patent applications and publications mentioned herein are incorporated by reference to the same extent as if each independent patent or patent application was specifically and individually indicated to be incorporated by reference in its entirety.

REFERENCES

A1. Fries, E., and Blom, A. M. (2000) Bikunin—not just a plasma proteinase inhibitor. *Int J Biochem Cell Biol* 32, 125-137

A2. Lim, Y. P., Bendelja, K., Opal, S. M., Siryaporn, E., Hixson, D. C., and Palardy, J. E. (2003) Correlation between mortality and the levels of inter-alpha inhibitors in the plasma of patients with severe sepsis. *J Infect Dis* 188, 919-926

A3. Salier, J. P., Rouet, P., Raguenez, G., and Daveau, M. (1996) The inter-alpha-inhibitor family: from structure to regulation. *Biochem J* 315 (Pt 1), 1-9

A4. Potempa, J., Kwon, K., Chawla, R., and Travis, J. (1989) Inter-alpha-trypsin inhibitor. Inhibition spectrum of native and derived forms. *J Biol Chem* 264, 15109-15114

A5. Daveau, M., Jean, L., Soury, E., Olivier, E., Masson, S., Lyoumi, S., Chan, P., Hiron, M., Lebreton, J. P., Husson, A., Jegou, S., Vaudry, H., and Salier, J. P. (1998) Hepatic and extra-hepatic transcription of inter-alpha-inhibitor family genes under normal or acute inflammatory conditions in rat. *Arch Biochem Biophys* 350, 315-323

A6. Baek, Y. W., Brokat, S., Padbury, J. F., Pinar, H., Hixson, D. C., and Lim, Y. P. (2003) Inter-alpha inhibitor proteins in infants and decreased levels in neonatal sepsis. *J Pediatr* 143, 11-15

A7. Chaaban, H., Shin, M., Sirya, E., Lim, Y. P., Caplan, M., and Padbury, J. F. (2010) Inter-alpha inhibitor protein level in neonates predicts necrotizing enterocolitis. *J Pediatr* 157, 757-761

A8. Chaaban, H., Singh, K., Huang, J., Siryaporn, E., Lim, Y. P., and Padbury, J. F. (2009) The role of inter-alpha inhibitor proteins in the diagnosis of neonatal sepsis. *J Pediatr* 154, 620-622 e621

A9. O'Shea, T. M. (2002) Cerebral palsy in very preterm infants: new epidemiological insights. *Ment Retard Dev Disabil Res Rev* 8, 135-145

A10. Stoll, B. J., Hansen, N. I., Adams-Chapman, I., Fanaroff, A. A., Hintz, S. R., Vohr, B., and Higgins, R. D. (2004) Neurodevelopmental and growth impairment among extremely low-birth-weight infants with neonatal infection. *Jama.* 292, 2357-2365.

A11. Hirose, J., Ozawa, T., Miura, T., Isaji, M., Nagao, Y., Yamashiro, K., Nii, A., Kato, K., and Uemura, A. (1998) Human neutrophil elastase degrades inter-alpha-trypsin inhibitor to liberate urinary trypsin inhibitor related proteins. *Biol Pharm Bull* 21, 651-656

A12. Opal, S. M., Lim, Y. P., Siryaporn, E., Moldawer, L. L., Pribble, J. P., Palardy, J. E., and Souza, S. (2007) Longitudinal studies of inter-alpha inhibitor proteins in severely septic patients: a potential clinical marker and mediator of severe sepsis. *Crit Care Med* 35, 387-392

A13. Singh, K., Zhang, L. X., Bendelja, K., Heath, R., Murphy, S., Sharma, S., Padbury, J. F., and Lim, Y. P. (2010) Inter-alpha inhibitor protein administration improves survival from neonatal sepsis in mice. *Pediatr Res* 68, 242-247

A14. Yang, T. C., Zhang, S. W., Sun, L. N., Wang, H., and Ren, A. M. (2008) Magnolol attenuates sepsis-induced gastrointestinal dysmotility in rats by modulating inflammatory mediators. *World J Gastroenterol* 14, 7353-7360

A15. El Maradny, E., Kanayama, N., Halim, A., Maehara, K., Kobayashi, T., and Terao, T. (1996) Effects of urinary trypsin inhibitor on myometrial contraction in term and preterm deliveries. *Gynecol Obster Invest* 41, 96-102

A16. Futamura, Y., Kajikawa, S., Kaga, N., and Shibutani, Y. (1999) Protection against preterm delivery in mice by urinary trypsin inhibitor. *Obstet Gynecol* 93, 100-108

A17. Kaga, N., Katsuki, Y., Futamura, Y., Obata, M., and Shibutani, Y. (1996) Role of urinary trypsin inhibitor in the maintenance of pregnancy in mice. *Obstet Gynecol* 88, 872-882

A18. Kakinuma, C., Kuwayama, C., Kaga, N., Futamura, Y., Katsuki, Y., and Shibutani, Y. (1997) Trophoblastic apoptosis in mice with preterm delivery and its suppression by urinary trypsin inhibitor. *Obstet Gynecol* 90, 117-124

A19. Kanayama, N., el Maradny, E., Yamamoto, N., Tokunaga, N., Maehara, K., and Terao, T. (1996) Urinary trypsin inhibitor: a new drug to treat preterm labor: a comparative study with ritodrine. *Eur J Obstet Gynecol Reprod Biol* 67, 133-138

A20. Garantziotis, S., Zudaire, E., Trempus, C. S., Hollingsworth, J. W., Jiang, D., Lancaster, L. H., Richardson, E., Zhuo, L., Cuttitta, F., Brown, K. K., Noble, P. W., Kimata, K., and Schwartz, D. A. (2008) Serum inter-alpha-trypsin inhibitor and matrix hyaluronan promote angiogenesis in fibrotic lung injury. *Am J Respir Crit Care Med* 178, 939-947

A21. Sanchez, D., Martinez, S., Lindqvist, A., Akerstrom, B., and Falkenberg, C. (2002) Expression of the AMBP gene transcript and its two protein products, alpha(1)-microglobulin and bikunin, in mouse embryogenesis. *Mech Dev* 117, 293-298

A22. Businaro, R., Leali, F. M., De Renzis, G., Pompili, E., Pagliari, G., Menghi, G., and Fumagalli, L. (1992) Inter-alpha-trypsin inhibitor-related immunoreactivity in human tissues and body fluids. *Cell Mol Biol* 38, 463-471

A23. Cai, T., Yu, P., Monga, S. P., Mishra, B., and Mishra, L. (1998) Identification of mouse itih-4 encoding a glycoprotein with two EF-hand motifs from early embryonic liver. *Biochim Biophys Acta* 1398, 32-37

A24. Kashyap, R. S., Nayak, A. R., Deshpande, P. S., Kabra, D., Purohit, H. J., Taori, G. M., and Daginawala, H. F. (2009) Inter-alpha-trypsin inhibitor heavy chain 4 is a novel marker of acute ischemic stroke. *Clin Chim Acta* 402, 160-163

A25. Kato, M., Seki, N., Sugano, S., Hashimoto, K., Masuho, Y., Muramatsu, M., Kaibuchi, K., and Nakafuku, M. (2001) Identification of sonic hedgehog-responsive genes using cDNA microarray. *Biochem Biophys Res Commun* 289, 472-478

A26. Mizushima, S., Nii, A., Kato, K., and Uemura, A. (1998) Gene expression of the two heavy chains and one light chain forming the inter-alpha-trypsin-inhibitor in human tissues. *Biol Pharm Bull* 21, 167-169

A27. Takano, M., Mori, Y., Shiraki, H., Horie, M., Okamoto, H., Narahara, M., Miyake, M., and Shikimi, T. (1999) Detection of bikunin mRNA in limited portions of rat brain. *Life Sci* 65, 757-762

A28. Werbowetski-Ogilvie, T. E., Agar, N. Y., Waldkircher de Oliveira, R. M., Faury, D., Antel, J. P., Jabado, N., and Del Maestro, R. F. (2006) Isolation of a natural inhibitor of human malignant glial cell invasion: inter alpha-trypsin inhibitor heavy chain 2. *Cancer Res* 66, 1464-1472

A29. Yoshida, E., Yoshimura, M., Ito, Y., and Mihara, H. (1991) Demonstration of an active component of inter-alpha-trypsin inhibitor in the brains of Alzheimer type dementia. *Biochem Biophys Res Commun* 174, 1015-1021

A30. Chan, P., Risler, J. L., Raguenez, G., and Salier, J. P. (1995) The three heavy-chain precursors for the inter-alpha-inhibitor family in mouse: new members of the multicopper oxidase protein group with differential transcription in liver and brain. *Biochem J* 306 (Pt 2), 505-512

A31. Yano, T., Anraku, S., Nakayama, R., and Ushijima, K. (2003) Neuroprotective effect of urinary trypsin inhibitor against focal cerebral ischemia-reperfusion injury in rats. *Anesthesiology* 98, 465-473

A32. Shu, Y., Yang, Y., Qiu, W., Lu, Z., Li, Y., Bao, J., Feng, M., and Hu, X. (2011) Neuroprotection by ulinastatin in experimental autoimmune encephalomyelitis. *Neurochem Res* 36, 1969-1977

A33. Horiguchi, T., and Harada, Y. (1993) The effect of protease inhibitor on reperfusion injury after unilateral pulmonary ischemia. *Transplantation* 55, 254-258

A34. Li, X. K., Matin, A. F., Suzuki, H., Uno, T., Yamaguchi, T., and Harada, Y. (1993) Effect of protease inhibitor on ischemia/reperfusion injury of the rat liver. *Transplantation* 56, 1331-1336

A35. Li, X. K., Suzuki, H., Kimura, T., Kawabe, A., Uno, T., and Harada, Y. (1994) Ulinastatin, a protease inhibitor, attenuates intestinal ischemia/reperfusion injury. *Transplant Proc* 26, 2423-2425

A36. Cao, Z. L., Okazaki, Y., Naito, K., Ueno, T., Natsuaki, M., and Itoh, T. (2000) Ulinastatin attenuates reperfusion injury in the isolated blood-perfused rabbit heart. *Ann Thorac Surg* 69, 1121-1126

A37. Nakahama, H., Obata, K., and Sugita, M. (1996) Ulinastatin ameliorates acute ischemic renal injury in rats. *Ren Fail* 18, 893-898

A38. Salier, J. P., Chan, P., Raguenez, G., Zwingman, T., and Erickson, R. P. (1993) Developmentally regulated transcription of the four liver-specific genes for inter-alpha-inhibitor family in mouse. *Biochem J* 296 (Pt 1), 85-91

A39. Johanson, C. E., Duncan, J. A., 3rd, Klinge, P. M., Brinker, T., Stopa, E. G., and Silverberg, G. D. (2008) Multiplicity of cerebrospinal fluid functions: New challenges in health and disease. *Cerebrospinal Fluid Res* 5, 10

A40. Johanson, C. E., Stopa, E. G., and McMillan, P. N. (2011) The blood-cerebrospinal fluid barrier: structure and functional significance. *Methods Mol Biol* 686, 101-131

A41. Johansson, P. A., Dziegiclewska, K. M., Liddelow, S. A., and Saunders, N. R. (2008) The blood-CSF barrier explained: when development is not immaturity. *Bioessays* 30, 237-248

A42. Johansson, P. A., Dziegielewska, K. M., Ek, C. J., Habgood, M. D., Liddelow, S. A., Potter, A. M., Stolp, H. B., and Saunders, N. R. (2006) Blood-CSF barrier function in the rat embryo. *Eur J Neurosci* 24, 65-76

A43. Bagnard, D., Vaillant, C., Khuth, S. T., Dufay, N., Lohrum, M., Puschel, A. W., Belin, M. F., Bolz, J., and Thomasset, N. (2001) Semaphorin 3A-vascular endothelial growth factor-165 balance mediates migration and apoptosis of neural progenitor cells by the recruitment of shared receptor. *J Neurosci* 21, 3332-3341

A44. Bondy, C., Werner, H., Roberts, C. T., Jr., and LeRoith, D. (1992) Cellular pattern of type-I insulin-like growth factor receptor gene expression during maturation of the rat brain: comparison with insulin-like growth factors I and II. *Neuroscience* 46, 909-923

A45. Chesnutt, C., Burrus, L. W., Brown, A. M., and Niswander, L. (2004) Coordinate regulation of neural tube patterning and proliferation by TGFbeta and WNT activity. *Dev Biol* 274, 334-347

A46. Diaz-Ruiz, C., Perez-Tomas, R., Domingo, J., and Ferrer, I. (1993) Immunohistochemical localization of transforming growth factor-alpha in choroid plexus of the rat and chicken. *Neurosci Lett* 164, 44-46

A47. Gonzalez, A. M., Berry, M., Maher, P. A., Logan, A., and Baird, A. (1995) A comprehensive analysis of the distribution of FGF-2 and FGFR1 in the rat brain. *Brain Res* 701, 201-226

A48. Johanson, C. E., Szmydynger-Chodobska, J., Chodobski, A., Baird, A., McMillan, P., and Stopa, E. G. (1999) Altered formation and bulk absorption of cerebrospinal fluid in FGF-2-induced hydrocephalus. *Am J Physiol* 277, R263-271

A49. Justicia, C., Perez-Asensio, F. J., Burguete, M. C., Salom, J. B., and Planas, A. M. (2001) Administration of transforming growth factor-alpha reduces infarct volume after transient focal cerebral ischemia in the rat. *J Cereb Blood Flow Metab* 21, 1097-1104

A50. Raballo, R., Rhee, J., Lyn-Cook, R., Leckman, J. F., Schwartz, M. L., and Vaccarino, F. M. (2000) Basic fibroblast growth factor (Fgf2) is necessary for cell proliferation and neurogenesis in the developing cerebral cortex. *J Neurosci* 20, 5012-5023

A51. Reid, S., and Ferretti, P. (2003) Differential expression of fibroblast growth factor receptors in the developing murine choroid plexus. *Brain Res Dev Brain Res* 141, 15-24

A52. Sun, Y., Jin, K., Xie, L., Childs, J., Mao, X. O., Logvinova, A., and Greenberg, D. A. (2003) VEGF-induced neuroprotection, neurogenesis, and angiogenesis after focal cerebral ischemia. *J Clin Invest* 111, 1843-1851

A53. Hu, H. (1999) Chemorepulsion of neuronal migration by Slit2 in the developing mammalian forebrain. *Neuron* 23, 703-711

A54. Nguyen-Ba-Charvet, K. T., Picard-Riera, N., Tessier-Lavigne, M., Baron-Van Evercooren, A., Sotelo, C., and Chedotal, A. (2004) Multiple roles for slits in the control of cell migration in the rostral migratory stream. *J Neurosci* 24, 1497-1506

A55. Dziegielewska, K. M., Evans, C. A., Lorscheider, F. L., Malinowska, D. H., Mollgard, K., Reynolds, M. L., and Saunders, N. R. (1981) Plasma proteins in fetal sheep brain: blood-brain barrier and intracerebral distribution. *J Physiol* 318, 239-250

A56. Dziegielewska, K. M., Evans, C. A., Malinowska, D. H., Mollgard, K., Reynolds, M. L., and Saunders, N. R. (1980) Blood-cerebrospinal fluid transfer of plasma proteins during fetal development in the sheep. *J Physiol* 300, 457-465

A57. Dziegielewska, K. M., Knott, G. W., and Saunders, N. R. (2000) The nature and composition of the internal environment of the developing brain. *Cell Mol Neurobiol* 20, 41-56

A58. Gato, A., Martin, C., Alonso, M. I., Martinez-Alvarez, C., and Moro, J. A. (2001) Chondroitin sulphate proteoglycan is involved in lens vesicle morphogenesis in chick embryos. *Exp Eye Res* 73, 469-478

A59. Back, S. A. (2006) Perinatal white matter injury: the changing spectrum of pathology and emerging insights into pathogenetic mechanisms. *Ment Retard Dev Disabil Res Rev* 12, 129-140

A60. Gunn, A. J., and Gunn, T. R. (1997) Changes in risk factors for hypoxic-ischaemic seizures in term infants. *Aust N Z J Obstet Gynaecol* 37, 36-39

A61. Stonestreet, B. S., Sadowska, G. B., McKnight, A. J., Patlak, C., and Petersson, K. H. (2000) Exogenous and endogenous corticosteroids modulate blood-brain barrier development in the ovine fetus. *Am J Physiol Regul Integr Comp Physiol* 279, R468-477

A62. Barlow, R. M. (1969) The foetal sheep: morphogenesis of the nervous system and histochemical aspects of myelination. *J Comp Neurol* 135, 249-262

A63. Bernhard, C. G., Kolmodin, G. M., and Meyerson, B. A. (1967) On the prenatal development of function and structure in the somesthetic cortex of the sheep. *Prog Brain Res* 26, 60-77

A64. Back, S. A., Riddle, A., and Hohimer, A. R. (2006) Role of instrumented fetal sheep preparations in defining the pathogenesis of human periventricular white-matter injury. *J Child Neurol* 21, 582-589

A65. Stonestreet, B. S., Oen-Hsiao, J. M., Petersson, K. H., Sadowska, G. B., and Patlak, C. S. (2003) Regulation of brain water during acute hyperosmolality in ovine fetuses, lambs, and adults. *J Appl Physiol* 94, 1491-1500

A66. Stonestreet, B. S., Petersson, K. H., Sadowska, G. B., Pettigrew, K. D., and Patlak, C. S. (1999) Antenatal steroids decrease blood-brain barrier permeability in the ovine fetus. *Am J Physiol* 276, R283-289

A67. Sysyn, G. D., Petersson, K. H., Patlak, C. S., Sadowska, G. B., and Stonestreet, B. S. (2001) Effects of postnatal dexamethasone on blood-brain barrier permeability and brain water content in newborn lambs. *Am J Physiol Regul Integr Comp Physiol* 280, R547-553

A68. Kim, C. R., Sadowska, G. B., Newton, S. A., Merino, M., Petersson, K. H., Padbury, J. F., and Stonestreet, B. S. (2011) Na+,K+-ATPase activity and subunit protein expression: ontogeny and effects of exogenous and endogenous steroids on the cerebral cortex and renal cortex of sheep. *Reprod Sci* 18, 359-373

A69. Kim, C. R., Sadowska, G. B., Petersson, K. H., Merino, M., Sysyn, G. D., Padbury, J. F., and Stonestreet, B. S. (2006) Effects of postnatal steroids on Na+/K+-ATPase activity and alpha1- and beta1-subunit protein expression in the cerebral cortex and renal cortex of newborn lambs. *Reprod Fertil Dev* 18, 413-423

A70. Malaeb, S. N., Sadowska, G. B., and Stonestreet, B. S. (2007) Effects of maternal treatment with corticosteroids on tight junction protein expression in the cerebral cortex of the ovine fetus with and without exposure to in utero brain ischemia. *Brain Res* 1160, 11-19

A71. Sadowska, G. B., Malaeb, S. N., and Stonestreet, B. S. (2010) Maternal glucocorticoid exposure alters tight junction protein expression in the brain of fetal sheep. *Am J Physiol Heart Circ Physiol* 298, H179-188

A72. Sadowska, G. B., Stopa, E. G., and Stonestreet, B. S. (2009) Ontogeny of connexin 32 and 43 expression in the cerebral cortices of ovine fetuses, newborns, and adults. *Brain Res* 1255, 51-56

A73. Ron, N. P., Kazianis, J. A., Padbury, J. F., Brown, C. M., McGonnigal, B. G., Sysyn, G. D., Sadowska, G. B., and Stonestreet, B. S. (2005) Ontogeny and the effects of corticosteroid pretreatment on aquaporin water channels in the ovine cerebral cortex. *Reprod Fertil Dev* 17, 535-542

A74. Odum, L., and Nielsen, H. W. (1994) Human protein HC (alpha 1-microglobulin) and inter-alpha-trypsin inhibitor in connective tissue. *Histochem J* 26, 799-803

A75. Yoshida, E., Sumi, H., Maruyama, M., Tsushima, H., Matsuoka, Y., Sugiki, M., and Mihara, H. (1989) Distribution of acid stable trypsin inhibitor immunoreactivity in normal and malignant human tissues. *Cancer* 64, 860-869

A76. Odum, L., Halkier, T., Hojrup, P., and Schousboe, I. (1989) Characterization of urinary proteinase inhibitors with segments of amino acids sequences identical to sequences of pancreatic secretory trypsin inhibitor. *Int J Biochem* 21, 1319-1327

A77. Shikimi, T., Hattori, K., and Takaori, S. (1992) Existence of a human urinary trypsin inhibitor (urinastatin)-like substance in the rat brain. *Jpn J Pharmacol* 60, 97-103

A78. Lucas, S. M., Rothwell, N. J., and Gibson, R. M. (2006) The role of inflammation in CNS injury and disease. *Br J Pharmacol* 147 Suppl 1, S232-240

A79. Koga, Y., Fujita, M., Tsuruta, R., Koda, Y., Nakahara, T., Yagi, T., Aoki, T., Kobayashi, C., Izumi, T., Kasaoka, S., Yuasa, M., and Maekawa, T. (2010) Urinary trypsin inhibitor suppresses excessive superoxide anion radical generation in blood, oxidative stress, early inflammation, and endothelial injury in forebrain ischemia/reperfusion rats. *Neurol Res* 32, 925-932

A80. Abe, H., Sugino, N., Matsuda, T., Kanamaru, T., Oyanagi, S., and Mori, H. (1996) Effect of ulinastatin on delayed neuronal death in the gerbil hippocampus. *Masui* 45, 38-43

A81. Monard, D. (1988) Cell-derived proteases and protease inhibitors as regulators of neurite outgrowth. *Trends Neurosci* 11, 541-544

A82. Regeniter, A., Kuhle, J., Mehling, M., Moller, H., Wurster, U., Freidank, H., and Siede, W. H. (2009) A modern approach to CSF analysis: pathophysiology, clinical application, proof of concept and laboratory reporting. *Clin Neurol Neurosurg* 111, 313-318

A83. Saunders, N. R. (1977) The blood brain barrier in the foetal and newborn lamb. *Ann Rech Vet* 8, 384-395

A84. Stonestreet, B. S., Patlak, C. S., Pettigrew, K. D., Reilly, C. B., and Cserr, H. F. (1996) Ontogeny of blood-brain barrier function in ovine fetuses, lambs, and adults. *Am J Physiol* 271, R1594-1601

A85. Ek, C. J., Dziegielewska. K. M., Habgood, M. D., and Saunders, N. R. (2012) Barriers in the developing brain and Neurotoxicology. *Neurotoxicology* 33, 586-604

A86. Gato, A., Martin, P., Alonso, M. I., Martin, C., Pulgar, M. A., and Moro, J. A. (2004) Analysis of cerebro-spinal fluid protein composition in early developmental stages in chick embryos. *J Exp Zool A Comp Exp Biol* 301, 280-289

A87. Klosovskii, B. N., and Zhukova, T. P. (1963) Effect of colchicine on remote phases of growing capillaries in the brain. *Arkh Patol* 35(3), 38-44

A88. Noor, N. M., Steer, D. L., Wheaton, B. J., Ek, C. J., Truettner, J. S., Dietrich, W. D., Dziegielewska, K. M., Richardson, S. J., Smith, A. I., VandeBerg, J. L., and Saunders, N. R. (2011) Age-dependent changes in the proteome following complete spinal cord transection in a postnatal South American opossum (*Monodelphis domestica*). *PLoS One* 6, e27465

A89. Ramey, B. A., and Birge, W. J. (1979) Development of cerebrospinal fluid and the blood-cerebrospinal fluid barrier in rabbits. *Dev Biol* 68, 292-298

A90. Saunders, N. R. (1977) Ontogeny of the blood-brain barrier. *Exp Eye Res* 25 Suppl, 523-550

A91. Gato, A., and Desmond, M. E. (2009) Why the embryo still matters: CSF and the neuroepithelium as interdependent regulators of embryonic brain growth, morphogenesis and histiogenesis. *Dev Biol* 327, 263-272

A92. Checiu, I., Prelipceanu, O., and Popescu, O. (1984) The role of the cerebrospinal fluid during embryonic development. A biochemical study. *Morphol Embryol (Bucur)* 30, 243-250

A93. Fielitz, W., Esteves, A., and Moro, R. (1984) Protein composition of cerebrospinal fluid in the developing chick embryo. *Brain Res* 315, 111-115

A94. Dobbing, J., and Sands, J. (1979) Comparative aspects of the brain growth spurt. *Early Hum Dev* 3, 79-83

A95. Mcintosh, G. H., Baghurst, K. I., Potter, B. J., and Hetzel, B. S. (1979) Foetal brain development in the sheep. *Neuropathol Appl Neurobiol* 5, 103-114

A96. Iwama, H., Ohmori, S., and Tsutsumi, T. (2000) Detectable concentrations of urinary trypsin inhibitor in cerebrospinal fluid. *J Neurosurg Anesthesiol* 12, 29-32

A97. Dziegielewska, K. M., Habgood, M. D., Mollgard, K., Stagaard, M., and Saunders, N. R. (1991) Species-specific transfer of plasma albumin from blood into different cerebrospinal fluid compartments in the fetal sheep. *J Physiol* 439, 215-237

A98. Ek, C. J., Habgood, M. D., Dziegielewska, K. M., Potter, A., and Saunders, N. R. (2001) Permeability and route of entry for lipid-insoluble molecules across brain barriers in developing Monodelphis *domestica*. *J Physiol* 536, 841-853

A99. Ek, T., Pinkava, M., and Abrahamsson, J. (2005) Ara-C fever and infections after high-dose ara-C treatment in pediatric lymphoid malignancies. *J Pediatr Hematol Oncol* 27, 364-369

A100. Knott, G. W., Dziegielewska, K. M., Habgood, M. D., Li, Z. S., and Saunders, N. R. (1997) Albumin transfer across the choroid plexus of South American opossum (*Monodelphis domestica*). *J Physiol* 499 (Pt 1), 179-194

A101. Liddelow, S. A., Dziegielewska, K. M., Ek, C. J., Johansson, P. A., Potter, A. M., and Saunders, N. R. (2009) Cellular transfer of macromolecules across the developing choroid plexus of *Monodelphis domestica*. *Eur J Neurosci* 29, 253-266

A102. Liddelow, S. A., Dziegielewska, K. M., VandeBerg, J. L., Noor, N. M., Potter, A. M., and Saunders, N. R. (2011) Modification of protein transfer across blood/cerebrospinal fluid barrier in response to altered plasma protein composition during development. *Eur J Neurosci* 33, 391-400

A103. Mollgard, K., and Saunders, N. R. (1977) A possible transepithelial pathway via endoplasmic reticulum in foetal sheep choroid plexus. *Proc R Soc Lond B Biol Sci* 199, 321-326

ADDITIONAL REFERENCES

1. Gunn A J, Gunn T R, de Haan H H, Williams C E, Gluckman P D. Dramatic neuronal rescue with prolonged selective head cooling after ischemia in fetal lambs. *J. Clin. Invest.* 1997; 99:248-256
2. Chau V, Poskitt K J, McFadden D E, Bowen-Roberts T, Synnes A, Brant R, Sargent M A, Soulikias W, Miller S P. Effect of chorioamnionitis on brain development and injury in premature newborns. *Ann. Neurol.* 2009; 66:155-164
3. Mallard E C, Williams C E, Johnston B M, Gluckman P D. Increased vulnerability to neuronal damage after umbilical cord occlusion in fetal sheep with advancing gestation. *Am. J. Obstet. Gynecol.* 1994; 170:206-214
4. Petersson K H, Pinar H, Stopa E G, Sadowska G B, Hanumara R C, Stonestreet B S. Effects of exogenous glucose on brain ischemia in ovine fetuses. *Pediatr Res.* 2004; 56:621-629. Epub 24 Aug. 2019.
5. Petersson K H, Pinar H, Stopa E G, Faris R A, Sadowska G B, Hanumara R C, Stonestreet B S. White matter injury after cerebral ischemia in ovine fetuses. *Pediatr Res.* 2002; 51:768-776.
6. Back S A, Riddle A, Hohimer A R. Role of instrumented fetal sheep preparations in defining the pathogenesis of human periventricular white-matter injury., *J Child Neurol.* 2006; 21:582-589.
7. Riddle A, Luo N L, Manese M, Beardsley D J, Green L, Rorvik D A, Kelly K A, Barlow C H, Kelly J J, Hohimer A R, Back S A. Spatial heterogeneity in oligodendrocyte lineage maturation and not cerebral blood flow predicts fetal ovine periventricular white matter injury. *J Neurosci.* 2006; 26:3045-3055.

8. Futamura Y, Kajikawa S, Kaga N, Shibutani Y. Protection against preterm delivery in mice by urinary trypsin inhibitor. *Obstet Gynecol.* 1999; 93:100-108.
9. Kakinuma C, Kuwayama C, Kaga N, Futamura Y, Katsuki Y, Shibutani Y. Trophoblastic apoptosis in mice with preterm delivery and its suppression by urinary trypsin inhibitor. *Obstet Gynecol.* 1997; 90:117-124.
10. Kaga N, Katsuki Y, Futamura Y, Obata M, Shibutani Y. Role of urinary trypsin inhibitor in the maintenance of pregnancy in mice. *Obstet Gynecol.* 1996; 88:872-882.
11. Singh K, Zhang L X, Bendelja K, Heath R, Murphy S, Sharma S, Padbury J F, Lim Y P. Inter-alpha inhibitor protein administration improves survival from neonatal sepsis in mice. *Pediatr. Res.* 2010; 68:242-247
12. El Maradny E, Kanayama N, Halim A, Maehara K, Kobayashi T, Terao T. Effects of urinary trypsin inhibitor on myometrial contraction in term and preterm deliveries. *Gynecol. Obstet. Invest.* 1996; 41:96-102
13. Kanayama N, el Maradny E, Yamamoto N, Tokunaga N, Maehara K, Terao T. Urinary trypsin inhibitor: A new drug to treat preterm labor: A comparative study with ritodrine. *Eur J Obstet Gynecol Reprod Biol.* 1996; 67:133-138.
14. Matsuda Y, Yunohara N. Effects of urinary trypsin inhibitor in patients at risk for premature labor with a bulging fetal membrane. *Fetal Diagn Ther.* 2002; 17:69-74.
15. Kaga N, Katsuki Y, Kajikawa S, Shibutani Y. Preventive effect of ritodrine hydrochloride and/or urinary trypsin inhibitor against lipopolysaccharide-induced preterm delivery in mice. *Acta Obstet Gynecol Scand.* 1997; 76:811-816.
16. Kajikawa S, Kaga N, Futamura Y, Shibutani Y. Tocolytic effect of magnesium sulfate and/or urinary trypsin inhibitor against lipopolysaccharide-induced preterm delivery in mice. *Acta Obstet Gynecol Scand.* 1998; 77:598-602.
17. Nelson K B, Grether J K. Potentially asphyxiating conditions and spastic cerebral palsy in infants of normal birth weight. *Am. J. Obstet. Gynecol.* 1998; 179:507-513
18. Nelson K B, Ellenberg J H. The asymptomatic newborn and risk of cerebral palsy. *Am. J. Dis. Child.* 1987; 141:1333-1335
19. Badawi N, Watson L, Petterson B, Blair E, Slee J, Haan E, Stanley F. What constitutes cerebral palsy? *Dev. Med. Child Neurol.* 1998; 40:520-527
20. Vohr B R, Msall M E. Neuropsychological and functional outcomes of very low birth weight infants. *Semin. Perinatol.* 1997; 21:202-220
21. Nelson K B, Ellenberg J H. Neonatal signs as predictors of cerebral palsy. *Pediatrics.* 1979; 64:225-232
22. Nelson K B, Dambrosia J M, Grether J K, Phillips T M. Neonatal cytokines and coagulation factors in children with cerebral palsy. *Ann. Neurol.* 1998; 44:665-675
23. Stanley F J. The aetiology of cerebral palsy. *Early Hum. Dev.* 1994; 36:81-88
24. Pharoah P O, Cooke T, Cooke R W, Rosenbloom L. Birthweight specific trends in cerebral palsy. *Arch. Dis. Child.* 1990:65:602-606
25. Cooke R W. Cerebral palsy in very low birthweight infants. *Arch. Dis. Child.* 1990; 65:201-206
26. Leviton A, Paneth N. White matter damage in preterm newborns—an epidemiologic perspective. *Early Hum. Dev.* 1990; 24:1-22
27. Grether J K, Nelson K B, Dambrosia J M, Phillips T M. Interferons and cerebral palsy. *J. Pediatr.* 1999; 134:324-332
28. Yoon B H, Romero R, Yang S H, Jun J K, Kim I O, Choi J H, Syn H C. Interleukin-6 concentrations in umbilical cord plasma are elevated in neonates with white matter lesions associated with periventricular leukomalacia. *Am. J. Obstet. Gynecol.* 1996; 174:1433-1440
29. Yoon B H, Romero R, Kim C J, Koo J N, Choe G, Syn H C, Chi J G. High expression of tumor necrosis factor-alpha and interleukin-6 in periventricular leukomalacia. *Am. J. Obstet. Gynecol.* 1997; 177:406-411
30. Yoon B H, Jun J K, Romero R, Park K H, Gomez R, Choi J H, Kim I O. Amniotic fluid inflammatory cytokines (interleukin-6, interleukin-1beta, and tumor necrosis factor-alpha), neonatal brain white matter lesions, and cerebral palsy. *Am. J. Obstet. Gynecol.* 1997; 177:19-26
31. Levene M I, Wigglesworth J S, Dubowitz V. Hemorrhagic periventricular leukomalacia in the neonate: A real-time ultrasound study. Pediatrics. 1983; 71:794-797
32. Trounce J Q, Rutter N, Levene M I. Periventricular leucomalacia and intraventricular haemorrhage in the preterm neonate. *Arch. Dis. Child.* 1986; 61:1196-1202
33. Kaur C, Ling E A. Periventricular white matter damage in the hypoxic neonatal brain: Role of microglial cells. *Prog. Neurobiol.* 2009; 87:264-280
34. Leviton A, Kuban K, O'Shea T M, Paneth N, Fichorova R, Allred E N, Dammann O. The relationship between early concentrations of 25 blood proteins and cerebral white matter injury in preterm newborns: The elgan study. *J. Pediatr.* 2011; 158:897-903 c891-895
35. Kinney H C, Back S A. Human oligodendroglial development: Relationship to periventricular leukomalacia. *Semin. Pediatr. Neurol.* 1998; 5:180-189
36. Rothwell N J. Annual review prize lecture cytokines—killers in the brain? *J Physiol.* 1999; 514:3-17
37. Kuby J. Immunology. New York: W.H. Freeman and Company; 1997:313-374.
38. Kogure K, Yamasaki Y, Matsuo Y, Kato H, Onodera H. Inflammation of the brain after ischemia. *Acta Neurochir Suppl.* 1996; 66:40-43
39. Wang X, Yue T L, Young P R, Barone F C, Feuerstein G Z. Expression of interleukin-6, c-fos, and zif268 mrnas in rat ischemic cortex. *J. Cereb. Blood Flow Metab.* 1995; 15:166-171
40. Pantoni L, Sarti C, Inzitari D. Cytokines and cell adhesion molecules in cerebral ischemia: Experimental bases and therapeutic perspectives. *Arterioscler. Thromb. Vasc. Biol.* 1998; 18:503-513
41. Eigler A, Sinha B, Hartmann G, Endres S. Taming tnf: Strategies to restrain this proinflammatory cytokine. *Immunol. Today.* 1997; 18:487-492
42. Barone F C, Arvin B, White R F, Miller A, Webb C L, Willette R N, Lysko P G, Feuerstein G Z. Tumor necrosis factor-alpha. A mediator of focal ischemic brain injury. *Stroke.* 1997; 28:1233-1244
43. Shohami E, Gallily R, Mechoulam R, Bass R, Ben-Hur T. Cytokine production in the brain following closed head injury: Dexanabinol (hu-211) is a novel tnf-alpha inhibitor and an effective neuroprotectant. *J. Neuroimmunol.* 1997; 72:169-177
44. Hageman J R, Caplan M S. An introduction to the structure and function of inflammatory mediators for clinicians. *Clin. Perinatol.* 1995; 22:251-261
45. Volpe J. Hypoxic-ischemic encephalopathy. *Neurology of the newborn.* Philadelphia, Pa.: W.B. Saunders Company; 1995:260-313.
46. Leviton A. Preterm birth and cerebral palsy: Is tumor necrosis factor the missing link? *Dev. Med. Child Neurol.* 1993; 35:553-558
47. Shah D K, Doyle L W, Anderson P J, Bear M, Daley A J, Hunt R W, Inder T E. Adverse neurodevelopment in 47. preterm infants with postnatal sepsis or necrotizing enterocolitis is mediated by white matter abnormalities on magnetic resonance imaging at term. *J Pediatr.* 2008; 153:170-175, 175.e171. Epub 28 Apr. 2003.
48. Stoll B J, Hansen N I, Adams-Chapman I, Fanaroff A A, Hintz S R, Vohr B, Higgins R D. Neurodevelopmental and growth impairment among extremely low-birth-weight infants with neonatal infection. *Jama.* 2004; 292:2357-2365.
49. Yoon B H, Kim C J, Romero R, Jun J K, Park K H, Choi S T, Chi J G. Experimentally induced intrauterine infection causes fetal brain white matter lesions in rabbits. *Am. J. Obstet. Gynecol.* 1997; 177:797-802
50. Sadowska G B, Threlkeld S W, Flangini A, Sharma S, Stonestreet B S. Ontogeny and the effects of in utero brain ischemia on interleukin-1beta and interleukin-6 protein expression in ovine cerebral cortex and white matter. *Int. J. Dev. Neurosci.* 2012
51. Salier J P, Rouet P, Raguenez G, Daveau M. The inter-alpha-inhibitor family: From structure to regulation. *Biochem J.* 1996; 315:1-9.
52. Fries E, Blom A M. Bikunin—not just a plasma proteinase inhibitor. *Int J Biochem Cell Biol.* 2000; 32:125-137.
53. Potempa J, Kwon K, Chawla R, Travis J. Inter-alpha-trypsin inhibitor. Inhibition spectrum of native and derived forms. *J Biol Chem.* 1989; 264:15109-15114.
54. Daveau M, Jean L, Soury E, Olivier E, Masson S, Lyoumi S, Chan P, Hiron M, Lebreton J P, Husson A, Jegou S, Vaudry H, Salier J P. Hepatic and extra-hepatic transcription of inter-alpha-inhibitor family genes under normal or acute inflammatory conditions in rat. *Arch Biochem Biophy.* 1998; 350:315-323.
55. Baek Y W, Brokat S, Padbury J F, Pinar H, Hixson D C, Lim Y P. Inter-alpha inhibitor proteins in infants and decreased levels in neonatal sepsis. *J Pediatr.* 2003; 143:11-15.
56. Lim Y P, Bendelja K, Opal S M, Siryaporn E, Hixson D C, Palardy J E. Correlation between mortality and the levels of inter-alpha inhibitors in the plasma of patients with severe sepsis. *J Infect Dis.* 2003; 188:919-926. Epub 23 Aug. 2026.
57. Yang S, Lim Y P, Zhou M, Salvemini P, Schwinn H, Josic D, Koo D J, Chaudry I H, Wang P. Administration of human inter-alpha-inhibitors maintains hemodynamic stability and improves survival during sepsis. *Crit Care Med.* 2002; 30:617-622.
58. Wisniewski H G, Hua J C, Poppers D M, Naime D, Vilcek J, Cronstein B N. Tnf/il-1-inducible protein tsg-6 potentiates plasmin inhibition by inter-alpha-inhibitor and exerts a strong anti-inflammatory effect in vivo. *J Immunol.* 1996; 156:1609-1615.
59. Rosenberg G A. Matrix metalloproteinases and their multiple roles in neurodegenerative diseases. *Lancet Neurol.* 2009; 8:205-216.
60. Xue M, Hollenberg M D, Demchuk A, Yong V W. Relative importance of proteinase-activated receptor-1 versus matrix metalloproteinases in intracerebral hemorrhage-mediated neurotoxicity in mice. *Stroke.* 2009; 40:2199-2204. Epub 29 Apr. 2199.
61. Yano T, Anraku S, Nakayama R, Ushijima K. Neuroprotective effect of urinary trypsin inhibitor against focal cerebral ischemia-reperfusion injury in rats. *Anesthesiology.* 2003; 98:465-473.
62. Li X K, Matin A F, Suzuki H, Uno T, Yamaguchi T, Harada Y. Effect of protease inhibitor on ischemia/reperfusion injury of the rat liver. *Transplantation.* 1993; 56:1331-1336.
63. Li X K, Suzuki H, Kimura T, Kawabe A, Uno T, Harada Y. Ulinastatin, a protease inhibitor, attenuates intestinal ischemia/reperfusion injury. *Transplant Proc.* 1994; 26:2423-2425.
64. Horiguchi T, Harada Y. The effect of protease inhibitor on reperfusion injury after unilateral pulmonary ischemia. *Transplantation.* 1993; 55:254-258.
65. Shu Y, Yang Y, Qiu W, Lu Z, Li Y, Bao J, Feng M, Hu X. Neuroprotection by ulinastatin in experimental autoimmune encephalomyelitis. *Neurochem. Res.* 2011; 36:1969-1977
66. Chaaban H, Singh K, Huang J, Siryaporn E, Lim Y P, Padbury J F. The role of inter-alpha inhibitor proteins in the diagnosis of neonatal sepsis. *J Pediatr.* 2009; 154: 620-622.e621.
67. Chaaban H, Shin M, Sirya E, Lim Y P, Caplan M, Padbury J F. Inter-alpha inhibitor protein level in neonates predicts necrotizing enterocolitis. *J. Pediatr.* 2010; 157: 757-761
68. Hagberg H, Peebles D, Mallard C. Models of white matter injury: Comparison of infectious, hypoxic-ischemic, and excitotoxic insults. *Ment Retard Dev Disabil Res Rev.* 2002; 8:30-38
69. Gleason C A, Hamm C, Jones M D, Jr. Cerebral blood flow, oxygenation, and carbohydrate metabolism in immature fetal sheep in utero. *Am. J. Physiol.* 1989; 256:R1264-1268
70. Gleason C A, Hamm C, Jones M D, Jr. Effect of acute hypoxemia on brain blood flow and oxygen metabolism in immature fetal sheep. *Am. J. Physiol.* 1990; 258:H1064-1069
71. Gleason C A, Robinson R, Harris A P, Mayock D E, Traystman R J. Cerebrovascular effects of intravenous dopamine infusions in fetal sheep. *J. Appl. Physiol.* 2002; 92:717-724.
72. Gunn T R, Gunn A J, deHaan H H, Williams C E, Gluckman P D. Prolonged selective cerebral cooling prevents cytotoxic edema and improves recovery after cerebral ischemia in fetal sheep. *Pediatr. Res.* 1996; 39(4)
73. Hagberg H, Ichord R, Palmer C, Yager J Y, Vannucci S J. Animal models of developmental brain injury: Relevance to human disease. A summary of the panel discussion from the third hershey conference on developmental cerebral blood flow and metabolism. *Dev. Neurosci.* 2002; 24:364-366
74. Stonestreet B S, Patlak C S, Pettigrew K D, Reilly C B, Cserr H F. Ontogeny of blood-brain barrier function in ovine fetuses, lambs, and adults. *Am. J. Physiol.* 1996; 271:R1594-1601
75. Stonestreet B S, Petersson K H, Pettigrew K D, Patlak C S, Cserr H F. Brain water regulation in osmotically stressed fetuses. *Pediatr. Res.* 1995; 37:239A
76. Stonestreet B S, Sadowska G B, Leeman J, Hanumara R C, Petersson K H, Patlak C S. Effects of acute hyperosmolality on blood-brain barrier function in ovine fetuses and lambs. *Am J Physiol Regul Integr Comp Physiol.* 2006; 291:R1031-1039. Epub 2006 May 1011.
77. Stonestreet B S, Petersson K H, Sadowska G B, Patlak C S. Regulation of brain water during acute glucose-induced hyperosmolality in ovine fetuses, lambs, and adults. *J Appl Physiol.* 2004; 96:553-560. Epub 23 Oct. 2024.
78. Stonestreet B S, Sadowska G B, McKnight A J, Patlak C, Petersson K H. Exogenous and endogenous corticosteroids modulate blood-brain barrier development in the ovine fetus. *Am J Physiol Regul Integr Comp Physiol.* 2000; 279:R468-477

79. Stonestreet B S, McKnight A J, Sadowska G, Petersson K H, Oen J M, Patlak C S. Effects of duration of positive-pressure ventilation on blood-brain barrier function in premature lambs. *J. Appl. Physiol.* 2000; 88:1672-1677

80. Stonestreet B S, Elitt C M, Markowitz J, Petersson K H, Sadowska G B. Effects of antenatal corticosteroids on regional brain and non-neural tissue water content in the ovine fetus. *J. Soc. Gynecol. Investig.* 2003; 10:59-66.

81. Barlow R M. The foetal sheep: Morphogenesis of the nervous system and histochemical aspects of myelination. *J Comp Neurol.* 1969; 135:249-262.

82. Bernhard C G, Kolmodin G M, Meyerson B A. On the prenatal development of function and structure in the somesthetic cortex of the sheep. *Prog. Brain Res.* 1967; 26:60-77

83. Cook C J, Gluckman P D, Johnston B M, Williams C. The development of the somatosensory evoked potential in the unanaesthetized fetal sheep. *J Dev Physiol.* 1987; 9:441-455.

84. Cook C J, Williams C, Gluckman P D. Brainstem auditory evoked potentials in the fetal sheep, in utero. *J Dev Physiol.* 1987; 9:429-439.

85. Muller T, Lohle M, Schubert H, Bauer R, Wicher C, Antonow-Schlorke I, Sliwka U, Nathanielsz P W, Schwab M. Developmental changes in cerebral autoregulatory capacity in the fetal sheep parietal cortex. *J Physiol.* 2002; 539:957-967.

86. Helou S, Koehler R C, Gleason C A, Jones M D, Jr., Traystman R J. Cerebrovascular autoregulation during fetal development in sheep. *Am. J. Physiol.* 1994; 266: H1069-1074.

87. Shankaran S, Laptook A R, Ehrenkranz R A, Tyson J E, McDonald S A, Donovan E F, Fanaroff A A, Poole W K, Wright L L, Higgins R D, Finer N N, Carlo W A, Duara S, Oh W, Cotten C M, Stevenson D K, Stoll B J, Lemons J A, Guillet R, Jobe A H. Whole-body hypothermia for neonates with hypoxic-ischemic encephalopathy. *N Engl J Med.* 2005; 353:1574-1584.

88. Elitt C M, Sadowska G B, Stopa E G, Pinar H, Petersson K H, Stonestreet B S. Effects of antenatal steroids on ischemic brain injury in near-term ovine fetuses. *Early Hum Dev.* 2003; 73:1-15.

89. Rice J E, 3rd, Vannucci R C, Brierley J B. The influence of immaturity on hypoxic-ischemic brain damage in the rat. *Ann Neurol.* 1981; 9:131-141.

90. Schmued L C, Hopkins K J. Fluoro-jade: Novel fluorochromes for detecting toxicant-induced neuronal degeneration. *Toxicol. Pathol.* 2000; 28:91-99

91. Kochanek P M, Hallenbeck J M. Polymorphonuclear leukocytes and monocytes/macrophages in the pathogenesis of cerebral ischemia and stroke. *Stroke.* 1992; 23:1367-1379

92. Benveniste E N. Inflammatory cytokines within the central nervous system: Sources, function, and mechanism of action. *Am. J. Physiol.* 1992; 263:C1-16

93. Tarkowski E, Rosengren L, Blomstrand C, Wikkelso C, Jensen C, Ekholm S, Tarkowski A. Intrathecal release of pro- and anti-inflammatory cytokines during stroke. *Clin. Exp. Immunol.* 1997; 110:492-499

94. Clark W M, Rinker L G, Lessov N S, Hazel K, Eckenstein F. Time course of il-6 expression in experimental cns ischemia. *Neurol. Res.* 1999; 21:287-292

95. Hagberg H, Gilland E, Bona E, Hanson L A, Hahin-Zoric M, Blennow M, Hoist M, McRae A, Soder O. Enhanced expression of interleukin (il)-1 and il-6 messenger ma and bioactive protein after hypoxia-ischemia in neonatal rats. *Pediatr. Res.* 1996; 40:603-609

96. Szaflarski J, Burtrum D, Silverstein F S. Cerebral hypoxia-ischemia stimulates cytokine gene expression in perinatal rats. *Stroke.* 1995; 26:1093-1100

97. Cai Z, Lin S, Pang Y, Rhodes P G. Brain injury induced by intracerebral injection of interleukin-1beta and tumor necrosis factor-alpha in the neonatal rat. *Pediatr. Res.* 2004; 56:377-384

98. Hu X, Nesic-Taylor O, Qiu J, Rea H C, Fabian R, Rassin D K, Perez-Polo J R. Activation of nuclear factor-kappab signaling pathway by interleukin-1 after hypoxia/ischemia in neonatal rat hippocampus and cortex. *J Neurochem.* 2005; 93:26-37.

99. Prout A P, Frasch M G, Veldhuizen R, Hammond R, Matushewski B, Richardson B S. The impact of intermittent umbilical cord occlusions on the inflammatory response in preterm fetal sheep. *PloS one.* 2012; 7:e39043

100. Malaeb S N, Hovanesian V, Sarasin M D, Hartmann S M, Sadowska G B, Stonestreet B S. Effects of maternal antenatal glucocorticoid treatment on apoptosis in the ovine fetal cerebral cortex. *J Neurosci Res.* 2009; 87:179-189.

101. Banks W A. Are the extracellular [correction of extracelluar] pathways a conduit for the delivery of therapeutics to the brain? *Curr. Pharm. Des.* 2004; 10:1365-1370

102. Banks W A, Pagliari P, Nakaoke R, Morley J E. Effects of a behaviorally active antibody on the brain uptake and clearance of amyloid beta proteins. *Peptides.* 2005; 26:287-294

103. Banks W A, Terrell B, Farr S A, Robinson S M, Nonaka N, Morley J E. Passage of amyloid beta protein antibody across the blood-brain barrier in a mouse model of alzheimer's disease. *Peptides.* 2002; 23:2223-2226

104. Janus C, Pearson J, McLaurin J, Mathews P M, Jiang Y, Schmidt S D, Chishti M A, Home P, Heslin D, French J, Mount H T, Nixon R A, Mercken M, Bergeron C, Fraser P E, St George-Hyslop P, Westaway D. A beta peptide immunization reduces behavioural impairment and plaques in a model of alzheimer's disease. *Nature.* 2000; 408:979-982

105. Kozlowski G P, Sterzl I, Nilaver G. Localization patterns for immunoglobulins and albumins in the brain suggest diverse mechanisms for their transport across the blood-brain barrier (bbb). *Prog. Brain Res.* 1992; 91:149-154

106. Morgan D, Diamond D M, Gottschall P E, Ugen K E, Dickey C, Hardy J, Duff K, Jantzen P, DiCarlo G, Wilcock D, Connor K, Hatcher J, Hope C, Gordon M, Arendash G W. A beta peptide vaccination prevents memory loss in an animal model of alzheimer's disease. *Nature.* 2000; 408: 982-985

107. Stanimirovic D, Satoh K. Inflammatory mediators of cerebral endothelium: A role in ischemic brain inflammation. *Brain Pathol.* 2000; 10: 113-126.

108. Dammann O, Leviton A. Maternal intrauterine infection, cytokines, and brain damage in the preterm newborn. *Pediatr. Res.* 1997; 42:1-8

109. Manabat C, Han B H, Wendland M, Derugin N, Fox C K, Choi J, Holtzman D M, Ferriero D M, Vexler Z S. Reperfusion differentially induces caspase-3 activation in ischemic core and penumbra after stroke in immature brain. *Stroke.* 2003; 34:207-213

110. Wesche-Soldato D E, Chung C S, Lomas-Neira J, Doughty L A, Gregory S H, Ayala A. In vivo delivery of caspase-8 or fas sirna improves the survival of septic mice. *Blood.* 2005; 106:2295-2301

111. Khurana P, Ashraf Q M, Mishra O P, Delivoria-Papadopoulos M. Effect of hypoxia on caspase-3, -8, and -9 activity and expression in the cerebral cortex of newborn piglets. *Neurochem. Res.* 2002; 27:931-938.

112. Wolf H K, Buslei R, Schmidt-Kastner R, Schmidt-Kastner P K, Pietsch T, Wiestler O D, Blumcke I. Neun: A useful neuronal marker for diagnostic histopathology. *J. Histochem. Cytochem.* 1996; 44:1167-1171

113. Asahi M, Asahi K, Jung J C, del Zoppo G J, Fini M E, Lo E H. Role for matrix metalloproteinase 9 after focal cerebral ischemia: Effects of gene knockout and enzyme inhibition with bb-94. *J. Cereb. Blood Flow Metab.* 2000; 20:1681-1689

114. Norton W T, Poduslo S E. Myelination in rat brain: Method of myelin isolation. *J. Neurochem.* 1973; 21:749-757

115. Guan J, Bennet L, George S, Wu D, Waldvogel H J, Gluckman P D, Faull R L, Crosier P S, Gunn A J. Insulin-like growth factor-1 reduces postischemic white matter injury in fetal sheep. *J. Cereb. Blood Flow Metab.* 2001; 21:493-502

116. Stonestreet B S, Le E, Berard D J. Circulatory and metabolic effects of beta-adrenergic blockade in the hyperinsulinemic ovine fetus. *Am. J. Physiol.* 1993; 265: H1098-1106

117. Stonestreet B S, Widness J A, Berard D J. Circulatory and metabolic effects of hypoxia in the hyperinsulinemic ovine fetus. *Pediatr. Res.* 1995; 38:67-75

The invention claimed is:

1. A method of treating, reducing, or inhibiting ischemia resulting from hemorrhagic stroke in a patient in need thereof comprising administering to said patient a composition comprising inter-alpha inhibitor (IαI) and/or pre-alpha inhibitor (PαI).

2. The method of claim 1, wherein said ischemia is hypoxic ischemia.

3. The method of claim 1, wherein said ischemia is acute ischemia.

4. The method of claim 1, wherein said method comprises reducing the severity of said ischemia.

5. The method of claim 1, wherein said ischemia occurs in a tissue or cell type selected from brain, cerebral cortex, choroid plexus, cerebrum, cerebellum, neurons, astrocytes, and meningeal cells.

6. The method of claim 1, wherein said patient is a human.

7. The method of claim 1, wherein said composition is administered at a dosage of 1 mg/kg body weight to 50 mg/kg body weight.

8. The method of claim 1, wherein said composition is administered at a dosage ranging from 50 mg/dose to 1000 mg/dose.

9. The method of claim 1, wherein said composition comprises a pharmaceutically acceptable excipient, diluent, or carrier.

10. The method of claim 9, wherein said composition is a solid or a liquid.

11. The method of claim 9, wherein said composition is formulated for inhalation, insufflation, nebulization, injection, oral, rectal, topical, or intraperitoneal administration, intracerebral injection, intravenous delivery, or infusion.

12. A method of providing neuroprotection to a patient with brain ischemia or central nervous system (CNS) inflammation, said method comprising administering to said patient a composition comprising inter-alpha inhibitor (IαI) and/or pre-alpha inhibitor (PαI).

13. The method of claim 1, wherein the patient is an adult.

14. The method of claim 12, wherein said brain ischemia is due to hypoxic ischemia or stroke.

15. A method of treating ischemia in a patient with cancer, comprising administering to said patient a composition comprising inter-alpha inhibitor (IαI) and/or pre-alpha inhibitor (PαI).

16. The method of claim 1, wherein the patient was administered tissue plasminogen activator (TPA) prior to administration of the IαI and/or PαI.

17. A method of treating stroke in a subject in need thereof, comprising administering to the subject TPA and a composition comprising IαI and/or PαI.

18. The method of claim 17, wherein the IαI and/or PαI are administered after administration of the TPA.

19. The method of claim 17, wherein the IαI and/or PαI are administered concurrently with administration of the TPA.

* * * * *